(12) United States Patent
Brister et al.

(10) Patent No.: US 7,783,333 B2
(45) Date of Patent: Aug. 24, 2010

(54) TRANSCUTANEOUS MEDICAL DEVICE WITH VARIABLE STIFFNESS

(75) Inventors: Mark Brister, Encinitas, CA (US); James Brauker, San Diego, CA (US)

(73) Assignee: DexCom, Inc., San Diego, CA (US)

( * ) Notice: Subject to any disclaimer, the term of this patent is extended or adjusted under 35 U.S.C. 154(b) by 292 days.

(21) Appl. No.: 11/077,759

(22) Filed: Mar. 10, 2005

(65) Prior Publication Data

US 2006/0015024 A1    Jan. 19, 2006

Related U.S. Application Data

(60) Provisional application No. 60/587,800, filed on Jul. 13, 2004.

(51) Int. Cl.
*A61B 5/05* (2006.01)
*A61B 5/00* (2006.01)

(52) U.S. Cl. ............... 600/345; 600/309; 600/347; 600/365

(58) Field of Classification Search ............ 600/365, 600/347
See application file for complete search history.

(56) References Cited

U.S. PATENT DOCUMENTS

| | | |
|---|---|---|
| 1,526,464 A | 12/1925 | St. James |
| 1,564,641 A * | 12/1925 | St James .................. 313/265 |
| 2,402,306 A | 6/1946 | Turkel |
| 2,719,797 A | 10/1955 | Rosenblatt et al. |
| 3,210,578 A | 10/1965 | Sherer |
| 3,219,533 A | 11/1965 | Mullins |
| 3,381,371 A | 5/1968 | Russell |
| 3,506,032 A | 4/1970 | Eveleigh et al. |
| 3,556,950 A | 1/1971 | Dahms |
| 3,610,226 A | 10/1971 | Albisser |
| 3,652,475 A | 3/1972 | Wada et al. |
| 3,775,182 A | 11/1973 | Patton et al. |
| 3,780,727 A | 12/1973 | King |
| 3,826,244 A | 7/1974 | Salcman et al. |
| 3,837,339 A | 9/1974 | Aisenberg |
| 3,838,033 A | 9/1974 | Mindt et al. |
| 3,838,682 A | 10/1974 | Clark et al. |

(Continued)

FOREIGN PATENT DOCUMENTS

EP    0098592    1/1984

(Continued)

OTHER PUBLICATIONS

Atanasov, et al. 1994. Biosensor for continuos glucose monitoring. *Biotechnology and Bioengineering*, 43:262-266.

(Continued)

*Primary Examiner*—Patricia C Mallari
(74) *Attorney, Agent, or Firm*—Knobbe Martens Olson & Bear LLP

(57) ABSTRACT

The present invention relates generally to variable stiffness transcutaneous medical devices including a distal portion designed to be more flexible than a proximal portion. The variable stiffness can be provided by a variable pitch in one or more wires of the device, a variable cross-section in one or more wires of the device, and/or a variable hardening and/or softening in one or more wires of the device.

39 Claims, 5 Drawing Sheets

U.S. PATENT DOCUMENTS

| | | |
|---|---|---|
| 3,874,850 A | 4/1975 | Sorensen et al. |
| 3,910,256 A | 10/1975 | Clark et al. |
| 3,926,760 A | 12/1975 | Allen et al. |
| 3,933,593 A | 1/1976 | Sternberg |
| 3,943,918 A | 3/1976 | Lewis |
| 3,964,974 A | 6/1976 | Banauch et al. |
| 3,966,580 A | 6/1976 | Janata et al. |
| 3,979,274 A | 9/1976 | Newman |
| 4,008,717 A | 2/1977 | Kowarski |
| 4,016,866 A | 4/1977 | Lawton |
| 4,024,312 A | 5/1977 | Korpman |
| 4,036,749 A | 7/1977 | Anderson |
| 4,037,563 A | 7/1977 | Pflueger et al. |
| 4,040,908 A | 8/1977 | Clark, Jr. |
| 4,055,175 A | 10/1977 | Clemens et al. |
| 4,073,713 A | 2/1978 | Newman |
| 4,076,656 A | 2/1978 | White et al. |
| 4,109,505 A | 8/1978 | Clark et al. |
| 4,119,406 A | 10/1978 | Clemens |
| 4,151,845 A | 5/1979 | Clemens |
| 4,172,770 A | 10/1979 | Semersky et al. |
| 4,176,659 A | 12/1979 | Rolfe |
| 4,197,840 A | 4/1980 | Beck et al. |
| 4,197,852 A | 4/1980 | Schindler et al. |
| 4,206,755 A | 6/1980 | Klein |
| 4,215,703 A | 8/1980 | Willson |
| 4,240,438 A | 12/1980 | Updike et al. |
| 4,240,889 A | 12/1980 | Yoda et al. |
| 4,255,500 A | 3/1981 | Hooke |
| 4,259,540 A | 3/1981 | Sabia |
| 4,265,249 A | 5/1981 | Schindler et al. |
| 4,327,725 A | 5/1982 | Cortese et al. |
| 4,353,888 A | 10/1982 | Sefton |
| 4,366,040 A | 12/1982 | Marsoner et al. |
| 4,369,785 A | 1/1983 | Rehkopf et al. |
| 4,374,013 A | 2/1983 | Enfors |
| 4,378,016 A | 3/1983 | Loeb |
| 4,388,166 A | 6/1983 | Suzuki et al. |
| 4,402,694 A | 9/1983 | Ash et al. |
| 4,403,847 A | 9/1983 | Chrestensen |
| 4,415,666 A | 11/1983 | D'Orazio et al. |
| 4,419,535 A | 12/1983 | O'Hara |
| 4,431,004 A | 2/1984 | Bessman et al. |
| 4,431,507 A | 2/1984 | Nankai et al. |
| 4,432,366 A | 2/1984 | Margules |
| 4,436,094 A | 3/1984 | Cerami |
| 4,442,841 A | 4/1984 | Uehara et al. |
| 4,454,295 A | 6/1984 | Wittmann et al. |
| 4,457,339 A | 7/1984 | Juan et al. |
| 4,477,314 A | 10/1984 | Richter et al. |
| 4,478,222 A | 10/1984 | Koning et al. |
| 4,486,290 A | 12/1984 | Cahalan et al. |
| 4,492,575 A | 1/1985 | Mabille |
| 4,494,950 A | 1/1985 | Fischell |
| 4,506,680 A | 3/1985 | Stokes |
| 4,519,973 A | 5/1985 | Cahalan et al. |
| 4,526,569 A | 7/1985 | Bernardi |
| 4,534,825 A | 8/1985 | Koning et al. |
| 4,535,786 A | 8/1985 | Kater |
| 4,538,616 A | 9/1985 | Rogoff |
| 4,565,665 A | 1/1986 | Fogt |
| 4,565,666 A | 1/1986 | Cahalan et al. |
| 4,568,444 A | 2/1986 | Nakamura et al. |
| 4,571,292 A | 2/1986 | Liu et al. |
| 4,573,968 A | 3/1986 | Parker |
| 4,577,642 A | 3/1986 | Stokes |
| 4,583,976 A | 4/1986 | Ferguson |
| 4,592,824 A | 6/1986 | Smith et al. |
| 4,600,495 A | 7/1986 | Fogt |
| 4,614,514 A | 9/1986 | Carr et al. |
| 4,619,793 A | 10/1986 | Lee |
| 4,626,104 A | 12/1986 | Pointon et al. |
| RE32,361 E | 2/1987 | Duggan |
| 4,650,547 A | 3/1987 | Gough |
| 4,655,880 A | 4/1987 | Liu |
| 4,663,824 A | 5/1987 | Kenmochi |
| 4,671,288 A | 6/1987 | Gough |
| 4,672,970 A | 6/1987 | Uchida et al. |
| 4,680,268 A | 7/1987 | Clark, Jr. |
| 4,685,463 A | 8/1987 | Williams |
| 4,694,861 A | 9/1987 | Goodale et al. |
| 4,703,756 A | 11/1987 | Gough et al. |
| 4,705,503 A | 11/1987 | Dorman et al. |
| 4,711,251 A | 12/1987 | Stokes |
| 4,721,677 A | 1/1988 | Clark, Jr. |
| 4,736,748 A | 4/1988 | Nakamura et al. |
| 4,747,822 A | 5/1988 | Peabody |
| 4,750,496 A | 6/1988 | Reinhart et al. |
| 4,753,652 A | 6/1988 | Langer et al. |
| 4,755,168 A | 7/1988 | Romanelli et al. |
| 4,757,022 A | 7/1988 | Shults et al. |
| 4,759,828 A | 7/1988 | Young et al. |
| 4,763,648 A | 8/1988 | Wyatt |
| 4,777,953 A | 10/1988 | Ash et al. |
| 4,781,798 A | 11/1988 | Gough |
| 4,784,157 A | 11/1988 | Halls et al. |
| 4,786,394 A | 11/1988 | Enzer et al. |
| 4,789,467 A | 12/1988 | Lindsay et al. |
| 4,791,932 A | 12/1988 | Margules |
| 4,803,243 A | 2/1989 | Fujimoto et al. |
| 4,805,624 A | 2/1989 | Yao et al. |
| 4,808,089 A | 2/1989 | Buchholtz et al. |
| 4,808,292 A | 2/1989 | Kessler et al. |
| 4,809,704 A | 3/1989 | Sogawa et al. |
| 4,810,243 A | 3/1989 | Howson |
| 4,810,470 A | 3/1989 | Burkhardt et al. |
| 4,813,424 A | 3/1989 | Wilkins |
| 4,815,471 A | 3/1989 | Stobie |
| 4,820,281 A | 4/1989 | Lawler |
| 4,822,336 A | 4/1989 | DiTraglia |
| 4,828,544 A | 5/1989 | Lane et al. |
| 4,830,013 A | 5/1989 | Maxwell |
| 4,831,070 A | 5/1989 | McInally et al. |
| 4,832,005 A | 5/1989 | Takamiya et al. |
| 4,832,034 A | 5/1989 | Pizziconi |
| 4,834,101 A | 5/1989 | Collison et al. |
| 4,838,281 A | 6/1989 | Rogers et al. |
| 4,841,974 A | 6/1989 | Gumbriecht et al. |
| 4,849,458 A | 7/1989 | Reed et al. |
| 4,854,322 A | 8/1989 | Ash et al. |
| 4,858,615 A | 8/1989 | Meinema |
| 4,867,741 A | 9/1989 | Portnoy |
| 4,871,440 A | 10/1989 | Nagata et al. |
| 4,874,363 A | 10/1989 | Abell |
| 4,883,057 A | 11/1989 | Broderick |
| 4,883,467 A | 11/1989 | Franetzki et al. |
| 4,889,528 A | 12/1989 | Nadai et al. |
| 4,889,744 A | 12/1989 | Quaid |
| 4,890,620 A | 1/1990 | Gough |
| 4,890,621 A | 1/1990 | Hakky |
| 4,900,305 A | 2/1990 | Smith et al. |
| 4,907,857 A | 3/1990 | Giuliani et al. |
| 4,909,786 A | 3/1990 | Gijselhart et al. |
| 4,919,141 A | 4/1990 | Zier et al. |
| 4,919,649 A | 4/1990 | Timothy et al. |
| 4,921,477 A | 5/1990 | Davis |
| 4,921,480 A | 5/1990 | Sealfon |
| 4,925,444 A | 5/1990 | Orkin et al. |
| 4,927,516 A | 5/1990 | Yamaguchi et al. |
| 4,928,694 A | 5/1990 | Maxwell |
| 4,934,369 A | 6/1990 | Maxwell |
| 4,934,375 A | 6/1990 | Cole et al. |
| 4,944,299 A | 7/1990 | Silvian |
| 4,946,439 A | 8/1990 | Eggers |

| Patent No. | Date | Inventor |
|---|---|---|
| 4,951,669 A | 8/1990 | Maxwell et al. |
| 4,953,552 A | 9/1990 | DeMarzo |
| 4,955,861 A | 9/1990 | Enegren et al. |
| 4,957,483 A | 9/1990 | Gonser et al. |
| 4,958,148 A | 9/1990 | Olson |
| 4,963,595 A | 10/1990 | Ward et al. |
| 4,966,579 A | 10/1990 | Polaschegg |
| 4,967,940 A | 11/1990 | Blette |
| 4,974,592 A | 12/1990 | Branco |
| 4,974,929 A | 12/1990 | Curry |
| 4,975,175 A | 12/1990 | Karube et al. |
| 4,976,687 A | 12/1990 | Martin |
| 4,979,509 A | 12/1990 | Hakky |
| 4,984,929 A | 1/1991 | Rock et al. |
| 4,986,271 A | 1/1991 | Wilkins |
| 4,986,671 A | 1/1991 | Sun et al. |
| 4,988,341 A | 1/1991 | Columbus et al. |
| 4,988,758 A | 1/1991 | Fukuda et al. |
| 4,992,794 A | 2/1991 | Brouwers |
| 4,994,026 A | 2/1991 | Fecondini |
| 4,994,167 A | 2/1991 | Shults et al. |
| 4,997,627 A | 3/1991 | Bergkuist et al. |
| 5,002,055 A | 3/1991 | Merki et al. |
| 5,002,572 A | 3/1991 | Picha |
| 5,006,050 A | 4/1991 | Cooke et al. |
| 5,006,111 A | 4/1991 | Inokuchi et al. |
| 5,007,929 A | 4/1991 | Quaid |
| 5,009,251 A | 4/1991 | Pike et al. |
| 5,026,348 A | 6/1991 | Venegas |
| 5,030,199 A | 7/1991 | Barwick et al. |
| 5,030,333 A | 7/1991 | Clark, Jr. |
| 5,034,112 A | 7/1991 | Murase et al. |
| 5,041,092 A | 8/1991 | Barwick |
| 5,045,057 A | 9/1991 | Van Driessche et al. |
| 5,046,496 A | 9/1991 | Betts et al. |
| 5,048,525 A | 9/1991 | Maxwell |
| 5,050,612 A | 9/1991 | Matsumura |
| 5,055,171 A | 10/1991 | Peck |
| 5,055,198 A | 10/1991 | Shettigar |
| 5,059,654 A | 10/1991 | Hou et al. |
| 5,068,536 A | 11/1991 | Rosenthal |
| 5,082,550 A | 1/1992 | Rishpon et al. |
| 5,088,981 A | 2/1992 | Howson et al. |
| 5,089,112 A | 2/1992 | Skotheim et al. |
| 5,089,421 A | 2/1992 | Dieffenbach |
| 5,096,669 A | 3/1992 | Lauks et al. |
| 5,097,834 A | 3/1992 | Skrabal |
| 5,098,377 A | 3/1992 | Borsanyi et al. |
| 5,101,814 A | 4/1992 | Palti |
| 5,108,819 A | 4/1992 | Heller et al. |
| 5,109,850 A | 5/1992 | Blanco et al. |
| 5,112,301 A | 5/1992 | Fenton et al. |
| 5,116,313 A | 5/1992 | Mcgregor |
| 5,127,405 A | 7/1992 | Alcala et al. |
| 5,140,985 A | 8/1992 | Schroeder et al. |
| 5,145,565 A | 9/1992 | Kater et al. |
| 5,152,746 A | 10/1992 | Atkinson et al. |
| 5,160,418 A | 11/1992 | Mullen |
| 5,161,532 A | 11/1992 | Joseph |
| 5,165,406 A | 11/1992 | Wong et al. |
| 5,165,407 A * | 11/1992 | Wilson et al. ............... 600/345 |
| 5,176,632 A | 1/1993 | Bernardi |
| 5,176,658 A | 1/1993 | Ranford |
| 5,178,142 A | 1/1993 | Harjunmaa et al. |
| 5,182,004 A | 1/1993 | Kohno |
| 5,188,591 A | 2/1993 | Dorsey |
| 5,190,041 A | 3/1993 | Palti |
| 5,195,963 A | 3/1993 | Yafuso et al. |
| 5,198,771 A | 3/1993 | Fidler et al. |
| 5,202,261 A | 4/1993 | Musho et al. |
| 5,208,147 A | 5/1993 | Kagenow et al. |
| 5,220,917 A | 6/1993 | Cammilli et al. |
| 5,220,920 A | 6/1993 | Gharib |
| 5,224,929 A | 7/1993 | Remiszewski |
| 5,225,063 A | 7/1993 | Gumbrecht et al. |
| 5,232,434 A | 8/1993 | Inagaki et al. |
| 5,235,003 A | 8/1993 | Ward et al. |
| 5,243,696 A | 9/1993 | Carr et al. |
| 5,243,982 A | 9/1993 | Mostl et al. |
| 5,243,983 A | 9/1993 | Tarr et al. |
| 5,249,576 A | 10/1993 | Golberger et al. |
| 5,254,102 A | 10/1993 | Ogawa |
| 5,265,594 A | 11/1993 | Olsson et al. |
| 5,266,179 A | 11/1993 | Nankai et al. |
| 5,271,736 A | 12/1993 | Picha |
| 5,271,815 A | 12/1993 | Wong et al. |
| 5,279,294 A | 1/1994 | Anderson et al. |
| 5,281,319 A | 1/1994 | Kaneko et al. |
| 5,282,848 A | 2/1994 | Schmitt |
| 5,284,140 A | 2/1994 | Allen et al. |
| 5,284,570 A | 2/1994 | Savage et al. |
| 5,285,513 A | 2/1994 | Kaufman et al. |
| 5,287,753 A | 2/1994 | Routh et al. |
| 5,298,022 A | 3/1994 | Bernardi |
| 5,299,571 A | 4/1994 | Mastrototaro |
| 5,302,093 A | 4/1994 | Owens et al. |
| 5,307,263 A | 4/1994 | Brown |
| 5,310,469 A | 5/1994 | Cunningham et al. |
| 5,311,908 A | 5/1994 | Barone et al. |
| 5,314,471 A | 5/1994 | Brauker et al. |
| 5,316,452 A | 5/1994 | Bogen et al. |
| 5,318,511 A | 6/1994 | Riquier et al. |
| 5,322,063 A | 6/1994 | Allen et al. |
| 5,324,322 A | 6/1994 | Grill et al. |
| 5,326,356 A | 7/1994 | Della Valle et al. |
| 5,326,449 A | 7/1994 | Cunningham |
| 5,330,634 A | 7/1994 | Wong et al. |
| 5,335,658 A | 8/1994 | Bedingham |
| 5,337,747 A | 8/1994 | Neftel |
| 5,342,789 A | 8/1994 | Chick et al. |
| 5,344,454 A | 9/1994 | Clarke et al. |
| 5,345,932 A | 9/1994 | Yafuso et al. |
| 5,348,788 A | 9/1994 | White |
| 5,352,348 A | 10/1994 | Young et al. |
| 5,352,351 A | 10/1994 | White |
| 5,354,272 A | 10/1994 | Swendson et al. |
| 5,354,449 A | 10/1994 | Band et al. |
| 5,356,375 A | 10/1994 | Higley |
| 5,356,378 A | 10/1994 | Doan |
| 5,356,786 A | 10/1994 | Heller et al. |
| 5,368,224 A | 11/1994 | Richardson et al. |
| 5,368,562 A | 11/1994 | Blomquist et al. |
| 5,372,135 A | 12/1994 | Mendelson et al. |
| 5,372,709 A | 12/1994 | Hood |
| 5,372,719 A | 12/1994 | Afeyan et al. |
| 5,376,070 A | 12/1994 | Purvis et al. |
| 5,378,229 A | 1/1995 | Layer et al. |
| 5,380,268 A | 1/1995 | Wheeler |
| 5,380,491 A | 1/1995 | Carver et al. |
| 5,380,536 A | 1/1995 | Hubbell et al. |
| 5,380,665 A | 1/1995 | Cusack et al. |
| 5,384,028 A | 1/1995 | Ito |
| 5,390,671 A | 2/1995 | Lord et al. |
| 5,391,250 A | 2/1995 | Cheney, II et al. |
| 5,397,848 A | 3/1995 | Yang et al. |
| 5,411,052 A | 5/1995 | Murray |
| 5,411,647 A | 5/1995 | Johnson et al. |
| 5,411,866 A | 5/1995 | Luong |
| 5,417,206 A | 5/1995 | Kaneyoshi |
| 5,421,328 A | 6/1995 | Bedingham |
| 5,423,738 A | 6/1995 | Robinson et al. |
| 5,423,749 A | 6/1995 | Merte et al. |
| 5,426,032 A | 6/1995 | Phillips |
| 5,429,485 A | 7/1995 | Dodge |
| 5,429,602 A | 7/1995 | Hauser |
| 5,429,735 A | 7/1995 | Johnson et al. |

| | | | | | |
|---|---|---|---|---|---|
| 5,431,160 A | 7/1995 | Wilkins | 5,651,767 A | 7/1997 | Schulman et al. |
| 5,431,174 A | 7/1995 | Knute | 5,653,756 A | 8/1997 | Clarke et al. |
| 5,431,921 A | 7/1995 | Thombre | 5,653,863 A | 8/1997 | Genshaw et al. |
| 5,434,412 A | 7/1995 | Sodickson et al. | 5,658,250 A | 8/1997 | Blomquist et al. |
| 5,437,635 A | 8/1995 | Fields et al. | 5,658,330 A | 8/1997 | Carlisle et al. |
| 5,445,610 A | 8/1995 | Evert | 5,660,163 A | 8/1997 | Schulman et al. |
| 5,453,199 A | 9/1995 | Afeyan et al. | 5,665,061 A | 9/1997 | Antwiler |
| 5,453,278 A | 9/1995 | Chan et al. | 5,665,065 A | 9/1997 | Colman et al. |
| 5,462,051 A | 10/1995 | Oka et al. | 5,667,504 A | 9/1997 | Baumann et al. |
| 5,462,064 A | 10/1995 | D'Angelo et al. | 5,676,651 A | 10/1997 | Larson et al. |
| 5,462,645 A | 10/1995 | Albery et al. | 5,676,820 A | 10/1997 | Wang et al. |
| 5,466,356 A | 11/1995 | Schneider et al. | 5,682,884 A | 11/1997 | Hill |
| 5,474,552 A | 12/1995 | Palti | 5,686,829 A | 11/1997 | Girault |
| 5,476,776 A | 12/1995 | Wilkins | 5,688,239 A | 11/1997 | Walker |
| 5,482,008 A | 1/1996 | Stafford et al. | 5,688,244 A | 11/1997 | Lang |
| 5,482,446 A | 1/1996 | Williamson et al. | 5,697,366 A | 12/1997 | Kimball et al. |
| 5,482,473 A | 1/1996 | Lord et al. | 5,697,899 A | 12/1997 | Hillman et al. |
| 5,484,404 A | 1/1996 | Schulman et al. | 5,704,354 A | 1/1998 | Preidel et al. |
| 5,486,776 A | 1/1996 | Wilkins | 5,706,807 A | 1/1998 | Picha |
| 5,494,562 A | 2/1996 | Maley et al. | 5,707,502 A | 1/1998 | McCaffrey et al. |
| 5,497,772 A | 3/1996 | Schulman et al. | 5,711,861 A | 1/1998 | Ward et al. |
| 5,502,396 A | 3/1996 | Desarzens et al. | 5,713,888 A | 2/1998 | Neuenfeldt et al. |
| 5,505,828 A | 4/1996 | Wong et al. | 5,714,123 A | 2/1998 | Sohrab |
| 5,507,288 A | 4/1996 | Bocker et al. | 5,733,336 A | 3/1998 | Neuenfeldt et al. |
| 5,509,888 A | 4/1996 | Miller | 5,735,273 A | 4/1998 | Kurnik et al. |
| 5,512,046 A | 4/1996 | Pusinelli et al. | 5,741,330 A | 4/1998 | Brauker et al. |
| 5,512,248 A | 4/1996 | Van | 5,741,634 A | 4/1998 | Nozoe et al. |
| 5,514,253 A | 5/1996 | Davis et al. | 5,743,262 A | 4/1998 | Lepper, Jr. et al. |
| 5,515,851 A | 5/1996 | Goldstein | 5,749,832 A | 5/1998 | Vadgama et al. |
| 5,518,601 A | 5/1996 | Foos et al. | 5,749,907 A | 5/1998 | Mann |
| 5,531,679 A | 7/1996 | Schulman et al. | 5,755,692 A | 5/1998 | Manicom |
| 5,531,878 A | 7/1996 | Vadgama et al. | 5,756,632 A | 5/1998 | Ward et al. |
| 5,540,828 A | 7/1996 | Yacynych | 5,758,643 A | 6/1998 | Wong et al. |
| 5,545,220 A | 8/1996 | Andrews et al. | 5,763,760 A | 6/1998 | Gumbrecht et al. |
| 5,545,223 A | 8/1996 | Neuenfeldt et al. | 5,766,151 A | 6/1998 | Valley et al. |
| 5,549,547 A | 8/1996 | Cohen et al. | 5,776,324 A | 7/1998 | Usala |
| 5,549,548 A | 8/1996 | Larsson | 5,779,665 A | 7/1998 | Mastrototaro et al. |
| 5,549,569 A | 8/1996 | Lynn et al. | 5,782,912 A | 7/1998 | Brauker et al. |
| 5,549,651 A | 8/1996 | Lynn | 5,787,900 A | 8/1998 | Butler et al. |
| 5,549,675 A | 8/1996 | Neuenfeldt et al. | 5,791,344 A | 8/1998 | Schulman et al. |
| 5,551,850 A | 9/1996 | Williamson et al. | 5,791,880 A | 8/1998 | Wilson |
| 5,554,339 A | 9/1996 | Cozzette | 5,795,774 A | 8/1998 | Matsumoto et al. |
| 5,562,614 A | 10/1996 | O'Donnell | 5,798,065 A | 8/1998 | Picha |
| 5,562,615 A | 10/1996 | Nassif | 5,800,383 A | 9/1998 | Chandler et al. |
| 5,564,439 A | 10/1996 | Picha | 5,800,420 A | 9/1998 | Gross et al. |
| 5,568,806 A | 10/1996 | Cheney et al. | 5,800,529 A | 9/1998 | Brauker et al. |
| 5,569,186 A | 10/1996 | Lord et al. | 5,807,274 A | 9/1998 | Henning et al. |
| 5,569,188 A | 10/1996 | Mackool | 5,807,312 A | 9/1998 | Dzwonkiewicz |
| 5,569,219 A | 10/1996 | Hakki et al. | 5,807,375 A | 9/1998 | Gross et al. |
| 5,569,462 A | 10/1996 | Martinson et al. | 5,807,406 A | 9/1998 | Brauker et al. |
| 5,571,395 A | 11/1996 | Park et al. | 5,810,770 A | 9/1998 | Chin et al. |
| 5,575,930 A | 11/1996 | Tietje-Girault et al. | 5,811,487 A | 9/1998 | Schulz, Jr. et al. |
| 5,577,499 A | 11/1996 | Teves | 5,814,599 A | 9/1998 | Mitragotri et al. |
| 5,582,184 A | 12/1996 | Erickson et al. | 5,820,589 A | 10/1998 | Torgerson et al. |
| 5,582,497 A | 12/1996 | Noguchi | 5,820,622 A | 10/1998 | Gross et al. |
| 5,582,593 A | 12/1996 | Hultman | 5,822,715 A | 10/1998 | Worthington et al. |
| 5,584,813 A | 12/1996 | Livingston et al. | 5,823,802 A | 10/1998 | Bartley |
| 5,584,876 A | 12/1996 | Bruchman et al. | 5,836,887 A | 11/1998 | Oka et al. |
| 5,587,273 A | 12/1996 | Yan et al. | 5,836,989 A | 11/1998 | Shelton |
| 5,588,560 A | 12/1996 | Benedict et al. | 5,837,454 A | 11/1998 | Cozzette et al. |
| 5,589,133 A | 12/1996 | Suzuki | 5,837,728 A | 11/1998 | Purcell |
| 5,589,563 A | 12/1996 | Ward et al. | 5,840,026 A | 11/1998 | Uber et al. |
| 5,590,651 A | 1/1997 | Shaffer et al. | 5,840,148 A | 11/1998 | Campbell et al. |
| 5,593,440 A | 1/1997 | Brauker et al. | 5,840,240 A | 11/1998 | Stenoien et al. |
| 5,593,852 A | 1/1997 | Heller et al. | 5,851,197 A | 12/1998 | Marano et al. |
| 5,609,572 A | 3/1997 | Lang | 5,861,019 A | 1/1999 | Sun et al. |
| 5,611,900 A | 3/1997 | Worden et al. | 5,863,400 A | 1/1999 | Drummond et al. |
| 5,624,409 A | 4/1997 | Seale | 5,871,514 A | 2/1999 | Wiklund et al. |
| 5,626,563 A | 5/1997 | Dodge et al. | 5,873,862 A | 2/1999 | Lopez |
| 5,628,619 A | 5/1997 | Wilson | 5,879,373 A | 3/1999 | Roper et al. |
| 5,637,083 A | 6/1997 | Bertrand et al. | 5,882,494 A | 3/1999 | Van Antwerp |
| 5,640,470 A | 6/1997 | Iyer et al. | 5,895,235 A | 4/1999 | Droz |
| 5,643,195 A | 7/1997 | Drevet et al. | 5,897,525 A | 4/1999 | Dey et al. |

| Patent No. | Date | Name |
|---|---|---|
| 5,897,578 A | 4/1999 | Wiklund et al. |
| 5,904,666 A | 5/1999 | Dedecker et al. |
| 5,904,708 A | 5/1999 | Goedeke |
| 5,911,219 A | 6/1999 | Aylsworth et al. |
| 5,913,998 A | 6/1999 | Butler et al. |
| 5,914,026 A | 6/1999 | Blubaugh, Jr. et al. |
| 5,916,445 A | 6/1999 | Hjerten et al. |
| 5,919,215 A | 7/1999 | Wiklund et al. |
| 5,921,951 A | 7/1999 | Morris |
| 5,928,155 A | 7/1999 | Eggers et al. |
| 5,928,182 A | 7/1999 | Kraus et al. |
| 5,928,189 A | 7/1999 | Phillips et al. |
| 5,928,195 A | 7/1999 | Malamud et al. |
| 5,932,175 A | 8/1999 | Knute et al. |
| 5,933,136 A | 8/1999 | Brown |
| 5,935,785 A | 8/1999 | Reber et al. |
| 5,938,636 A | 8/1999 | Kramer et al. |
| 5,947,911 A | 9/1999 | Wong et al. |
| 5,954,643 A | 9/1999 | Van Antwerp et al. |
| 5,954,954 A | 9/1999 | Houck et al. |
| 5,957,854 A | 9/1999 | Besson et al. |
| 5,959,050 A | 9/1999 | Mosbach et al. |
| 5,963,132 A | 10/1999 | Yoakum |
| 5,964,804 A | 10/1999 | Brauker et al. |
| 5,964,993 A | 10/1999 | Blubaugh et al. |
| 5,965,380 A | 10/1999 | Heller et al. |
| 5,971,922 A | 10/1999 | Arita et al. |
| 5,972,199 A | 10/1999 | Heller |
| 5,976,085 A | 11/1999 | Kimball et al. |
| 5,995,208 A | 11/1999 | Sarge et al. |
| 5,995,860 A | 11/1999 | Sun et al. |
| 6,001,067 A | 12/1999 | Shults et al. |
| 6,011,984 A | 1/2000 | Van Antwerp et al. |
| 6,013,113 A | 1/2000 | Mika |
| 6,014,577 A | 1/2000 | Henning et al. |
| 6,016,448 A | 1/2000 | Busacker et al. |
| 6,017,435 A | 1/2000 | Hassard et al. |
| 6,024,720 A | 2/2000 | Chandler et al. |
| 6,027,445 A | 2/2000 | Von Bahr |
| 6,032,059 A | 2/2000 | Henning et al. |
| 6,032,667 A | 3/2000 | Heinonen |
| 6,036,924 A | 3/2000 | Simons et al. |
| 6,048,691 A | 4/2000 | Maracas |
| 6,049,727 A | 4/2000 | Crothall |
| 6,051,372 A | 4/2000 | Bayerl et al. |
| 6,051,389 A | 4/2000 | Ahl et al. |
| 6,057,377 A | 5/2000 | Sasaki et al. |
| 6,059,946 A | 5/2000 | Yukawa et al. |
| 6,063,637 A | 5/2000 | Arnold et al. |
| 6,066,088 A | 5/2000 | Davis |
| 6,066,448 A | 5/2000 | Wohlstadter et al. |
| 6,071,391 A | 6/2000 | Gotoh et al. |
| 6,077,299 A | 6/2000 | Adelberg et al. |
| 6,080,583 A | 6/2000 | Von Bahr |
| 6,081,735 A | 6/2000 | Diab et al. |
| 6,081,736 A | 6/2000 | Colvin et al. |
| 6,083,523 A | 7/2000 | Dionne et al. |
| 6,088,608 A | 7/2000 | Schulman et al. |
| 6,090,087 A | 7/2000 | Tsukada et al. |
| 6,093,156 A | 7/2000 | Cunningham et al. |
| 6,099,511 A | 8/2000 | Devos et al. |
| 6,103,533 A | 8/2000 | Hassard et al. |
| 6,107,083 A | 8/2000 | Collins et al. |
| 6,117,290 A | 9/2000 | Say et al. |
| 6,119,028 A | 9/2000 | Schulman et al. |
| 6,122,536 A | 9/2000 | Sun et al. |
| 6,123,827 A | 9/2000 | Wong et al. |
| 6,128,519 A | 10/2000 | Say |
| 6,134,461 A | 10/2000 | Say et al. |
| 6,135,978 A | 10/2000 | Houben et al. |
| 6,144,869 A | 11/2000 | Berner et al. |
| 6,159,186 A | 12/2000 | Wickham et al. |
| 6,162,201 A | 12/2000 | Cohen et al. |
| 6,162,611 A | 12/2000 | Heller et al. |
| 6,164,921 A | 12/2000 | Moubayed et al. |
| 6,165,154 A | 12/2000 | Gray et al. |
| 6,168,568 B1 | 1/2001 | Gavriely |
| 6,169,155 B1 | 1/2001 | Alvarez et al. |
| 6,171,276 B1 | 1/2001 | Lippe et al. |
| 6,175,752 B1 | 1/2001 | Say et al. |
| 6,180,416 B1 | 1/2001 | Kurnik et al. |
| 6,183,437 B1 | 2/2001 | Walker |
| 6,187,062 B1 | 2/2001 | Oweis et al. |
| 6,191,860 B1 | 2/2001 | Klinger et al. |
| 6,201,980 B1 | 3/2001 | Darrow et al. |
| 6,201,993 B1 | 3/2001 | Kruse et al. |
| 6,208,894 B1 | 3/2001 | Schulman et al. |
| 6,212,416 B1 | 4/2001 | Ward et al. |
| 6,212,424 B1 | 4/2001 | Robinson |
| 6,213,739 B1 | 4/2001 | Phallen et al. |
| 6,219,574 B1 | 4/2001 | Cormier et al. |
| 6,223,083 B1 | 4/2001 | Rosar |
| 6,230,059 B1 | 5/2001 | Duffin |
| 6,231,879 B1 | 5/2001 | Li et al. |
| 6,232,783 B1 | 5/2001 | Merrill |
| 6,233,080 B1 | 5/2001 | Brenner et al. |
| 6,233,471 B1 | 5/2001 | Berner et al. |
| 6,248,067 B1 | 6/2001 | Causey, III et al. |
| 6,248,077 B1 | 6/2001 | Elson et al. |
| 6,248,093 B1 | 6/2001 | Moberg |
| 6,251,280 B1 | 6/2001 | Dai et al. |
| 6,254,586 B1 | 7/2001 | Mann et al. |
| 6,256,522 B1 | 7/2001 | Schultz |
| 6,259,937 B1 | 7/2001 | Schulman et al. |
| 6,263,222 B1 | 7/2001 | Diab et al. |
| 6,264,825 B1 | 7/2001 | Blackburn et al. |
| 6,270,478 B1 | 8/2001 | Mern et al. |
| 6,272,364 B1 | 8/2001 | Kurnik |
| 6,272,480 B1 | 8/2001 | Tresp et al. |
| 6,274,285 B1 | 8/2001 | Gries et al. |
| 6,274,686 B1 | 8/2001 | Mosbach |
| 6,275,717 B1 | 8/2001 | Gross et al. |
| 6,280,408 B1 | 8/2001 | Sipin |
| 6,284,478 B1 | 9/2001 | Heller et al. |
| 6,299,578 B1 | 10/2001 | Kurnik et al. |
| 6,299,583 B1 | 10/2001 | Eggers et al. |
| 6,300,002 B1 | 10/2001 | Webb et al. |
| 6,302,855 B1 | 10/2001 | Knobbe et al. |
| 6,309,351 B1 | 10/2001 | Kurnik et al. |
| 6,309,384 B1 | 10/2001 | Harrington et al. |
| 6,309,884 B1 | 10/2001 | Cooper et al. |
| 6,310,110 B1 | 10/2001 | Markowitz et al. |
| 6,315,738 B1 | 11/2001 | Nishikawa et al. |
| 6,319,566 B1 | 11/2001 | Polanyi et al. |
| 6,325,978 B1 | 12/2001 | Labuda et al. |
| 6,325,979 B1 | 12/2001 | Hahn et al. |
| 6,326,160 B1 | 12/2001 | Dunn et al. |
| 6,329,161 B1 | 12/2001 | Heller et al. |
| 6,329,929 B1 | 12/2001 | Weijand et al. |
| 6,330,464 B1 | 12/2001 | Colvin, Jr. et al. |
| 6,356,776 B1 | 3/2002 | Berner et al. |
| 6,358,225 B1 | 3/2002 | Butterfield |
| 6,360,888 B1 | 3/2002 | McIvor et al. |
| 6,365,670 B1 | 4/2002 | Fry |
| 6,368,141 B1 | 4/2002 | VanAntwerp et al. |
| 6,370,941 B2 | 4/2002 | Nakamura et al. |
| 6,379,317 B1 | 4/2002 | Kintzig et al. |
| 6,391,019 B1 | 5/2002 | Ito |
| 6,402,703 B1 | 6/2002 | Kensey et al. |
| 6,403,944 B1 | 6/2002 | Mackenzie et al. |
| 6,406,066 B1 | 6/2002 | Uegane |
| 6,416,651 B1 | 7/2002 | Miller |
| 6,418,332 B1 | 7/2002 | Mastrototaro et al. |
| 6,424,847 B1 | 7/2002 | Mastrototaro et al. |
| 6,430,437 B1 | 8/2002 | Marro |
| 6,447,448 B1 | 9/2002 | Ishikawa et al. |

| | | |
|---|---|---|
| 6,447,542 B1 | 9/2002 | Weadock |
| 6,459,917 B1 | 10/2002 | Gowda et al. |
| 6,461,496 B1 | 10/2002 | Feldman et al. |
| 6,464,849 B1 | 10/2002 | Say et al. |
| 6,466,810 B1 | 10/2002 | Ward et al. |
| 6,467,480 B1 | 10/2002 | Meier et al. |
| 6,471,689 B1 | 10/2002 | Joseph et al. |
| 6,474,360 B1 | 11/2002 | Ito |
| 6,475,750 B1 | 11/2002 | Han et al. |
| 6,477,392 B1 | 11/2002 | Honigs et al. |
| 6,477,395 B2 | 11/2002 | Schulman et al. |
| 6,484,045 B1 | 11/2002 | Holker et al. |
| 6,484,046 B1 | 11/2002 | Say et al. |
| 6,485,449 B2 | 11/2002 | Ito |
| 6,488,652 B1 | 12/2002 | Weijand et al. |
| 6,494,879 B2 | 12/2002 | Lennox et al. |
| 6,498,043 B1 | 12/2002 | Schulman et al. |
| 6,498,941 B1 | 12/2002 | Jackson |
| 6,501,976 B1 | 12/2002 | Sohrab |
| 6,510,239 B1 | 1/2003 | Heckel |
| 6,510,329 B2 | 1/2003 | Heckel |
| 6,512,939 B1 | 1/2003 | Colvin et al. |
| 6,514,718 B2 | 2/2003 | Heller et al. |
| 6,517,508 B1 | 2/2003 | Utterberg et al. |
| 6,520,326 B2 | 2/2003 | Mcivor et al. |
| 6,520,477 B2 | 2/2003 | Trimmer |
| 6,520,937 B2 | 2/2003 | Hart et al. |
| 6,520,997 B1 | 2/2003 | Pekkarinen et al. |
| 6,526,298 B1 | 2/2003 | Khalil et al. |
| 6,527,729 B1 | 3/2003 | Turcott |
| 6,534,711 B1 | 3/2003 | Pollack |
| 6,536,433 B1 | 3/2003 | Cewers |
| 6,537,318 B1 | 3/2003 | Ita et al. |
| 6,541,107 B1 | 4/2003 | Zhong et al. |
| 6,544,212 B2 | 4/2003 | Galley et al. |
| 6,545,085 B2 | 4/2003 | Kilgour et al. |
| 6,546,268 B1 | 4/2003 | Ishikawa et al. |
| 6,546,269 B1 | 4/2003 | Kurnik |
| 6,547,839 B2 | 4/2003 | Zhang et al. |
| 6,551,496 B1 | 4/2003 | Moles et al. |
| 6,553,241 B2 | 4/2003 | Mannheimer et al. |
| 6,553,244 B2 | 4/2003 | Lesho et al. |
| 6,554,805 B2 | 4/2003 | Hiejima |
| 6,554,822 B1 | 4/2003 | Holschneider et al. |
| 6,558,320 B1 | 5/2003 | Causey, III et al. |
| 6,558,321 B1 | 5/2003 | Burd et al. |
| 6,558,347 B1 | 5/2003 | Jhuboo et al. |
| 6,558,351 B1 | 5/2003 | Steil et al. |
| 6,560,471 B1 | 5/2003 | Heller et al. |
| 6,561,978 B1 | 5/2003 | Conn et al. |
| 6,565,509 B1 | 5/2003 | Say et al. |
| 6,565,535 B2 | 5/2003 | Zaias et al. |
| 6,565,807 B1 | 5/2003 | Patterson et al. |
| 6,572,545 B2 | 6/2003 | Knobbe et al. |
| 6,572,579 B1 | 6/2003 | Raghavan et al. |
| 6,574,490 B2 | 6/2003 | Abbink et al. |
| 6,575,905 B2 | 6/2003 | Knobbe et al. |
| 6,579,257 B1 | 6/2003 | Elgas et al. |
| 6,579,498 B1 | 6/2003 | Eglise |
| 6,579,690 B1 | 6/2003 | Bonnecaze et al. |
| 6,585,644 B2 | 7/2003 | Lebel et al. |
| 6,585,675 B1 | 7/2003 | O'Mahony et al. |
| 6,589,229 B1 | 7/2003 | Connelly et al. |
| 6,591,125 B1 | 7/2003 | Buse et al. |
| 6,594,514 B2 | 7/2003 | Berner et al. |
| 6,595,756 B2 | 7/2003 | Gray et al. |
| 6,595,919 B2 | 7/2003 | Berner et al. |
| 6,602,221 B1 | 8/2003 | Saravia et al. |
| 6,605,072 B2 | 8/2003 | Struys et al. |
| 6,609,071 B2 | 8/2003 | Shapiro et al. |
| 6,612,984 B1 | 9/2003 | Kerr |
| 6,613,379 B2 * | 9/2003 | Ward et al. .................. 427/2.11 |
| 6,618,603 B2 | 9/2003 | Varalli et al. |
| 6,618,934 B1 | 9/2003 | Feldman et al. |
| 6,633,772 B2 | 10/2003 | Ford et al. |
| 6,642,015 B2 | 11/2003 | Vachon et al. |
| 6,645,181 B1 | 11/2003 | Lavi et al. |
| 6,654,625 B1 | 11/2003 | Say et al. |
| 6,656,157 B1 | 12/2003 | Duchon et al. |
| 6,673,596 B1 | 1/2004 | Sayler et al. |
| 6,679,865 B2 | 1/2004 | Shekalim |
| 6,684,904 B2 | 2/2004 | Ito |
| 6,685,668 B1 | 2/2004 | Cho et al. |
| 6,689,089 B1 | 2/2004 | Tiedtke et al. |
| 6,689,265 B2 | 2/2004 | Heller et al. |
| 6,695,860 B1 | 2/2004 | Ward et al. |
| 6,699,383 B2 | 3/2004 | Lemire et al. |
| 6,702,249 B2 | 3/2004 | Ito |
| 6,702,857 B2 | 3/2004 | Brauker et al. |
| 6,702,972 B1 | 3/2004 | Markle |
| 6,705,833 B2 | 3/2004 | Tam et al. |
| 6,711,424 B1 | 3/2004 | Fine et al. |
| 6,712,796 B2 | 3/2004 | Fentis et al. |
| 6,721,587 B2 | 4/2004 | Gough |
| 6,723,086 B2 | 4/2004 | Bassuk et al. |
| 6,730,200 B1 | 5/2004 | Stewart et al. |
| 6,733,655 B1 | 5/2004 | Davies et al. |
| 6,736,783 B2 | 5/2004 | Blake et al. |
| 6,737,158 B1 | 5/2004 | Thompson |
| 6,741,877 B1 | 5/2004 | Shults et al. |
| 6,742,635 B2 | 6/2004 | Neel et al. |
| 6,749,587 B2 | 6/2004 | Flaherty |
| 6,770,030 B1 | 8/2004 | Schaupp et al. |
| 6,770,067 B2 | 8/2004 | Lorenzen et al. |
| 6,773,565 B2 | 8/2004 | Kunimoto et al. |
| 6,780,297 B2 | 8/2004 | Matsumoto et al. |
| 6,801,041 B2 | 10/2004 | Karinka et al. |
| 6,802,957 B2 | 10/2004 | Jung et al. |
| 6,804,002 B2 | 10/2004 | Fine et al. |
| 6,805,693 B2 | 10/2004 | Gray et al. |
| 6,809,653 B1 | 10/2004 | Mann et al. |
| 6,811,548 B2 | 11/2004 | Jeffrey |
| 6,815,186 B2 | 11/2004 | Clark, Jr. |
| 6,850,790 B2 | 2/2005 | Berner et al. |
| 6,858,020 B2 | 2/2005 | Rusnak |
| 6,862,465 B2 | 3/2005 | Shults et al. |
| 6,869,413 B2 | 3/2005 | Langley et al. |
| 6,875,386 B1 | 4/2005 | Ward et al. |
| 6,887,228 B2 | 5/2005 | Mckay |
| 6,891,317 B2 | 5/2005 | Pei et al. |
| 6,893,552 B1 | 5/2005 | Wang et al. |
| 6,895,263 B2 | 5/2005 | Shin et al. |
| 6,895,265 B2 | 5/2005 | Silver |
| 6,902,544 B2 | 6/2005 | Ludin et al. |
| 6,926,691 B2 | 8/2005 | Miethke |
| 6,931,327 B2 | 8/2005 | Goode et al. |
| 6,932,584 B2 | 8/2005 | Gray et al. |
| 6,936,006 B2 | 8/2005 | Sabra |
| 6,945,965 B2 | 9/2005 | Whiting |
| 6,948,492 B2 | 9/2005 | Wermeling et al. |
| 6,954,662 B2 | 10/2005 | Freger et al. |
| 6,960,192 B1 | 11/2005 | Flaherty et al. |
| 6,965,791 B1 * | 11/2005 | Hitchcock et al. ........... 600/345 |
| 6,966,325 B2 | 11/2005 | Erickson |
| 6,972,080 B1 | 12/2005 | Tomioka et al. |
| 6,975,893 B2 | 12/2005 | Say et al. |
| 6,979,315 B2 | 12/2005 | Rogers et al. |
| 6,989,891 B2 | 1/2006 | Braig et al. |
| 6,997,921 B2 | 2/2006 | Gray et al. |
| 6,998,247 B2 | 2/2006 | Monfre et al. |
| 7,003,336 B2 | 2/2006 | Holker et al. |
| 7,003,341 B2 | 2/2006 | Say et al. |
| 7,011,630 B2 | 3/2006 | Desai et al. |
| 7,022,219 B2 | 4/2006 | Mansouri et al. |
| 7,025,743 B2 | 4/2006 | Mann et al. |
| 7,048,727 B1 | 5/2006 | Moss |

| | | | | | | |
|---|---|---|---|---|---|---|
| 7,058,437 | B2 | 6/2006 | Buse et al. | 7,599,726 B2 | 10/2009 | Goode, Jr. et al. |
| 7,060,059 | B2 | 6/2006 | Keith et al. | 7,615,007 B2 | 11/2009 | Shults et al. |
| 7,061,593 | B2 | 6/2006 | Braig et al. | 7,637,868 B2 | 12/2009 | Saint et al. |
| 7,063,086 | B2 | 6/2006 | Shahbazpour et al. | 7,640,048 B2 | 12/2009 | Dobbles et al. |
| 7,066,884 | B2 | 6/2006 | Custer et al. | 7,654,956 B2 | 2/2010 | Brister et al. |
| 7,070,577 | B1 | 7/2006 | Haller et al. | 7,657,297 B2 | 2/2010 | Simpson et al. |
| 7,070,580 | B2 | 7/2006 | Nielsen | 2001/0016682 A1 | 8/2001 | Berner et al. |
| 7,074,307 | B2 | 7/2006 | Simpson et al. | 2001/0039053 A1 | 11/2001 | Liseo et al. |
| 7,078,582 | B2 | 7/2006 | Stebbings et al. | 2001/0041830 A1 | 11/2001 | Varalli et al. |
| 7,097,775 | B2 | 8/2006 | Greenberg et al. | 2002/0016535 A1 | 2/2002 | Martin et al. |
| 7,098,803 | B2 | 8/2006 | Mann et al. | 2002/0019022 A1 | 2/2002 | Dunn et al. |
| 7,100,628 | B1 | 9/2006 | Izenson et al. | 2002/0022883 A1 | 2/2002 | Burg |
| 7,115,884 | B1 | 10/2006 | Walt et al. | 2002/0023852 A1 | 2/2002 | McIvor et al. |
| 7,120,483 | B2 | 10/2006 | Russell et al. | 2002/0026111 A1 | 2/2002 | Ackerman |
| 7,131,967 | B2 | 11/2006 | Gray et al. | 2002/0042090 A1 | 4/2002 | Heller et al. |
| 7,134,999 | B2 | 11/2006 | Brauker et al. | 2002/0042561 A1 | 4/2002 | Schulman et al. |
| 7,136,689 | B2 | 11/2006 | Shults et al. | 2002/0045808 A1 | 4/2002 | Ford et al. |
| 7,146,202 | B2 | 12/2006 | Ward et al. | 2002/0055673 A1 | 5/2002 | Van Antwerp et al. |
| 7,150,741 | B2 | 12/2006 | Erickson et al. | 2002/0065453 A1 | 5/2002 | Lesho et al. |
| 7,153,265 | B2 | 12/2006 | Vachon | 2002/0068860 A1 | 6/2002 | Clark, Jr. |
| 7,162,290 | B1 | 1/2007 | Levin | 2002/0071776 A1 | 6/2002 | Bandis et al. |
| 7,168,597 | B1 | 1/2007 | Jones et al. | 2002/0084196 A1 | 7/2002 | Liamos et al. |
| 7,184,810 | B2 | 2/2007 | Caduff et al. | 2002/0099997 A1 | 7/2002 | Piret |
| 7,190,988 | B2 | 3/2007 | Say et al. | 2002/0111547 A1 | 8/2002 | Knobbe et al. |
| 7,207,968 | B1 | 4/2007 | Harcinske | 2002/0119711 A1 | 8/2002 | Van Antwerp et al. |
| 7,207,974 | B2 | 4/2007 | Safabash et al. | 2002/0151796 A1 | 10/2002 | Koulik |
| 7,211,074 | B2 | 5/2007 | Sansoucy | 2002/0155615 A1 | 10/2002 | Novikov et al. |
| 7,221,970 | B2 | 5/2007 | Parker | 2002/0161288 A1 | 10/2002 | Shin et al. |
| 7,223,253 | B2 | 5/2007 | Hogendijk | 2002/0169369 A1 | 11/2002 | Ward et al. |
| 7,225,535 | B2 | 6/2007 | Feldman et al. | 2002/0177763 A1 | 11/2002 | Burns et al. |
| 7,228,162 | B2 | 6/2007 | Ward et al. | 2002/0182241 A1 | 12/2002 | Boerenstein et al. |
| 7,238,165 | B2 | 7/2007 | Vincent et al. | 2002/0188185 A1 | 12/2002 | Sohrab |
| 7,247,138 | B2 | 7/2007 | Reghabi et al. | 2002/0193885 A1 | 12/2002 | Legeay et al. |
| 7,254,450 | B2 | 8/2007 | Christopherson et al. | 2002/0198513 A1 | 12/2002 | Lebel et al. |
| 7,255,690 | B2 | 8/2007 | Gray et al. | 2003/0006669 A1 | 1/2003 | Pei et al. |
| 7,258,681 | B2 | 8/2007 | Houde | 2003/0023171 A1 | 1/2003 | Sato et al. |
| 7,266,400 | B2 | 9/2007 | Fine et al. | 2003/0023317 A1 | 1/2003 | Brauker et al. |
| 7,267,665 | B2 | 9/2007 | Steil et al. | 2003/0028089 A1 | 2/2003 | Galley et al. |
| 7,276,029 | B2 | 10/2007 | Goode et al. | 2003/0032874 A1 | 2/2003 | Rhodes et al. |
| 7,288,085 | B2 | 10/2007 | Olsen | 2003/0036773 A1 | 2/2003 | Whitehurst et al. |
| 7,295,867 | B2 | 11/2007 | Berner et al. | 2003/0050546 A1 | 3/2003 | Desai et al. |
| 7,310,544 | B2 | 12/2007 | Brister et al. | 2003/0065254 A1 | 4/2003 | Schulman et al. |
| 7,311,690 | B2 | 12/2007 | Burnett | 2003/0070548 A1 | 4/2003 | Clausen |
| 7,313,425 | B2 | 12/2007 | Finarov et al. | 2003/0076082 A1 | 4/2003 | Morgan et al. |
| 7,314,452 | B2 | 1/2008 | Madonia | 2003/0078481 A1 | 4/2003 | McIvor et al. |
| 7,315,767 | B2 | 1/2008 | Caduff et al. | 2003/0078560 A1 | 4/2003 | Miller et al. |
| 7,316,662 | B2 | 1/2008 | Delnevo et al. | 2003/0097082 A1 | 5/2003 | Purdy et al. |
| 7,317,939 | B2 | 1/2008 | Fine et al. | 2003/0100821 A1 | 5/2003 | Heller et al. |
| 7,318,814 | B2 | 1/2008 | Levine et al. | 2003/0125612 A1 | 7/2003 | Fox et al. |
| 7,327,273 | B2 | 2/2008 | Hung et al. | 2003/0125613 A1 | 7/2003 | Enegren et al. |
| 7,329,234 | B2 | 2/2008 | Sansoucy | 2003/0130616 A1 | 7/2003 | Steil et al. |
| 7,334,594 | B2 | 2/2008 | Ludin | 2003/0134347 A1 | 7/2003 | Heller et al. |
| 7,335,179 | B2 | 2/2008 | Burnett | 2003/0143746 A1 | 7/2003 | Sage |
| 7,335,195 | B2 | 2/2008 | Mehier | 2003/0153821 A1 | 8/2003 | Berner |
| 7,338,464 | B2 | 3/2008 | Blischak et al. | 2003/0181794 A1 | 9/2003 | Rini et al. |
| 7,344,499 | B1 | 3/2008 | Prausnitz et al. | 2003/0187338 A1 | 10/2003 | Say et al. |
| 7,354,420 | B2 | 4/2008 | Steil et al. | 2003/0188427 A1 | 10/2003 | Say et al. |
| 7,361,155 | B2 | 4/2008 | Sage et al. | 2003/0203498 A1 | 10/2003 | Neel et al. |
| 7,364,562 | B2 | 4/2008 | Braig et al. | 2003/0211625 A1 | 11/2003 | Cohan et al. |
| 7,366,556 | B2 | 4/2008 | Brister et al. | 2003/0212346 A1 | 11/2003 | Yuzhakov et al. |
| 7,367,942 | B2 | 5/2008 | Grage et al. | 2003/0212347 A1 | 11/2003 | Sohrab |
| 7,381,184 | B2 | 6/2008 | Funderburk et al. | 2003/0235817 A1 | 12/2003 | Bartkowiak et al. |
| 7,396,353 | B2 | 7/2008 | Lorenzen et al. | 2004/0011671 A1 | 1/2004 | Shults et al. |
| 7,399,277 | B2 | 7/2008 | Saidara et al. | 2004/0015134 A1 | 1/2004 | Lavi et al. |
| 7,402,153 | B2 | 7/2008 | Steil et al. | 2004/0024327 A1 | 2/2004 | Brodnick |
| 7,417,164 | B2 | 8/2008 | Suri | 2004/0030285 A1 | 2/2004 | Lavi et al. |
| 7,424,318 | B2 | 9/2008 | Brister et al. | 2004/0039298 A1 | 2/2004 | Abreu |
| 7,460,898 | B2 | 12/2008 | Brister et al. | 2004/0045879 A1 | 3/2004 | Shults et al. |
| 7,467,003 | B2 | 12/2008 | Brister et al. | 2004/0054352 A1 | 3/2004 | Adames et al. |
| 7,471,972 | B2 | 12/2008 | Rhodes et al. | 2004/0068230 A1 | 4/2004 | Estes et al. |
| 7,525,298 | B2 | 4/2009 | Morgan et al. | 2004/0074785 A1 | 4/2004 | Holker et al. |
| 7,583,990 | B2 | 9/2009 | Goode, Jr. et al. | 2004/0078219 A1 | 4/2004 | Kaylor et al. |
| 7,591,801 | B2 | 9/2009 | Brauker et al. | 2004/0106857 A1 | 6/2004 | Gough |

| | | | | | | |
|---|---|---|---|---|---|---|
| 2004/0106859 A1 | 6/2004 | Say et al. | | 2006/0036140 A1 | 2/2006 | Brister et al. |
| 2004/0133131 A1 | 7/2004 | Kuhn et al. | | 2006/0036141 A1 | 2/2006 | Kamath et al. |
| 2004/0133164 A1 | 7/2004 | Funderburk et al. | | 2006/0036142 A1 | 2/2006 | Brister et al. |
| 2004/0152187 A1 | 8/2004 | Haight et al. | | 2006/0036143 A1 | 2/2006 | Brister et al. |
| 2004/0152622 A1 | 8/2004 | Keith et al. | | 2006/0036144 A1 | 2/2006 | Brister et al. |
| 2004/0167801 A1 | 8/2004 | Say et al. | | 2006/0036145 A1 | 2/2006 | Brister et al. |
| 2004/0173472 A1 | 9/2004 | Jung et al. | | 2006/0040402 A1 | 2/2006 | Brauker et al. |
| 2004/0186362 A1 | 9/2004 | Brauker et al. | | 2006/0052745 A1 | 3/2006 | Van Antwerp et al. |
| 2004/0186365 A1 | 9/2004 | Jin et al. | | 2006/0079809 A1 | 4/2006 | Goldberger et al. |
| 2004/0193025 A1 | 9/2004 | Steil et al. | | 2006/0094946 A1 | 5/2006 | Kellogg et al. |
| 2004/0199059 A1 | 10/2004 | Brauker et al. | | 2006/0155180 A1 | 7/2006 | Brister et al. |
| 2004/0204687 A1 | 10/2004 | Mogensen | | 2006/0183984 A1 | 8/2006 | Dobbles et al. |
| 2004/0236200 A1 | 11/2004 | Say et al. | | 2006/0183985 A1 | 8/2006 | Brister et al. |
| 2004/0236251 A1 | 11/2004 | Roe et al. | | 2006/0189856 A1 | 8/2006 | Petisce et al. |
| 2004/0242982 A1 | 12/2004 | Sakata et al. | | 2006/0189863 A1 | 8/2006 | Peyser et al. |
| 2004/0254433 A1 | 12/2004 | Bandis et al. | | 2006/0195029 A1 | 8/2006 | Shults et al. |
| 2005/0010265 A1 | 1/2005 | Baru Fassio et al. | | 2006/0200020 A1 | 9/2006 | Brister et al. |
| 2005/0027180 A1 | 2/2005 | Goode et al. | | 2006/0222566 A1 | 10/2006 | Brauker et al. |
| 2005/0027181 A1 | 2/2005 | Goode et al. | | 2006/0224141 A1 | 10/2006 | Rush et al. |
| 2005/0027462 A1 | 2/2005 | Goode et al. | | 2006/0235285 A1 | 10/2006 | Brister et al. |
| 2005/0027463 A1 | 2/2005 | Goode et al. | | 2006/0253085 A1 | 11/2006 | Geismar et al. |
| 2005/0031689 A1 | 2/2005 | Shults et al. | | 2006/0258761 A1 | 11/2006 | Boock et al. |
| 2005/0033132 A1 | 2/2005 | Shults et al. | | 2006/0258929 A1 | 11/2006 | Goode et al. |
| 2005/0038332 A1 | 2/2005 | Saidara et al. | | 2006/0263839 A1 | 11/2006 | Ward et al. |
| 2005/0043598 A1 | 2/2005 | Goode et al. | | 2006/0270922 A1 | 11/2006 | Brauker et al. |
| 2005/0051427 A1 | 3/2005 | Brauker et al. | | 2006/0270923 A1 | 11/2006 | Brauker et al. |
| 2005/0051440 A1 | 3/2005 | Simpson et al. | | 2007/0016381 A1 | 1/2007 | Kamath et al. |
| 2005/0054909 A1 | 3/2005 | Petisce et al. | | 2007/0017805 A1 | 1/2007 | Hodges et al. |
| 2005/0056551 A1 | 3/2005 | White et al. | | 2007/0027384 A1 | 2/2007 | Brister et al. |
| 2005/0056552 A1 | 3/2005 | Simpson et al. | | 2007/0027385 A1 | 2/2007 | Brister et al. |
| 2005/0065464 A1 | 3/2005 | Talbot et al. | | 2007/0032706 A1 | 2/2007 | Kamath et al. |
| 2005/0090607 A1 | 4/2005 | Tapsak et al. | | 2007/0032717 A1 | 2/2007 | Brister et al. |
| 2005/0103625 A1 | 5/2005 | Rhodes et al. | | 2007/0038044 A1 | 2/2007 | Dobbles et al. |
| 2005/0112169 A1 | 5/2005 | Brauker et al. | | 2007/0045902 A1 | 3/2007 | Brauker et al. |
| 2005/0113653 A1 | 5/2005 | Fox et al. | | 2007/0049873 A1 | 3/2007 | Hansen et al. |
| 2005/0115832 A1 | 6/2005 | Simpson et al. | | 2007/0066873 A1 | 3/2007 | Kamath et al. |
| 2005/0121322 A1 | 6/2005 | Say | | 2007/0085995 A1 | 4/2007 | Pesach et al. |
| 2005/0124873 A1 | 6/2005 | Shults et al. | | 2007/0093704 A1 | 4/2007 | Brister et al. |
| 2005/0131305 A1 | 6/2005 | Danielson et al. | | 2007/0129619 A1 | 6/2007 | Ward et al. |
| 2005/0133368 A1 | 6/2005 | Davies et al. | | 2007/0129621 A1 | 6/2007 | Kellogg et al. |
| 2005/0139489 A1 | 6/2005 | Oliver et al. | | 2007/0135699 A1 | 6/2007 | Ward et al. |
| 2005/0143635 A1 | 6/2005 | Kamath et al. | | 2007/0151869 A1 | 7/2007 | Heller et al. |
| 2005/0143675 A1 | 6/2005 | Neel et al. | | 2007/0173706 A1 | 7/2007 | Neinast et al. |
| 2005/0154271 A1* | 7/2005 | Rasdal et al. ............... 600/347 | | 2007/0173711 A1 | 7/2007 | Shah et al. |
| 2005/0176136 A1 | 8/2005 | Burd et al. | | 2007/0197889 A1 | 8/2007 | Brister et al. |
| 2005/0177036 A1 | 8/2005 | Shults et al. | | 2007/0203407 A1 | 8/2007 | Hoss et al. |
| 2005/0181012 A1 | 8/2005 | Saint et al. | | 2007/0203410 A1 | 8/2007 | Say et al. |
| 2005/0182451 A1 | 8/2005 | Griffin et al. | | 2007/0203966 A1 | 8/2007 | Brauker et al. |
| 2005/0183954 A1 | 8/2005 | Hitchcock et al. | | 2007/0206193 A1 | 9/2007 | Pesach |
| 2005/0187720 A1 | 8/2005 | Goode et al. | | 2007/0208244 A1 | 9/2007 | Brauker et al. |
| 2005/0192557 A1 | 9/2005 | Brauker et al. | | 2007/0208245 A1 | 9/2007 | Brauker et al. |
| 2005/0203360 A1 | 9/2005 | Brauker et al. | | 2007/0208246 A1 | 9/2007 | Brauker et al. |
| 2005/0215871 A1 | 9/2005 | Feldman et al. | | 2007/0213611 A1 | 9/2007 | Simpson et al. |
| 2005/0215872 A1 | 9/2005 | Berner et al. | | 2007/0218097 A1 | 9/2007 | Heller et al. |
| 2005/0239154 A1 | 10/2005 | Feldman et al. | | 2007/0225675 A1 | 9/2007 | Robinson et al. |
| 2005/0242479 A1 | 11/2005 | Petisce et al. | | 2007/0232879 A1 | 10/2007 | Brister et al. |
| 2005/0245795 A1 | 11/2005 | Goode et al. | | 2007/0235331 A1 | 10/2007 | Simpson et al. |
| 2005/0245799 A1 | 11/2005 | Brauker et al. | | 2007/0240497 A1 | 10/2007 | Robinson et al. |
| 2005/0258037 A1 | 11/2005 | Hajizadeh et al. | | 2007/0244381 A1 | 10/2007 | Robinson et al. |
| 2005/0261563 A1 | 11/2005 | Zhou et al. | | 2007/0244382 A1 | 10/2007 | Robinson et al. |
| 2005/0272989 A1 | 12/2005 | Shah et al. | | 2007/0249916 A1 | 10/2007 | Pesach et al. |
| 2005/0288596 A1 | 12/2005 | Eigler et al. | | 2008/0021666 A1 | 1/2008 | Goode et al. |
| 2006/0015020 A1 | 1/2006 | Neale et al. | | 2008/0029391 A1 | 2/2008 | Mao et al. |
| 2006/0016700 A1 | 1/2006 | Brister et al. | | 2008/0071157 A1 | 3/2008 | McGarraugh et al. |
| 2006/0019327 A1 | 1/2006 | Brister et al. | | 2008/0071158 A1 | 3/2008 | McGarraugh et al. |
| 2006/0020186 A1 | 1/2006 | Brister et al. | | 2008/0072663 A1 | 3/2008 | Keenan et al. |
| 2006/0020187 A1 | 1/2006 | Brister et al. | | 2008/0086040 A1 | 4/2008 | Heller et al. |
| 2006/0020188 A1 | 1/2006 | Kamath et al. | | 2008/0086041 A1 | 4/2008 | Heller et al. |
| 2006/0020189 A1 | 1/2006 | Brister et al. | | 2008/0086042 A1 | 4/2008 | Brister et al. |
| 2006/0020190 A1 | 1/2006 | Kamath et al. | | 2008/0086043 A1 | 4/2008 | Heller et al. |
| 2006/0020191 A1 | 1/2006 | Brister et al. | | 2008/0086044 A1 | 4/2008 | Brister et al. |
| 2006/0020192 A1 | 1/2006 | Brister et al. | | 2008/0086273 A1 | 4/2008 | Shults et al. |
| 2006/0036139 A1 | 2/2006 | Brister et al. | | 2008/0091094 A1 | 4/2008 | Heller et al. |

| | | | |
|---|---|---|---|
| 2008/0091095 A1 | 4/2008 | Heller et al. | |
| 2008/0108942 A1 | 5/2008 | Brister et al. | |
| 2008/0119703 A1 | 5/2008 | Brister et al. | |
| 2008/0119704 A1 | 5/2008 | Brister et al. | |
| 2008/0119706 A1 | 5/2008 | Brister et al. | |
| 2008/0154101 A1 | 6/2008 | Goode et al. | |
| 2008/0183061 A1 | 7/2008 | Goode et al. | |
| 2008/0183399 A1 | 7/2008 | Goode et al. | |
| 2008/0187655 A1 | 8/2008 | Markle et al. | |
| 2008/0188722 A1 | 8/2008 | Markle et al. | |
| 2008/0188725 A1 | 8/2008 | Markle et al. | |
| 2008/0188731 A1 | 8/2008 | Brister et al. | |
| 2008/0189051 A1 | 8/2008 | Goode et al. | |
| 2008/0193936 A1 | 8/2008 | Goode et al. | |
| 2008/0194837 A1 | 8/2008 | Goode et al. | |
| 2008/0194935 A1 | 8/2008 | Brister et al. | |
| 2008/0194937 A1 | 8/2008 | Goode et al. | |
| 2008/0195967 A1 | 8/2008 | Goode et al. | |
| 2008/0197024 A1 | 8/2008 | Simpson et al. | |
| 2008/0200788 A1 | 8/2008 | Brister et al. | |
| 2008/0200789 A1 | 8/2008 | Brister et al. | |
| 2008/0200791 A1 | 8/2008 | Simpson et al. | |
| 2008/0208025 A1 | 8/2008 | Shults et al. | |
| 2008/0214915 A1 | 9/2008 | Brister et al. | |
| 2008/0262469 A1 | 10/2008 | Brister et al. | |
| 2008/0287764 A1 | 11/2008 | Rasdal et al. | |
| 2008/0287765 A1 | 11/2008 | Rasdal et al. | |
| 2008/0287766 A1 | 11/2008 | Rasdal et al. | |
| 2008/0296155 A1 | 12/2008 | Shults et al. | |
| 2008/0305009 A1 | 12/2008 | Gamsey et al. | |
| 2008/0305506 A1 | 12/2008 | Suri | |
| 2008/0306368 A1 | 12/2008 | Goode et al. | |
| 2009/0018418 A1 | 1/2009 | Markle et al. | |
| 2009/0018426 A1 | 1/2009 | Markle et al. | |
| 2009/0061528 A1 | 3/2009 | Suri | |
| 2009/0081803 A1 | 3/2009 | Gamsey et al. | |
| 2009/0099434 A1 | 4/2009 | Liu et al. | |
| 2009/0177143 A1 | 7/2009 | Markle et al. | |
| 2009/0178459 A1 | 7/2009 | Li et al. | |
| 2009/0182217 A1 | 7/2009 | Li et al. | |
| 2009/0192366 A1 | 7/2009 | Mensinger et al. | |
| 2009/0192380 A1 | 7/2009 | Shariati et al. | |
| 2009/0192722 A1 | 7/2009 | Shariati et al. | |
| 2009/0192724 A1 | 7/2009 | Brauker et al. | |
| 2009/0192745 A1 | 7/2009 | Kamath et al. | |
| 2009/0192751 A1 | 7/2009 | Kamath et al. | |
| 2009/0203981 A1 | 8/2009 | Brauker et al. | |
| 2009/0204341 A1 | 8/2009 | Brauker et al. | |
| 2009/0216103 A1 | 8/2009 | Brister et al. | |
| 2009/0240120 A1 | 9/2009 | Mensinger et al. | |
| 2009/0240128 A1 | 9/2009 | Mensinger et al. | |
| 2009/0240193 A1 | 9/2009 | Mensinger et al. | |
| 2009/0242399 A1 | 10/2009 | Kamath et al. | |
| 2009/0242425 A1 | 10/2009 | Kamath et al. | |
| 2009/0264719 A1 | 10/2009 | Markle et al. | |
| 2009/0287074 A1 | 11/2009 | Shults et al. | |
| 2009/0299162 A1 | 12/2009 | Brauker et al. | |
| 2009/0299276 A1 | 12/2009 | Brauker et al. | |
| 2010/0010324 A1 | 1/2010 | Brauker et al. | |
| 2010/0010331 A1 | 1/2010 | Brauker et al. | |
| 2010/0010332 A1 | 1/2010 | Brauker et al. | |
| 2010/0016687 A1 | 1/2010 | Brauker et al. | |
| 2010/0022855 A1 | 1/2010 | Brauker et al. | |
| 2010/0030053 A1 | 2/2010 | Goode, Jr. et al. | |
| 2010/0030484 A1 | 2/2010 | Brauker et al. | |
| 2010/0036215 A1 | 2/2010 | Goode, Jr. et al. | |
| 2010/0036216 A1 | 2/2010 | Goode, Jr. et al. | |
| 2010/0036222 A1 | 2/2010 | Goode, Jr. et al. | |
| 2010/0036223 A1 | 2/2010 | Goode, Jr. et al. | |
| 2010/0036224 A1 | 2/2010 | Goode, Jr. et al. | |
| 2010/0036225 A1 | 2/2010 | Goode, Jr. et al. | |
| 2010/0041971 A1 | 2/2010 | Goode, Jr. et al. | |
| 2010/0045465 A1 | 2/2010 | Brauker et al. | |
| 2010/0049024 A1 | 2/2010 | Saint et al. | |

FOREIGN PATENT DOCUMENTS

| | | |
|---|---|---|
| EP | 0 127 958 | 12/1984 |
| EP | 0 284 518 | 9/1988 |
| EP | 0 320 109 | 6/1989 |
| EP | 0 353 328 | 2/1990 |
| EP | 0 390 390 | 10/1990 |
| EP | 0 396 788 | 11/1990 |
| EP | 0 441 394 | 8/1991 |
| EP | 0 476 980 | 3/1992 |
| EP | 0 563 795 | 10/1993 |
| EP | 0 286 118 B1 | 1/1995 |
| EP | 0 776 628 A2 | 6/1997 |
| EP | 0 817 809 | 1/1998 |
| EP | 0 838 230 A | 4/1998 |
| EP | 0 880 936 | 12/1998 |
| EP | 0 885 932 | 12/1998 |
| EP | 0 967 788 | 12/1999 |
| EP | 1 077 634 | 2/2001 |
| EP | 1 078 258 | 2/2001 |
| EP | 1 266 607 | 12/2002 |
| FR | 2656423 | 6/1991 |
| FR | 2760962 | 9/1998 |
| GB | 1 442 303 | 7/1976 |
| GB | 2149918 | 6/1985 |
| JP | 62083649 | 4/1987 |
| JP | 02002913 | 1/1990 |
| JP | 3-293556 | 12/1991 |
| JP | 2002-189015 | 7/2002 |
| WO | WO 90/00738 | 1/1990 |
| WO | WO 90/10861 | 9/1990 |
| WO | WI 91/09302 | 6/1991 |
| WO | WO 91/16416 | 10/1991 |
| WO | WO 92/07525 | 5/1992 |
| WO | WO 92/13271 | 8/1992 |
| WO | WO 93/14693 | 8/1993 |
| WO | WO 93/19701 | 10/1993 |
| WO | WO 93/23744 | 11/1993 |
| WO | WO 94/22367 | 10/1994 |
| WO | WO 95/07109 | 3/1995 |
| WO | WO 96/01611 | 1/1996 |
| WO | WO 96/14026 | 5/1996 |
| WO | WO 96/25089 | 8/1996 |
| WO | WO 96/30431 | 10/1996 |
| WO | WO 96/32076 | 10/1996 |
| WO | WO 96/36296 | 11/1996 |
| WO | WO 97/01986 | 1/1997 |
| WO | WO 97/06727 | 2/1997 |
| WO | WO 97/28737 | 8/1997 |
| WO | WO 98/19159 | 5/1998 |
| WO | WO 98/24358 | 6/1998 |
| WO | WO 98/38906 | 9/1998 |
| WO | WO 99/56613 | 4/1999 |
| WO | WO 99/48419 | 9/1999 |
| WO | WO 99/58051 | 11/1999 |
| WO | WO 99/58973 | 11/1999 |
| WO | WO 00/19887 | 4/2000 |
| WO | WO 00/32098 | 6/2000 |
| WO | WO 00/33065 | 6/2000 |
| WO | WO 00/49940 | 8/2000 |
| WO | WO 00/59373 | 10/2000 |
| WO | WO 00/74753 | 12/2000 |
| WO | WO 01/12158 | 2/2001 |
| WO | WO 01/20019 A2 | 3/2001 |
| WO | WO 01/20334 A1 | 3/2001 |
| WO | WO 01/34243 | 5/2001 |
| WO | WO 01/43660 | 6/2001 |
| WO | WO 01/52727 | 7/2001 |
| WO | WO 01/58348 | 8/2001 |
| WO | WO 01/68901 | 9/2001 |
| WO | WO 01/69222 | 9/2001 |

| | | |
|---|---|---|
| WO | WO 01/88524 | 11/2001 |
| WO | WO 01/88534 | 11/2001 |
| WO | WO 02/24065 | 3/2002 |
| WO | WO 02/082989 | 10/2002 |
| WO | WO 03/082091 | 9/2003 |
| WO | WO 2005/012873 | 2/2005 |
| WO | WO 2005/057168 | 6/2005 |
| WO | WO 2005/057175 | 6/2005 |
| WO | WO 2006/017358 | 2/2006 |
| WO | WO 2007/002209 | 1/2007 |
| WO | WO 2008/001091 | 1/2008 |

OTHER PUBLICATIONS

Baker, et al. 1993. Dynamic concentration challenges for biosensor characterization. *Biosensors & Bioelectronics*, 8:433-441.

Bland, et al. 1990. A note on the use of the intraclass correlation coefficient in the evaluation of agreement between two methods of measurement. *Comput. Biol. Med.*, 20(5):337-340.

Bott, A. W. A Comparison of Cyclic Voltammetry and Cyclic Staircase Voltammetry. Current Separations 1997, 16:1, 23-26.

Brauker, et al. Sustained expression of high levels of human factor IX from human cells implanted within an immunoisolation device into athymic rodents. Hum Gene Ther 1998, 9, 879-888.

D'Arrigo, et al. Porous-Si based bioreactors for glucose monitoring and drugs production. Proc. of SPIE 2003, 4982, 178-184.

El-Sa'ad, L.; Yates, D. Moisture Absorption by Epoxy Resins: the Reverse Thermal Effect. Journal of Materials Science 1990, 25, 3577-3582.

Fare, et al. 1998. Functional characterization of a conducting polymer-based immunoassay system. *Biosensors & Bioelectronics*, 13(3-4):459-470.

Geller, et al. use of an immunoisolation device for cell transplantation and tumor immunotherapy. Ann NY Acad Sci 1997, 831, 438-451.

Gerritsen, et al. Influence of inflammatory cells and serum on the performance of implantable glucose sensors. J Biomed Mater Res 2001, 54, 69-75.

Hitchman, M. L. 1978. "Measurement of Dissolved Oxygen." In Elving, et al. (Eds.). Chemical Analysis, vol. 49, Chap. 3, pp. 34-49, 59-123. New York: John Wiley & Sons.

Jensen, et al. 1997. Fast wave forms for pulsed electrochemical detection of glucose by incorporation of reductive desorption of oxidation products. *Analytical Chemistry*, 69(9):1776-1781.

Kargol, et al. Studies on the structural properties of porous membranes: measurement of linear dimensions of solutes. Biophys Chem 2001, 91, 263-271.

Kurnik, et al. 1999. Application of the mixtures of experts algorithm for signal processing in a noninvasive glucose monitoring system. *Sensors and Actuators*, B 60:19-26.

Lee, et al. Effects of pore size, void volume, and pore connectivity on tissue responses to porous silicone implants. Society for Biomaterials 1999, 25th Annual Meeting, 171.

Makale, et al. 2003. Tissue window chamber system for validation of implanted oxygen sensors. *Am. J. Physiol. Heart Circ. Physiol.*, 284:H2288-2294.

Mancy, et al. 1962. A galvanic cell oxygen analyzer. *Journal of Electroanalytical Chemistry*, 4:65-92.

Miller, A. Human monocyte/macrophage activation and interleukin 1 generation by biomedical polymers. J Biomed Mater Res 1988, 23, 713-731.

Miller, et al. Generation of IL-1 like activity in response to biomedical polymer implants: a comparison of in vitro and in vivo models. J Biomed Mater Res 1989, 23, 1007-1026.

Miller, et al. In vitro stimulation of fibroblast activity by factors generated from human monocytes activated by biomedical polymers. Journal of J Biomed Mater Res 1989, 23, 911-930.

Mowery, et al. Preparation and characterization of hydrophobic polymeric films that are thromboresistant via nitric oxide release. Biomaterials 2000, 21, 9-21.

Nam, et al. A novel fabrication method of macroporous biodegradable polymer scaffolds using gas foaming salt as a porogen additive. J Biomed Mat Res 2000, 53, 1-7.

Okuda, J.; Miwa, I. Mutarotase effect on micro determinations of D-glucose and its anomers with -D-glucose oxidase. Anal Biochem 1971, 43, 312-315.

Ratner, B.D. Reducing capsular thickness and enhancing angiogenesis around implant drug release systems. J Control Release 2002, 78, 211-218.

Rhodes, et al. 1994. Prediction of pocket-portable and implantable glucose enzyme electrode performance from combined species permeability and digital simulation analysis. *Analytical Chemistry*, 66(9):1520-1529.

Schmidt, et al. 1993. Glucose concentration in subcutaneous extracellular space. *Diabetes Care*. 16(5):695-700.

Schmidtke, D. W.; Heller, A. Accuracy of the one-point in vivo calibration of "wired" glucose oxidase electrodes implanted in jugular veins of rats in periods of rapid rise and decline of the glucose concentration. Anal Chem 1998, 70, 2149-2155.

Sieminski, et al. Biomaterial-microvasculature interactions. Biomateials 2000, 21, 2233-2241.

Tang, et al. Fibrin(ogen) mediates acute inflammatory responses to biomaterials. J Exp Med 1993, 178, 2147-2156.

Tang, et al. Inflammatory responses to biomaterials. Am J Clin Pathol 1995, 103, 466-471.

Tang, et al. Mast cells mediates acute inflammatory responses to implanted biomaterials. Proc Natl Acad Sci U S A 1998, 95, 8841-8846.

Tang, et al. Molecular determinants of acute inflammatory responses to biomaterials. J Clin Invest 1996, 97, 1329-1334.

Tibell, et al. Survival of macroencapsulated allogeneic parathyroid tissue one year after transplantation in nonimmunosuppressed humans. Cell Transplant 2001, 10, 591-9.

Trajanoski, et al. 1998. Neural predictive controller for insulin delivery using the subcutaneous route. *IEEE Transactions on Biomedical Engineering*, 45(9):1122-1134.

Updike, et al. 1982. Implanting the glucose enzyme electrode: Problems, progress, and alternative solutions. *Diabetes Care*, 5(3):207-212.

Wu, et al. 1999. In situ electrochemical oxygen generation with an immunoisolation device. *Ann. N. Y. Acad. Sci.*, 875:105-125.

Wood, W., et al., Hermetic Sealing with Epoxy. Mechanical Engineering Mar. 1990, 1-3.

U.S. Appl. No. 10/838,658, filed May 3, 2004, (See Image File Wrapper).

U.S. Appl. No. 10/838,909, filed May 3, 2004, (See Image File Wrapper).

U.S. Appl. No. 10/838,912, filed May 3, 2004, (See Image File Wrapper).

U.S. Appl. No. 10/885,476, filed Jul. 6, 2004, (See Image File Wrapper).

U.S. Appl. No. 11/077,715, filed Mar. 10, 2005, (See Image File Wrapper).

U.S. Appl. No. 11/077,883, filed Mar. 10, 2005, (See Image File Wrapper).

U.S. Appl. No. 11/077,739, filed Mar. 10, 2005, (See Image File Wrapper).

U.S. Appl. No. 11/077,740, filed Mar. 10, 2005, (See Image File Wrapper).

U. S. Appl. No. 11/077,765, filed Mar. 10, 2005, (See Image File Wrapper).

U.S. Appl. No. 11/078,230, filed Mar. 10, 2005, (See Image File Wrapper).

U.S. Appl. No. 11/078,232, filed Mar. 10, 2005, (See Image File Wrapper).

U.S. Appl. No. 11/077,713, filed Mar. 10, 2005, (See Image File Wrapper).

U.S. Appl. No. 11/077,693, filed Mar. 10, 2005, (See Image File Wrapper).

U.S. Appl. No. 11/077,714, filed Mar. 10, 2005, (See Image File Wrapper).

U.S. Appl. No. 11/077,763, filed Mar. 10, 2005, (See Image File Wrapper).

U.S. Appl. No. 11/077,643, filed Mar. 10, 2005, (See Image File Wrapper).

U.S. Appl. No. 11/078,072, filed Mar. 10, 2005, (See Image File Wrapper).
U.S. Appl. No. 11/157,746, filed Jun. 21, 2005, (See Image File Wrapper).
U.S. Appl. No. 11/157,365, filed Jun. 21, 2005, (See Image File Wrapper).
U.S. Appl. No. 11/158,227, filed Jun. 21, 2005, (See Image File Wrapper).
U.S. Appl. No. 11/201,445, filed Aug. 10, 2005, (See Image File Wrapper).
International Search Report for related PCT application PCT/US2005/024994, mailed Nov. 15, 2005.
Written Opinion for related PCT application PCT/US2005/024994, mailed Nov. 15, 2005.
Armour, et al., *Application of Chronic Intravascular Blood Glucose Sensor in Dogs*, Diabetes, vol. 39, Dec. 1990 pp. 1519-1526.
Asberg, et al., *Hydrogels of a Conducting Conjugated Polymer as 3-D Enzyme Electrode*, Biosensors Bioelectronics, pp. 199-207 (2003).
Dai, et al., *Hydrogel Membranes with Mesh Size Asymmetry Based on the Gradient Crosslink of Poly(vinyl alcohol)*, Journal of Membrane Science 156 (1999) 67-79.
Fraser, et al. *Biosensors in the Body*, Continous in Vivo Monitoring, Wiley Series of Biomaterials Science and Engineering, 1997, Chapter 4, Principles of Long-term Fully Implantable Sensors with Emphasis on Radiotelemetric Monitoring of Blood Glucose from inside a Subcutaneous Foreign Body Capsule pp. 118-137.
Godsland, et al., *Maximizing the Success Rate of Minimal Model Insulin Sensivity Mearsurement in Humans: The Importance of Basal Glucose Levels*, , The Biochemical Society and the Medical Research Society, (2001) 1-9.
Gregg, et al. *Cross-Linked Redox Gels Containing Glucose Oxidase for Amperometric Biosensor Applications*, Anal. Chem. (1990) 62, 2568-263.
Heller, Adam, *Electrical Connection of Enzyme Redox Centers to Electrodes*, J. Phys. Chem. 1992, 96, pp. 3579-3587.
Luong, et al., *Solubilization of Multiwall Carbon Nanotubes by 3-Aminopropyltriethoxysilane Towards the Fabrication of Electrochemical Biosensors with Promoted Elecron Transfer*, Electroanalysis 16 No. 1-2, pp. 132-139. (2004).
McKean, et al. *A Telemetry Instrumentation System for Chronically Implanted Glucose and Oxygen Sensors*, Transactions on Biomedical Engineering vol. 35, No. 7 Jul. 1988 pp. 526-532.
Pickup, et al., *Responses adn Calibration of Amperometric Glucose Sensors Implanted in the Subcutaneous Tissue of Man*, ACTA Diabetol, pp. 143-148. (1993).
Sakakida, et al. *Ferrocene-Mediated Needle Type Glucose Sensor Covered with Newly Designed Biocompatible Membran*, Sensors and Actuators B, vol. 13-14, pp. 319-322 (1993).
Sakakida, et al. *Development of Ferrocene-Mediated Needle-Type Glucose Sensor as a Measure of True Subcutaneous Tissue Glucose Concentrations*, Artif. Organs Today, vol. 2 No. 2, pp. 145-158 (1992).
Shichiri, et al., *Membrane Design For Extending the Long-Life of an Implantable Glucose Sensor*, Diab. Nutr. Metab., 2, pp. 309-313 (1989).
Sternberg, et al. *Study and Development of Multilayer Needle-type Enzymebased Glucose Microsensors*, Biosensors vol. 4 pp. 27-40 (1988).
Shichiri, et al., *Telemetry Glucose Monitoring Device with Needle-Type Glucose Sensor: A Useful Tool for Blood Glucose Monitoring in Diabetic Individuals*, Diabetes Care, Inc. Vo. 9, No. 3, 1986 pp. 298-301.
Shichiri, et al., *Needle Type Glucose Sensor for Wearable Artificial Endocrine Pancreas*, Implantable Sensors for Closed-Loop Prosthetic Systems, Chapter 15, pp. 197-210.
Shichiri, et al. *Glycaemic Control in Pancreatectomized Dogs with a Wearable Artificial Endocrine Pancreas*, Diabetologia (1983) 24 pp. 179-184.
Thompson, et al., *In Vivo Probes: Problems and Perspectives*, Department of Chemistry, University of Toronto, Canada, pp. 255-261.

Velho, et al., *Strategies for Calibrating a Subcutaneous Glucose Sensor*, Biomed. Biochim. 48, 11/12, 957-964.
Wade Jr., L.G. *Organic Chemistry*, Chapter 17, Reactions of Aromatic Compounds pp. 762-763.
Wilson, et al., *Progress Toward the Development of an Implantable Sensor for Glucose*, Clinical Chemistry, vol. 38, No. 9, 1992 pp. 1613-1617.
Yang, et al., *A Comparison of Physical Properties and Fuel Cell Performance of Nafion and Zirconium Phosphate/Nafion Composite Membranes*, Journal Of Membrane Science 237 (2004) 145-161.
Shults, et al. *A Telemetry-Instrumentation System for Monitoring Multiple Subcutaneously Implanted Glucose Sensors*, Transactions on Biomedical Engineering vol. 41, No. 10 Oct. 1994. pp. 937-942.
U.S. Appl. No. 09/447,227, filed Nov. 22, 1999.
IPRP for PCT/US05/024994 filed Jul. 13, 2005.
Brooks, et al. "Development of an on-line glucose sensor for fermentation monitoring," Biosensors, 3:45-56 (1987/88).
Heller, "Electrical wiring of redox enzymes," Acc. Chem. Res., 23:128-134 (1990).
Kerner, et al. "The function of a hydrogen peroxide-detecting electroenzymatic glucose electrode is markedly impaired in human sub-cutaneous tissue and plasma," Biosensors & Bioelectronics, 8:473-482 (1993).
Koschinsky, et al. 1998. New approach to technical and clinical evaluation of devices for self-monitoring of blood glucose. Diabetes Care 11(8): 619-619.
Mastrototaro, et al. "An electroenzymatic glucose sensor fabricated on a flexible substrate," Sensors and Actuators B, 5:139-44 (1991).
Pickup, et al. "Implantable glucose sensors: choosing the appropriate sensor strategy," *Biosensors*, 3:335-346 (1987/88).
Pickup, et al. "In vivo molecular sensing in diabetes mellitus: an implantable glucose sensor with direct electron transfer," *Diabetologia*, 32:213-217 (1989).
Rebrin, et al. "Automated feedback control of subcutaneous glucsoe concentration in diabetic dogs," Diabetologia, 32:573-76 (1989).
Shaw, et al. "In vitro testing of a simply constructed, highly stable glucose sensor suitable for implantation in diabetic patients," Biosensors & Bioelectronics, 6:401-406 (1991).
Turner and Pickup, "Diabetes mellitus: biosensors for research and management," Biosensors, 1:85-115 (1985).
Wagner, et al. 1998. Continuous amperometric monitoring of glucose in a brittle diabetic chimpanzee with a miniature subcutaneous electrode. Proc. Natl. Acad. Sci. A, 95:6379-6382.
Office Action mailed May 18, 2007 in U.S. Appl. No. 11/543,707.
Office Action mailed May 23, 2007 in U.S. Appl. No. 11/543,539.
Office Action mailed May 18, 2007 in U.S. Appl. No. 11/543,683.
Office Action mailed Jun. 5, 2007 in U.S. Appl. No. 11/543,734.
Office Action dated Sep. 21, 2007 in U.S. Appl. No. 10/838,912.
Office Action dated Jul. 26, 2007 in U.S. Appl. No. 11/077,715.
Office Action dated Apr. 10, 2007 in U.S. Appl. No. 11/077,715.
Office Action dated Oct. 31, 2006 in U.S. Appl. No. 11/077,715.
Office Action dated Oct. 9, 2007 in U.S. Appl. No. 11/077,883.
Office Action dated Sep. 18, 2007 in U.S. Appl. No. 11/078,230.
Office Action dated Jul. 27, 2007 in U.S. Appl. No. 11/077,714.
Office Action dated Apr. 10, 2007 in U.S. Appl. No. 11/077,714.
Office Action dated Oct. 11, 2006 in U.S. Appl. No. 11/077,714.
Office Action dated Jan. 30, 2007 in U.S. Appl. No. 11/077,763.
Office Action dated Sep. 25, 2007 in U.S. Appl. No. 11/334,876.
Aussedat, et al. 1997. A user-friendly method for calibrating a subcutaneous glucose sensor-based hypoglycaemic alarm. Biosensors & Bioelectronics 12(11):1061-1071.
Bard et al. 1980. Electrochemical Methods. John Wiley & Sons, pp. 173-175.
Bland, et al. 1986. Statistical methods for assessing agreement between two methods of clinical measurement. Lancet 1:307-310.
Bode, B. W. 2000. Clinical utility of the continuous glucose monitoring system. Diabetes Technol Ther, 2(Suppl 1):S35-41.
Cass, et al. "Ferrocene-mediated enzyme electrodes for amperometric determination of glucose," Anal. Chem., 36:667-71 (1984).
Chia, C.W.; Saudek, C. D. 2004. Glucose sensors: toward closed loop insulin delivery. Endocrinol Metab Clin North Am 33:175-95.

Choleau, et al. 2002. Calibration of a subcutaneous amperometric glucose sensor implanted for 7 days in diabetic patients. Part 2. Superiority of the one-point calibration method. Biosensors and Bioelectronics 17:647-654.

Csöregi, et al. 1994. Amperometric microbiosensors for detection of hydrogen peroxide and glucose based on peroxidase-modified carbon fibers. Electroanalysis 6:925-933.

Edwards Lifesciences. Accuracy for your and your patients. Marketing materials, 4 pp. 2002.

Frost, et al. 2002. Implantable chemical sensors for real-time clinical monitoring: Progress and challenges. Current Opinion in Chemical Biology 6:633-641.

Guerci et al., Clincial performance of CGMS in type 1 diabetic patents treated by continuous subcutaneous insulin infusion using insulin analogs, Diabetes Care, 26:582-589, 2003.

Kiechle, F.L. 2001. The impact of continuous glucose monitoring on hospital point-of-care testing programs. Diabetes Technol Ther 3:647-649.

Lohn et al., A knowledge-based system for real-time validation of calibrations and measurements, Chemometrics and Intelligent Laboratory Systems, 1999 46, 57-66.

Martin, R. F. 2000. General Deming regression for estimating systematic bias and its confidence interval in method-comparison studies. Clinical Chemistry, 46(1):100-104.

Moatti-Sirat, D, et al. 1992. Evaluating in vitro and in vivo the interference of ascorbate and acetaminophen on glucose detection by a needle-type glucose sensor. Biosensors and Bioelectronics 7:345-352.

Moatti-Sirat et al., Reduction of acetaminophen interference in glucose sensors by a composite Nafion membrane: demonstration in rats and man, Diabetologia 37(6):610-616, Jun. 1994.

Pishko, et al. "Amperometric glucose microelectrodes prepared through immobilization of glucose oxidase in redox hydrogels," Anal. Chem., 63:2268-72 (1991).

Poitout, et al. 1993. A glucose monitoring system for on line estimation in man of blood glucose concentration using a miniaturized glucose sensor implanted in the subcutaneous tissue and a wearable control unit. Diabetologia 36:658-663.

Rinken, et al. 1998. Calibration of glucose biosensors by using pre-steady state kinetic data. Biosensors & Bioelectronics, 13:801-807.

Rivers et al., Central venous oxygen saturation monitoring in the critically ill patient, Current Opinion in Critical Care, 7:204-211, 2001.

Service, et al. 1970. Mean amplitude of glycemic excursions, a measure of diabetic instability. Diabetes, 19:644-655.

Skyler, J. S. 2000. The economic burden of diabetes and the benefits of improved glycemic control: The potential role fo a continuous glucose monitoring system. Diabetes Technology & Therapeutics 2 Suppl 1:S7-12.

Sokol et al. 1980, Immobilized-enzyme rate-determination method for glucose analysis, Clin. Chem. 26(1):89-92.

Tierney, M. J; Garg, S.; Ackerman, N. R.; Fermi, S. J.; Kennedy, J.; Lopatin, M.; Potts, R. O.; Tamada, J. A. 2000. Effect of acetaminophen on the accuracy of glucose measurements obtained with the GlucoWatch biographer. Diabetes Technol Ther 2:199-207.

Unger, et al. 2004. Glucose control in the hospitalized patient. Emerg Med 36(9):12-18.

Updike, et al. 1979. Continuous glucose monitor based on an immobilized enzyme electrode detector. J Lab Clin Med, 93(4):518-527.

Updike, et al. 1997. Principles of long-term fully impleated sensors with emphasis on radiotelemetric monitoring of blood glucose form inside a subcutaneous foreign body capsule (FBC). In Fraser, ed., Biosensors in the Body. New York. John Wiley & Sons, pp. 117-137.

Utah Medical Products Inc., Blood Pressure Tranducers product specifications. 6 pp. 2003-2006.

Van den Berghe 2004. Tight blood glucose control with insulin in "real-life" intensive care. Mayo Clin Proc 79(8):977-978.

Ward, et al. 1999. Assessment of chronically implanted subcutaneous glucose sensors in dogs: The effect of surrounding fluid masses. ASAIO Journal, 45:555-561.

Ward, et al. 2000. Rise in background current over time in a subcutaneous glucose sensor in the rabbit: Relevance to calibration and accuracy. Biosensors & Bioelectronics, 15:53-61.

Zamzow, et al. Development and evaluation of a wearable blood glucose monitor. pp. M588-M591, 1990.

Zhu, et al. 2002. Planar amperometric glucose sensor based on glucose oxidase immobilized by chitosan film on prussian blue layer. Sensors, 2:127-136.

Office Action dated Jun. 19, 2008 in U.S. Appl. No. 11/021,162.
Office Action dated Dec. 26, 2007 in U.S. Appl. No. 11/021,046.
Office Action dated Jun. 23, 2008 in U.S. Appl. No. 11/021,046.
Office Action dated Sep. 30, 2002 in U.S. Appl. No. 09/636,369.
Office Action dated Jul. 15, 2008 in U.S. Appl. No. 10/633,367.
Office Action dated May 22, 2006 in U.S. Appl. No. 10/896,772.
Office Action dated Dec. 14, 2005 in U.S. Appl. No. 10/896,772.
Office Action dated Jul. 19, 2005 in U.S. Appl. No. 10/896,772.
Office Action dated Jan. 11, 2005 in U.S. Appl. No. 10/896,772.
Office Action dated Dec. 21, 2004 in U.S. Appl. No. 10/632,537.
Office Action dated Oct. 20, 2004 in U.S. Appl. No. 10/632,537.
Office Action dated May 29, 2008 in U.S. Appl. No. 95/001,039.
Office Action dated Jun. 17, 2008 in U.S. Appl. No. 11/038,340.
Office Action dated Feb. 12, 2007 in U.S. Appl. No. 10/633,404.
Office Action dated Jun. 17, 2008 in U.S. Appl. No. 95/001,038.
Office Action dated Jun. 12, 2008 in U.S. Appl. No. 10/633,329.
Office Action dated Feb. 4, 2008 in U.S. Appl. No. 10/633,329.
Office Action dated Jul. 30, 2007 in U.S. Appl. No. 10/633,329.
Office Action dated Mar. 26, 2007 in U.S. Appl. No. 10/633,329.
Office Action dated Oct. 5, 2006 in U.S. Appl. No. 10/633,329.
Office Action dated Jun. 24, 2008 n U.S. Appl. No. 11/007,920.
Office Action dated Nov. 28, 2007 in U.S. Appl. No. 10/991,966.
Office Action dated Jul. 22, 2008 in U.S. Appl. No. 10/991,966.
Office Action dated Nov. 27, 2006 in U.S. Appl. No. 10/789,359.
Office Action dated Mar. 20, 2008 in U.S. Appl. No. 10/789,359.
Office Action dated Dec. 12, 2007 in U.S. Appl. No. 11/543,707.
Office Action mailed Dec. 12, 2007 in U.S. Appl. No. 11/543,539.
Office Action mailed Dec. 12, 2007 in U.S. Appl. No. 11/543,683.
Office action mailed Dec. 17, 2007 in U.S. Appl. No. 11/543,734.
Office Action dated Jan. 15, 2008 in U.S. Appl. No. 11/034,344.
Office Action dated Nov. 1, 2007 in U.S. Appl. No. 11/034,343.
Office Action dated Jul. 10, 2008 in U.S. Appl. No. 11/034,343.
Office Action in U.S. Appl. No. 10/838,909 mailed Jun. 5, 2008.
Office Action dated May 12, 2008 in U.S. Appl. No. 11/077,715.
Office Action dated Jan. 28, 2008 in U.S. Appl. No. 11/077,715.
Office Action dated Jun. 1, 2007 in U.S. Appl. No. 11/077,740.
Office Action dated Nov. 1, 2007 in U.S. Appl. No. 11/077,740.
Office Action dated Feb. 7, 2008 in U.S. Appl. No. 11/077,740.
Office Action dated Jul. 25, 2008 in U.S. Appl. No. 11/077,740.
Office Action dated Dec. 31, 2007 in U.S. Appl. No. 11/077,765.
Office Action dated May 16, 2008 in U.S. Appl. No. 11/077,765.
Office Action dated Jun. 30, 2008 in U.S. Appl. No. 11/078,230.
Office Action dated Sep. 5, 2008 in U.S. Appl. No. 11/078,230.
Office Action dated May 5, 2008 in U.S. Appl. No. 11/078,232.
Ofice Action dated Jan. 10, 2008 in U.S. Appl. No. 11/077,714.
Office Action dated Apr. 21, 2008 in U.S. Appl. No. 11/077,643.
Office Action dated Jan. 3, 2008 in U.S. Appl. No. 11/157,746.
Office Action dated May 1, 2008 in U.S. Appl. No. 11/157,746.
Office Action dated Jun. 26, 2008 in U.S. Appl. No. 11/157,365.
Office Action dated Oct. 4, 2006 in U.S. Appl. No. 11/334,876.
Office Action dated May 2, 2008 in U.S. Appl. No. 11/334,876.
Office Action dated Aug. 26, 2008 in U.S. Appl. No. 11/334,876.
Office Action dated Jun. 30, 2008 in U.S. Appl. No. 11/360,252.
Office Action dated Aug. 11, 2008 in U.S. Appl. No. 11/360,819.

Bobbioni-Harsch et al. 1993. Lifespan of subcutaneous glucose sensors and their performances during dynamic glycaemia changes in rats, J. Biomed. Eng. 15:457-463.

Candas et al (1994). "An adaptive plasma glucose controller basedon on a nonlinear insulin/glucose model." IEEE Transactions on Biomedical Engineering, 41(2): 116-124.

Clark et al. 1987. Configurational cyclic voltammetry: increasing the specificity and reliablity of implanted electrodes, IEEE/Ninth Annual Conference of the Engineering in Medicine and Biollogy Society, pp. 0782-0783.

El Deheigy et al. 1986. Optimization of an implantable coated wire glucose sensor. J. Biomed Eng. 8: 121-129.

Fischer et al. 1995. Hypoglycaemia-warning by means of subcutaneous electrochemical glucose sensors: an animal study, Horm. Metab. Rese. 27:53.

Hashiguchi et al. (1994). "Development of a miniaturized glucose monitoring system by combining a needle-type glucose sensor with microdialysis sampling method: Long-term subcutaneous tissue glucose monitoring in ambulatory diabetic patients," Diabetes Care, 17(5): 387-396.

Johnson (1991). "Reproducible electrodeposition of biomolecules for the fabrication of miniature electroenzymatic biosensors," Sensors and Actuators B, 5:85-89.

Johnson et al. 1992. In vivo evaluation of an electroenzymatic glucose sensor implanted in subcutaneous tissue. Biosensors & Bioelectronics, 7:709-714.

Morff et al. 1990. Microfabrication of reproducible, economical, electroenzymatic glucose sensors, Annual International Conference of the IEEE Engineering in Medicine and Biology Society, 12(2):0483-0484.

Prabhu et al. 1981. Electrochemical studies of hydrogen peroxide at a platinum disc electrode, Electrochimica Acta 26(6):725-729.

Thome et al. 1995. Can the decrease in subcutaneous glucose concentration precede the decrease in blood glucose level? Proposition for a push-pull kinetics hypothesis, Horm, Metab. Res. 27:53.

Thomé-Duret et al. 1996. Modification of the sensitivity of glucose sensor implanted into subcutaneous tissue. Diabetes Metabolism, 22:174-178.

Yang et al (1996). "A glucose biosensor based on an oxygen electrode: In-vitro performances in a model buffer solution and in blood plasma," Biomedical Instrumentation & Technology, 30:55-61.

Zhang et al (1993). Electrochemical oxidation of H2O2 on Pt and Pt + Ir electrodes in physiological buffer and its applicability to H2O2-based biosensors. J. Electroanal. Chem., 345:253-271.

Zhu et al. (1994). "Fabrication and characterization of glucose sensors based on a microarray H2O2 electrode." Biosensors & Bioelectronics, 9: 295-300.

Office Action dated Dec. 23, 2008 in U.S. Appl. No. 12/102,745.
Office Action dated Oct. 8, 2008 in U.S. Appl. No. 10/896,627.
Office Action dated Jan. 5, 2009 in U.S. Appl. No. 11/038,340.
Office Action dated Dec. 18, 2008 in U.S. Appl. No. 10/633,329.
Office Action dated Oct. 3, 2008 in U.S. Appl. No. 10/789,359.
Office Action dated Jan. 22, 2009 in U.S. Appl. No. 11/692,154.
Office Action dated Dec. 30, 2008 in U.S. Appl. No. 11/034,343.
Office Action dated Nov. 12, 2008, 2008 in U.S. Appl. No. 11/077,715.
Office Action dated Sep. 18, 2008 in U.S. Appl. No. 11/077,883.
Office Action dated Sep. 19, 2008 in U.S. Appl. No. 11/077,765.
Office Action dated Jan. 23, 2009 in U.S. Appl. No. 11/077,765.
Office Action dated Jan. 26, 2009 in U.S. Appl. No. 11/078,230.
Office Action dated Nov. 12, 2008 in U.S. Appl. No. 11/078,232.
Office Action dated Sep. 16, 2008 in U.S. Appl. No. 11/077,714.
Office Action dated Oct. 1, 2008 in U.S. Appl. No. 11/077,643.
Office Action dated Sep. 18, 2008 in U.S. Appl. No. 11/439,630.
Office Action dated Jan. 7, 2009 in U.S. Appl. No. 11/157,365.
Office Action dated Jan. 29, 2009, in U.S. Appl. No. 11/360,252.
Office Action dated Dec. 26, 2008 in U.S. Appl. No. 11/360,819.
Office Action dated Nov. 28, 2008 in U.S. Appl. No. 11/333,837.
Office Action dated Nov. 28, 2008 in U.S. Appl. No. 11/360,250.
Office Action dated Sep. 19, 2008 in U.S. Appl. No. 11/691,432.
Office Action dated Sep. 25, 2008 in U.S. Appl. No. 11/691,424.
Office Action dated Oct. 3, 2008 in U.S. Appl. No. 11/691,466.

Aalders et al. 1991. Development of a wearable glucose sensor; studies in healthy volunteers and in diabetic patients. The International Journal of Artificial Organs 14(2):102-108.

Abe et al. 1992. Characterization of glucose microsensors for intracellular measurements. Anal. Chem. 64(18):2160-2163.

Abel et al. 1984. Experience with an implantable glucose sensor as a prerequisite of an artificial beta cell, Biomed. Biochim. Acta 43(5):577-584.

Abel et al. 2002. Biosensors for in vivo glucose measurement: can we cross the experimental stage. Biosens Bioelectron 17:1059-1070.

Alcock & Turner. 1994. Continuous Analyte Monitoring to Aid Clinical Practice. IEEE Engineering in Med. & Biol. Mag. 13:319-325.

American Heritage Dictionary, 4th Edition. 2000. Houghton Mifflin Company, p. 82.

Amin et al. 2003. Hypoglycemia prevalence in prepubertal children with type 1 diabetes on standard insulin regimen: Use of continuous glucose monitoring system. Diabetes Care 26(3):662-667.

Answers.com. "xenogenic." The American Heritage Stedman's Medical Dictionary. Houghton Mifflin Company, 2002. Answers.com Nov. 7, 2006 http://www. Answers.com/topic/xenogenic.

Atanasov et al. 1997. Implantation of a refillable glucose monitoring-telemetry device. Biosens Bioelectron 12:669-680.

Bailey et al. 2007. Reduction in hemoglobin A1c with real-time continuous glucose monitoring: results from a 12-week observational study. Diabetes Technology & Therapeutics 9(3):203-210.

Baker et al. 1996. Dynamic delay and maximal dynamic error in continuous biosensors. Anal Chem 68(8):1292-1297.

Bani Amer, M. M. 2002. An accurate amperometric glucose sensor based glucometer with eliminated cross-sensitivity. J Med Eng Technol 26(5):208-213.

Beach et al. 1999. Subminiature implantable potentiostat and modified commercial telemetry device for remote glucose monitoring. IEEE Transactions on Instrumentation and Measurement 48(6):1239-1245.

Bessman et al., Progress toward a glucose sensor for the artificial pancreas, Proceedings of a Workshop on Ion-Selective Microelectrodes, Jun. 4-5, 1973, Boston, MA, 189-197.

Biermann et al. 2008. How would patients behave if they were continually informed of their blood glucose levels? A simulation study using a "virtual" patient. Diab. Thechnol. & Therapeut., 10:178-187.

Bindra et al. 1989. Pulsed amperometric detection of glucose in biological fluids at a surface-modified gold electrode. Anal Chem 61:2566-2570.

Bisenberger et al. 1995. A triple-step potential waveform at enzyme multisensors with thick-film gold electrodes for detection of glucose and sucrose. Sensors and Actuators, B 28:181-189.

Bode et al. 1999. Continuous glucose monitoring used to adjust diabetes therapy improves glycosylated hemoglobin: A pilot study. Diabetes Research and Clinical Practice 46:183-190.

Bode et al. 2000. Using the continuous glucose monitoring system to improve the management of type 1 diabetes. Diabetes Technology & Therapeutics, 2(Suppl 1):S43-48.

Boedeker Plastics, Inc. 2009. Polyethylene Specifications Data Sheet, http://www.boedeker.com/polye_p.htm [Aug. 19, 2009 3:36:33 PM].

Boland et al. 2001. Limitations of conventional methods of self-monitoring of blood glucose. Diabetes Care 24(11):1858-1862.

Bolinder et al. 1992. Microdialysis measurement of the absolute glucose concentration in subcutaneous adipose tissue allowing glucose monitoring in diabetic patients. Diabetologia 35:1177-1180.

Bolinder et al. 1997. Self-monitoring of blood glucose in type 1 diabetic patients: Comparison with continuous microdialysis measurements of glucose in subcutaneous adipose tissue during ordinary life conditions. Diabetes Care 20(1):64-70.

Bott, A. 1998. Electrochemical methods for the determination of glucose. Current Separations 17(1):25-31.

Bowman, L.; Meindl, J. D. 1986. The packaging of implantable integrated sensors. IEEE Trans Biomed Eng BME33(2):248-255.

Brauker et al. Jun. 27, 1996. Local Inflammatory Response Around Diffusion Chambers Containing Xenografts Transplantation 61(12):1671-1677.

Braunwald, 2008. Biomarkers in heart failure. N. Engl. J. Med., 358: 2148-2159.

Bremer et al. 1999. Is blood glucose predictable from previous values? A solicitation for data. Diabetes 48:445-451.

Bremer et al. 2001. Benchmark data from the literature for evaluation of new glucose sensing technologies. Diabetes Technology & Therapeutics 3(3):409-418.

Bruckel et al. 1989. In vivo measurement of subcutaneous glucose concentrations with an enzymatic glucose sensor and a wick method. Klin Wochenschr 67:491-495.

Cai et al. 2004. A wireless, remote query glucose biosensor based on a pH-sensitive polymer. Anal Chem 76(4):4038-4043.

Campanella et al. 1993. Biosensor for direct determination of glucose and lactate in undiluted biological fluids. Biosensors & Bioelectronics 8:307-314.

Cassidy et al., Apr. 1993. Novel electrochemical device for the detection of cholesterol or glucose, Analyst, 118:415-418.

Chase et al. 2001. Continuous subcutaneous glucose monitoring in children with type 1 diabetes. Pediatrics 107:222-226.

Chen et al. 2002. Defining the period of recovery of the glucose concentration after its local perturbation by the implantation of a miniature sensor. Clin. Chem. Lab. Med. 40:786-789.

Choleau et al. 2002. Calibration of a subcutaneous amperometric glucose sensor implanted for 7 days in diabetic patients. Part 1. Effect of measurement uncertainties on the determination of sensor sensitivity and background current. Biosensors and Bioel.

Ciba® Irgacure 2959 Photoinitiator Product Description, Ciba Specialty Chemicals Inc., Basel, Switzerland.

Claremont et al. 1986. Subcutaneous implantation of a ferrocene-mediated glucose sensor in pigs. Diabetologia 29:817-821.

Claremont et al. Jul. 1986. Potentially-impintable, ferrocene-mediated glucose sensor. J. Biomed. Eng. 8:272-274.

Clark et al., 1981. One-minute electrochemical enzymic assay for cholesterol in biological materials, Clin. Chem. 27(12):1978-1982.

Clark et al. 1988. Long-term stability of electroenzymatic glucose sensors implanted in mice. Trans Am Soc Artif Intern Organs 34:259-265.

CLSI. Performance metrics for continuous interstitial glucose monitoring; approved guideline, CLSI document POCT05-A. Wayne, PA: Clinical and Laboratory Standards Institute: 2008 28(33), 72 pp.

Colangelo et al. 1967. Corrosion rate measurements in vivo, Journal of Biomedical Materials Research, 1:405-414.

Colowick et al. 1976. Methods in Enzymlology, vol. XLIV, Immobilized Enzymes. New York: Academic Press.

Cox et al. 1985. Accuracy of perceiving blood glucose in IDDM. Diabetes Care 8(6):529-536.

Csoregi et al., 1994. Design, characterization, and one-point in vivo calibration of a subcutaneously implanted glucose electrode. Anal Chem. 66(19):3131-3138.

Danielsson et al. 1988. Enzyme thermistors, Methods in Enzymology, 137:181-197.

Dassau et al., In silico evaluation platform for artifical pancreatic β-cell development-a dynamic simulator for closed loop control with hardware-in-the-loop, Diabetes Technology & Therapeutics, 11(3):1-8, 2009.

Davis et al. 1983. Bioelectrochemical fuel cell and sensor based on a quinoprotein, alcohol dehydrogenase. Enzyme Microb. Technol., vol. 5, Sep., 383-388.

Direct 30/30® meter (Markwell Medical) (Catalog).

Dixon et al. 2002. Characterization in vitro and in vivo of the oxygen dependence of an enzyme/polymer biosensor for monitoring brain glucose. Journal of Neuroscience Methods 119:135-142.

DuPont[1] Dimension AR® (Catalog), 1998.

Durliat et al. 1976. Spectrophotometric and electrochemical determinations of L(+)-lactate in blood by use of lactate dehydrogenase from yeast, Clin. Chem. 22(11):1802-1805.

El-Khatib et al. 2007. Adaptive closed-loop control provides blood-glucose regulation using dual subcutaneous insulin and glucagon infusion in diabetic swine, Journal of Diabetes Science and Technology, 1(2):181-192.

Ernst et al. 2002. Reliable glucose monitoring through the use of microsystem technology. Anal. Bioanal. Chem. 373:758-761.

Fabietti et al. 2007. Clinical validation of a new control-oriented model of insulin and glucose dynamcs in subjects with type 1 diabetes, Diabetes Technology & Therapeutics, 9(4):327-338.

Feldman et al. 2003. A continuous glucose sensor based on wired enzyme technology—results from a 3-day trial in patients with type 1 diabetes. Diabetes Technol Ther 5(5):769-779.

Fischer et al. 1987. Assessment of subcutaneous glucose concentration: validation of the wick technique as a reference for implanted electrochemical sensors in normal and diabetic dogs, Diabetologia 30:940-945.

Fischer et al. 1989. Oxygen Tension at the Subcutaneous Implantation Site of Glucose Sensors. Biomed. Biochem 11/12:965-972.

Freedman et al. 1991. Statistics, Second Edition, W.W. Norton & Company, p. 74.

Frohnauer et al. 2001. Graphical human insulin time-activity profiles using standardized definitions. Diabetes Technology & Therapeutics 3(3):419-429.

Gabbay et al. 2008. Optical coherence tomography-based continuous noninvasive glucose monitoring in patients with diabetes. Diab. Thechnol. & Therapeut., 10:188-193.

Ganesan et al., Gold layer-based dual crosslinking procedure of glucose oxidase with ferrocene monocarboxylic acid provides a stable biosensor, Analytical Biochemistry 343:188-191, 2005.

Ganesh et al., Evaluation of the VIA® blood chemistry monitor for glucose in healthy and diabetic volunteers, Journal of Diabetese Science and Technology, 2(2):182-193, Mar. 2008.

Garg et al. 1999. Correlation of fingerstick blood glucose measurements with GlucoWatch biographer glucose results in young subjects with type 1 diabetes. Diabetes Care 22(10):1708-1714.

Garg et al. 2004. Improved Glucose Excursions Using an Implantable Real-Time continuous Glucose Sensor in Adults with Type I Diabetes. Diabetes Care 27:734-738.

Gerritsen et al. 1999. Performance of subcutaneously implanted glucose sensors for continuous monitoring. The Netherlands Journal of Medicine 54:167-179.

Gerritsen, M. 2000. Problems associated with subcutaneously implanted glucose sensors. Diabetes Care 23(2):143-145.

Gilligan et al. 1994. Evaluation of a subcutaneous glucose sensor out to 3 months in a dog model. Diabetes Care 17(8):882-887.

Gilligan et al. 2004, Feasibility of continuous long-term glucose monitoring from a subcutaneous glucose sensor in humans. Diabetes Technol Ther 6:378-386.

Gouda et al., Jul. 4, 2003. Thermal inactiviation of glucose oxidase, The Journal of Biological Chemistry, 278(27):24324-24333.

Gough et al. 2000. Immobilized glucose oxidase in implantable glucose sensor technology. Diabetes Technology & Therapeutics 2(3):377-380.

Gough et al. 2003. Frequency characterization of blood glucose dynamics. Annals of Biomedical Engineering 31:91-97.

Gross et al. 2000. Efficacy and reliability of the continuous glucose monitoring system. Diabetes Technology & Therapeutics, 2(Suppl 1):S19-26.

Gross et al. 2000. Performance evaluation of the MiniMed® continuous glucose monitoring system during patient home use. Diabetes Technology & Therapeutics 2(1):49-56.

Hall et al. 1998. Electrochemical oxidation of hydrogen peroxide at platinum electrodes. Part I: An adsorption-controlled mechanism. Electrochimica Acta, 43(5-6):579-588.

Hall et al. 1998. Electrochemical oxidation of hydrogen peroxide at platinum electrodes. Part II: Effect of potential. Electrochimica Acta 43(14-15):2015-2024.

Hall et al. 1999. Electrochemical oxidation of hydrogen peroxide at platinum electrodes. Part III: Effect of temperature. Electrochimica Acta, 44:2455-2462.

Hall et al. 1999. Electrochemical oxidation of hydrogen peroxide at platinum electrodes. Part IV: Phosphate buffer dependence. Electrochimica Acta, 44:4573-4582.

Hall et al. 2000. Electrochemical oxidation of hydrogen peroxide at platinum electrodes. Part V: Inhibition by chloride. Electrochimica Acta, 45:3573-3579.

Hamilton Syringe Selection Guide. 2006. Syringe Selection. www.hamiltoncompany.com.

Heise et al. 2003. Hypoglycemia warning signal and glucose sensors: Requirements and concepts. Diabetes Technology & Therapeutics 5:563-571.

Heller, A. 1999. Implanted electrochemical glucose sensors for the management of diabetes. Annu Rev Biomed Eng 1:153-175.

Heller, A. 2003. Plugging metal connectors into enzymes. Nat Biotechnol 21:631-2.

Hoel, Paul G. 1976. Elementary Statistics, Fourth Edition. John Wiley & Sons, Inc.. pp. 113-114.

Hrapovic et al. 2003. Picoamperometric detection of glucose at ultrasmall platinum-based biosensors: preparation and characterization. Anal Chem 75:3308-3315.

http://www.merriam-webster.com/dictionary. definition for "aberrant," Aug. 19, 2008, p. 1.

Huang et al. A 0.5mV passive telemetry IC for biomedical applications. Swiss Federal Institute of Technology. 4 pp.

Huang et al. Aug. 1975. Electrochemical Generation of Oxygen. 1: The Effects of Anions and Cations on Hydrogen Chemisorption and Aniodic Oxide Film Formation on Platinum Electrode. 2: The Effects of Anions and Cations on Oxygen Generation on Platinum E.

Hunter et al. 2000. Minimally Invasive Glucose Sensor and Insulin Delivery System. MIT Home Automation and Healthcare Consortium. Progress Report No. 25.

Ishikawa et al. 1998. Initial evaluation of a 290-mm diameter subcutaneous glucose sensor: Glucose monitoring with a biocompatible, flexible-wire, enzyme-based amperometric microsensor in diabetic and nondiabetic humans. Journal of Diabetes and Its Compl.

Jablecki et al. 2000. Simulations of the frequency response of implantable glucose sensors. Analytical Chemistry 72:1853-1859.

Jaremko et al. 1998. Advances toward the implantable artificial pancreas for treatment of diabetes. Diabetes Care 21(3):444-450.

Jeutter, D. C. 1982. A transcutaneous implanted battery recharging and biotelemeter power switching system. IEEE Trans Biomed Eng 29:314-321.

Jovanovic, L. 2000. The role of continuous glucose monitoring in gestational diabetes mellitus. Diabetes Technology & Therapeutics, 2 Suppl 1, S67-71.

Kacaniklic May-Jun. 1994. Electroanalysis, 6(5-6):381-390.

Kang et al. 2003. In vitro and short-term in vivo characteristics of a Kel-F thin film modified glucose sensor. Anal Sci 19:1481-1486.

Kaufman. 2000. Role of the continuous glucose monitoring system in pediatric patients. Diabetes Technology & Therapeutics 2(1):S-49-S-52.

Kaufman et al. 2001. A pilot study of the continuous glucose monitoring system. Diabetes Care 24(12):2030-2034.

Keedy et al. 1991. Determination of urate in undiluted whole blood by enzyme electrode. Biosensors & Bioelectronics, 6: 491-499.

Kerner et al. 1988. A potentially implantable enzyme electrode for amperometric measurement of glucose, Horm Metab Res Suppl. 20:8-13.

Kerner, W. 2001. Implantable glucose sensors: Present status and future developments. Exp. Clin. Endocrinol. Diabetes 109(Suppl 2):S341-346.

Klueh et al. 2003. Use of Vascular Endothelia Cell Growth Factor Gene Transfer to Enhance Implantable Sensor Function in Vivo, Biosensor Function and Vegf-Gene Transfer, pp. 1072-1086.

Ko, Wen H. 1985. Implantable Sensors for Closed-Loop Prosthetic Systems, Futura Pub. Co., Inc., Mt. Kisco, NY, Chapter 15:197-210.

Kondo et al. 1982. A miniature glucose sensor, implantable in the blood stream. Diabetes Care. 5(3):218-221.

Koschinsky et al. 2001. Sensors for glucose monitoring: Technical and clinical aspects. Diabetes Metab. Res. Rev. 17:113-123.

Kost et al. 1985. Glucose-sensitive membranes containing glucose oxidase: activitiy, swelling, and permeability studies, Journal of Biomedical Materials Research 19:1117-1133.

Koudelka et al. 1989. In vivo response of microfabricated glucose sensors to glycemia changes in normal rats. Biomed Biochim Acta 48(11-12):953-956.

Koudelka et al. 1991. In-vivo behaviour of hypodermically implanted microfabricated glucose sensors. Biosensors & Bioelectronics 6:31-36.

Kraver et al. 2001. A mixed-signal sensor interface microinstrument. Sensors and Actuators A 91:266-277.

Krouwer, J. S. 2002. Setting performance goals and evaluating total analytical error for diagnostic assays. Clinical Chemistry 48(6):919-927.

Kruger et al. 2000. Psychological motivation and patient education: A role for continuous glucose monitoring. Diabetes Technology & Therapeutics, 2(Suppl 1):S93-97.

Kulys et al., 1994. Carbon-paste biosensors array for long-term glucose measurement, Biosensors & Beioelectronics, 9:491-500.

Kunjan et al., Automated blood sampling and glocuse sensing in critical care settings, Journal of Diabetes Science and Technology 2(3):194-200, Mar. 2008.

Kurtz et al. 2005. Recommendations for blood pressure measurement in humans and experimental animals, Part 2: Blood pressure measurement in experimental animals, A statement for professionals from the subcommittee of professional and public education of.

LaCourse et al. 1993. Optimization of waveforms for pulsed amperometric detection of carbohydrates based on pulsed voltammetry. Analytical Chemistry 65:50-52.

Ladd et al., Structure Determination by X-ray Crystallography, 3rd ed. Plenum, 1996, Ch. 1, pp. xxi-xxiv and 1-58.

Lehmann et al. May 1994. Retrospective valication of a physiological model of glucose-iunsulin interaaction in tyhpe 1 diabetes mellitus, Med. Eng. Phys. 16:193-202.

Lerner et al. 1984. An implantable electrochemical glucose sensor. Ann. N. Y. Acad. Sci. 428:263-278.

Lewandowski et al. 1988. Evaluation of a miniature blood glucose sensor. Trans Am Soc Artif Intern Organs 34:255-258.

Leypoldt et al. 1984. Model of a two-substrate enzyme electrode for glucose. Anal. Chem. 56:2896-2904.

Linke et al. 1994. Amperometric biosensor for in vivo glucose sensing based on glucose oxidase immobilized in a redox hydrogel. Biosensors & Bioelectronics 9:151-158.

Lowe, 1984. Biosensors, Trends in Biotechnology, 2(3):59-65.

Lyandres et al. (2008). Progress toward an in vivo surface-enhanced raman spectroscopy glucose sensor. Diabetes Technology & Therapeutics, 10(4): 257-265.

Lynch et al. 2001. Estimation-based model predictive control of blood glucose in type I diabetics: A simulation study. Proceedings of the IEEE 27th Annual Northeast Bioengineering Conference, pp. 79-80.

Lynn, P. A. 1971. Recursive digital filters for biological signals. Med. & Biol. Engng. 9:37-43.

Malin et al. 1999. Noninvasive Prediction of Glucose by Near-Infrared Diffuse Reflectance Spectroscopy. Clinical Chemistry 45:9, 1651-1658.

Maran et al. 2002. Continuous subcutaneous glucose monitoring in diabetic patients: A multicenter analysis. Diabetes Care 25(2):347-352.

March, W. F. 2002. Dealing with the delay. Diabetes Technol Ther 4(1):49-50.

Marena et al. 1993. The artifical endocrine pancreas in clinical practice and research. Panminerva Medica 35(2):67-74.

Mascini et al. 1989. Glucose electrochemical probe with extended linearity for whole blood. J Pharm Biomed Anal 7(12): 1507-1512.

Mastrototaro et al. 2003. Reproducibility of the continuous glucose monitoring system matches previous reports and the intended use of the product. Diabetes Care 26:256; author reply p. 257.

Mastrototaro, J. J. 2000. The MiniMed continuous glucose monitoring system. Diabetes Technol Ther 2(Suppl 1):S13-8.

Matsumoto et al. 1998. A micro-planar amperometeric glucose sensor unsusceptible to interference species. Sensors and Actuators B 49:68-72.

Matthews et al. 1988. An amperometric needle-type glucose sensor testing in rats and man. Diabetic Medicine 5:248-252.

Mazze et al. 2008. Characterizing glucose exposure for individuals with normal glucose tolerance using continuous glucose monitoring and ambulatory glucose profile analysis. Diab. Thechnol. & Therapeut., 10:149-159.

McCartney et al. 2001. Near-infrared fluorescence lifetime assay for serum glucose based on allophycocyanin-labeled concanavalin A. Anal Biochem 292:216-221.

McGrath et al. 1995. The use of differential measurements with a glucose biosensor for interference compensation during glucose determinations by flow injection analysis. Biosens Bioelectron 10:937-943.

Memoli et al. 2002. A comparison between different immobilised glucoseoxidase-based electrodes. J Pharm Biomed Anal 29:1045-1052.

Merriam-Webster Online Dictionary. Definition of "acceleration". http://www.merriam-webster.com/dictionary/Acceleration Jan. 11, 2010.

Merriam-Webster Online Dictionary. Definition of "system". http://www.merriam-webster.com/dictionary/System Jan. 11, 2010.

Merriam-Webster Online Dictionary. The term "nominal." http://www.m-w.com/dictionary/nominal.

Metzger et al. Jul. 2002. Reproducibility of glucose measurements using the glucose sensor. Diabetes Care 25(6):1185-1191.

Meyerhoff et al. 1992. On line continuous monitoring of subcutaneous tissue glucose in men by combining portable glucosensor with microdialysis. Diabetologia 35:1087-1092.

Monsod et al. 2002. Do sensor glucose levels accurately predict plasma glucose concentrations during hypoglycemia and hyperinsulinemia? Diabetes Care 25(5):889-893.

Mosbach et al. 1975. Determination of heat changes in the proximity of immobilized enzymes with an enzyme termistor and its use for the assay of metobolites, Biochim. Biophys. Acta. (Enzymology), 403:256-265.

Motonaka et al. 1993. Determination of cholesteral and cholesteral ester with novel enzyme microsensors, Anal. Chem. 65:3258-3261.

Moussy et al. 1994. A miniaturized Nafion-based glucose sensor: In vitro and in vivo evaluation in dogs. Int. J. Artif. Organs 17(2):88-94.

Muslu. 1991. Trickling filter performance. Apllied Biochemistry and Biotechnology 37:211-224.

Nafion® 117 Solution Product Description, Product No. 70160, Sigma-Aldrich Corp., St. Louis, MO.

Neuburger et al. 1987. Pulsed amperometric detection of carbohydrates at gold electrodes with a two-step potential waveform. Anal. Chem. 59:150-154.

Ohara et al. 1994. "Wired" enzyme electrodes for amperometric determination of glucose or lactate in the presence of interfering substances. Anal Chem 66:2451-2457.

Oxford English Dictionary Online. Definition of "impending". http://www.askoxford.com/results/?view=dev dict&field-12668446 Impending&branch= Jan. 11, 2010.

Palmisano et al. 2000. Simultaneous monitoring of glucose and lactate by an interference and cross-talk free dual electrode amperometric biosensor based on electropolymerized thin films. Biosensors & Bioelectronics 15:531-539.

Panteleon et al. 2003. The role of the independent variable to glucose sensor calibration. Diabetes Technology & Therapeutics 5(3):401-410.

Parker et al. 1999. A model-based algorithm for blood glucose control in type I diabetic patients. IEEE Trans. Biomed. Eng. 46(2):148-157.

Patel et al. 2003. Amperometric glucose sensors based on ferrocene containing polymeric electron transfer systems-a preliminary report. Biosens Bioelectron 18:1073-6.

Peacock et al. 2008. Cardiac troponin and outcome in acute heart failure. N. Engl. J. Med., 358: 2117-2126.

Pfeiffer, E.F. 1990. The glucose sensor: the missing link in diabetes therapy, Horm Metab Res Suppl. 24:154-164.

Pfeiffer et al. 1992. On line continuous monitoring of subcutaneous tissue glucose is feasible by combining portable glucosensor with microdialysis. Horm. Metab. Res. 25:121-124.

Pichert et al. 2000. Issues for the coming age of continuous glucose monitoring Diabetes Educ 26(6):969-980.

Pickup et al. 1989. Potentially-implantable, amperometric glucose sensors with mediated electron transfer: improving the operating stability. Biosensors 4:109-119.

Pickup et al. 1993. Developing glucose sensors for in vivo use. Elsevier Science Publishers Ltd (UK), Tibtech vol. 11: 285-291.

Pinner et al., Cross-linking of cellulose acetate by ionizing radiation, Nature, vol. 184, 1303-1304, Oct. 24, 1959.

Pitzer et al. 2001. Detection of hypoglycemia with the GlucoWatch biographer. Diabetes Care 24(5):881-885.

Poirier et al. 1998. Clinical and statistical evaluation of self-monitoring blood glucose meters. Diabetes Care 21(11):1919-1924.

Poitout et al. 1994. Development of a glucose sensor for glucose monitoring in man: the disposable implant concept. Clinical Materials 15:241-246.

Postlethwaite et al. 1996. Interdigitated array electrode as an alternative to the rotated ring-disk electrode for determination of the reaction products of dioxygen reduction. Analytical Chemistry 68:2951-2958.

Quinn et al. 1995. Kinetics of glucose delivery to subcutaneous tissue in rats measured with 0.3-mm amperometric microsensors. The American Physiological Society E155-E161.

Quinn et al. 1997. Biocompatible, glucose-permeable hydrogel for in situ coating of implantable biosensors. Biomaterials 18:1665-1670.

Rabah et al., 1991. Electrochemical wear of graphite anodes during electrolysis of brine, Carbon, 29(2):165-171.

Reach et al. 1986. A Method for Evaluating in vivo the Functional Characteristics of Glucose Sensors. Biosensors 2:211-220.

Reach, G. 2001. Which threshold to detect hypoglycemia? Value of receiver-operator curve analysis to find a compromise between sensitivity and specificity. Diabetes Care 24(5):803-804.

Reach, Gerard. 2001. Letters to the Editor Re: Diabetes Technology & Therapeutics, 2000;2:49-56. Diabetes Technology & Therapeutics 3(1):129-130.

Rebrin et al. 1992. Subcutaenous glucose monitoring by means of electrochemical sensors: fiction or reality? J. Biomed. Eng. 14:33-40.

Rebrin et al. 1999. Subcutaneous glucose predicts plasma glucose independent of insulin: Implications for continuous monitoring. Am. J. Physiol. 277:E561-71.

Reusch. 2004. Chemical Reactivity. Organometallic Compounds. Virtual Textbook of Organic Chem. pp. 1-16, http://www.cem.msu.edu/~reusch/VirtualText/orgmetal.htm.

Rigla et al. 2008. Real-time continuous glucose monitoring together with telemedical assitance improves glycemic control and glucose stability in pump-treated patients. Diab. Thechnol. & Therapeut., 10:194-199.

Salardi et al. 2002. The glucose area under the profiles obtained with continuous glucose monitoring system relationships with HbA1c in pediatric type 1 diabetic patients. Diabetes Care 25(10):1840-1844.

San Diego Plastics, Inc. 2009. Polyethylene Data Sheet, http://www.sdplastics.com/polyeth.html.

Sansen et al. 1985. "Glucose sensor with telemetry system." In Ko, W. H. (Ed.). Implantable Sensors for Closed Loop Prosthetic Systems. Chap. 12, pp. 167-175, Mount Kisco, NY: Futura Publishing Co.

Sansen et al. 1990. A smart sensor for the voltammetric measurement of oxygen or glucose concentrations. Sensors and Actuators B 1:298-302.

Schmidtke et al., Measurement and modeling of the transient difference between blood and subcutaneous glucose concentrations in the rat after injection of insulin. Proc Natl Acad Sci U S A 1998, 95, 294-299.

Schoemaker et al. 2003. The SCGM1 system: Subcutaneous continuous glucose monitoring based on microdialysis technique. Diabetes Technology & Therapeutics 5(4):599-608.

Schoonen et al. 1990 Development of a potentially wearable glucose sensor for patients with diabetes mellitus: design and in-vitro evaluation. Biosensors & Bioelectronics 5:37-46.

Service et al. 1987. Measurements of glucose control. Diabetes Care, 10: 225-237.

Service, R. F. 2002. Can sensors make a home in the body? Science 297:962-3.

Sharkawy et al. 1996. Engineering the tissue which encapsulates subcutaneous implants. I. Diffusion properties, J Biomed Mater Res, 37:401-412.

Shichiri et al. 1982. Wearable artificial endocrine pancrease with needle-type glucose sensor. Lancet 2:1129-1131.

Slater-Maclean et al. 2008. Accuracy of glycemic measurements in the critically ill. Diab. Thechnol. & Therapeut., 10:169-177.

Sokolov et al. 1995. Metrological opportunities of the dynamic mode of operating an enzyme amperometric biosensor. Med. Eng. Phys. 17(6):471-476.

Sproule et al. 2002. Fuzzy pharmacology: Theory and applications. Trends in Pharmacological Sciences, 23(9):412-417.

Sriyudthsak et al. 1996. Enzyme-epoxy membrane based glucose analyzing system and medical applications. Biosens Bioelectron 11:735-742.

Steil et al. 2003. Determination of plasma glucose during rapid glucose excursions with a subcutaneous glucose sensor. Diabetes Technology & Therapeutics 5(1):27-31.

Stern et al., 1957. Electrochemical polarization: 1. A theoretical analysis of the shape of polarization curves, Journal of the Electrochemical Society, 104(1):56-63.

Sternberg et al. 1996. Does fall in tissue glucose precede fall in blood glucose? Diabetologia 39:609-612.
Street et al. 1988. A note on computing robust regression estimates via iteratively reweighted least squares. The American Statistician 42(2):152-154.
Sumino T. et al. 1998. Preliminary study of continuous glucose monitoring with a microdialysis technique. Proceedings of the IEEE, 20(4):1775-1778.
Takegami et al. 1992. Pervaporation of ethanol water mixtures using novel hydrophobic membranes containing polydimethylsiloxane, Journal of Membrance Science, 75(93-105).
Tanenberg et al. 2000. Continuous glucose monitoring system: A new approach to the diagnosis of diabetic gastroparesis. Diabetes Technology & Therapeutics, 2 Suppl 1:S73-80.
Tatsuma et al. 1991. Oxidase/peroxidase bilayer-modified electrodes as sensors for lactate, pyruvate, cholesteral and uric acid, Analytica Chimica Acta, 242:85-89.
Thome-Duret et al. 1996. Use of a subcutaneous glucose sensor to detect decreases in glucose concentration prior to observation in blood, Anal. Chem. 68:3822-3826.
Thomé-Duret et al. 1998. Continuous glucose monitoring in the free-moving rat. Metabolism, 47:799-803.
Tierney et al. 2000. The GlucoWatch® biographer: A frequent, automatic and noninvasive glucose monitor. Ann. Med. 32:632-641.
Tilbury et al. 2000. Receiver operating characteristic analysis for intelligent medical systems—A new approach for finding confidence intervals. IEEE Transactions on Biomedical Engineering 47(7):952-963.
Torjman et al., Glucose monitoring in acute care: technologies on the horizon, Journal of Deabetes Science and Technology, 2(2):178-181, Mar. 2008.
Trecroci, D. 2002. A Glimpse into the Future- Continuous Monitoring of Glucose with a Microfiber. Diabetes Interview 42-43.
Tse and Gough. 1987. Time-Dependent Inactivation of Immobilized Glucose Oxidase and Catalase. Biotechnol. Bioeng. 29:705-713.
Turner et al. 1984. Carbon Monoxide: Acceptor Oxidoreductase from Pseudomonas Thermocarboxydovorans Strain C2 and its use in a Carbon Monoxide Sensor. Analytica Chimica Acta, 163: 161-174.
Updike et al. 1967. The enzyme electrode. Nature, 214:986-988.
Updike et al. 1988. Laboratory Evaluation of New Reusable Blood Glucose Sensor. Diabetes Care, 11:801-807.
Updike et al. 2000. A subcutaneous glucose sensor with improved longevity, dynamic range, and stability of calibration. Diabetes Care 23(2):208-214.
Vadgama, P. Nov. 1981. Enzyme electrodes as practical biosensors. Journal of Medical Engineering & Technology 5(6):293-298.
Vadgama. 1988. Diffusion limited enzyme electrodes. NATO ASI Series: Series C, Math and Phys. Sci. 226:359-377.
Velho et al. 1989. In vitro and in vivo stability of electrode potentials in needle-type glucose sensors. Influence of needle material. Diabetes 38:164-171.
Wang et al. 1994. Highly Selective Membrane-Free, Mediator-Free Glucose Biosensor. Anal. Chem. 66:3600-3603.
Wang et al. 1997. Improved ruggedness for membrane-based amperometric sensors using a pulsed amperometric method. Anal Chem 69:4482-4489.
Ward et al. 2000. Understanding Spontaneous Output Fluctuations of an Amperometric Glucose Sensor: Effect of Inhalation Anesthesia and e of a Nonenzyme Containing Electrode. ASAIO Journal 540-546.
Ward et al. 2002. A new amperometric glucose microsensor: In vitro and short-term in vivo evaluation. Biosensors & Bioelectronics, 17:181-189.
Wientjes, K. J. C. 2000. Development of a glucose sensor for diabetic patients (Ph.D. Thesis).
Wikipedia 2006. "Intravenous therapy," http://en.wikipedia.org/wiki/Intravenous_therapy, Aug. 15, 2006, 6 pp.
Wiley Electrical and Electronics Engineering Dictionary. 2004. John Wiley & Sons, Inc. pp. 141, 142, 548, 549.

Wilkins et al. 1988. The coated wire electrode glucose sensor, Horm Metab Res Suppl., 20:50-55.
Wilkins et al. 1995. Glucose monitoring: state of the art and future possibilities. Med Eng Phys 18:273-288.
Wilkins et al. 1995. Integrated implantable device for long-term glucose monitoring. Biosens. Bioelectron 10:485-494.
Wilson et al. 2000. Enzyme-based biosensors for in vivo measurements. Chem. Rev., 100:2693-2704.
Woodward. 1982. How Fibroblasts and Giant Cells Encapsulate Implants: Considerations in Design of Glucose Sensor. Diabetes Care 5:278-281.
Worsley et al., Measurement of glucose in blood with a phenylboronic acid optical sensor, Journal of Diabetes Science and Technology, 2(2):213-220, Mar. 2008.
Wright et al., Bioelectrochemical dehalogenations via direct electrochemistry of poly(ethylene oxide)- modified myoglobin, Electrochemistry Communications 1 (1999) 603-611.
Yamasaki, Yoshimitsu. Sep. 1984. The development of a needle-type glucose sensor for wearable artificial endocrine pancreas. Medical Journal of Osaka University 35(1-2):25-34.
Yamasaki et al. 1989. Direct measurement of whole blood glucose by a needle-type sensor. Clinica Chimica Acta. 93:93-98.
Yang et al. 1998. Development of needle-type glucose sensor with high selectivity. Science and Actuators B 46:249-256.
Ye et al. 1993. High Current Density 'Wired' Quinoprotein Glucose Dehydrogenase Electrode. Anal. Chem. 65:238-241.
Zavalkoff et al. 2002. Evaluation of conventional blood glucose monitoring as an indicator of integrated glucose values using a continuous subcutaneous sensor. Diabetes Care 25(9):1603-1606.
Zethelius et al. 2008. Use of multiple biomarkers to improve the prediction of death from cardiovascular causes. N. Engl. J. Med., 358: 2107-2116.
Zhang et al. 1993. In vitro and in vivo evaluation of oxygen effects on a glucose oxidase based implantable glucose sensor. Analytica Chimica Acta, 281:513-520.
Zhang et al. 1994. Elimination of the acetaminophen interference in an implantable glucose sensor. Analytical Chemistry 66(7):1183-1188.
Official Communication in European App. No. 05771646.6, dated Sep. 19, 2009.
Office Action dated Aug. 19, 2009 in U.S. Appl. No. 11/021,046.
Office Action dated Jul. 30, 2009 in U.S. Appl. No. 12/102,654.
Office Action dated Mar. 10, 2010 in U.S. Appl. No. 12/102,654.
Office Action dated Jan. 13, 2010 in U.S. Appl. No. 12/139,305.
Office Action dated Nov. 9, 2009 in U.S. Appl. No. 11/038,340.
Office Action mailed Mar. 3, 2010 in U.S. Appl. No. 12/111,062.
Office Action dated Nov. 12, 2009 in U.S. Appl. No. 11/077,883.
Office Action dated Jan. 5, 2010 in U.S. Appl. No. 11/078,232.
Office Action dated Dec. 31, 2009 in U.S. Appl. No. 11/077,714.
Office Action dated Jan. 27, 2010 in U.S. Appl. No. 11/077,714.
Office Action dated Sep. 2, 2009 in U.S. Appl. No. 11/078,072.
Office Action dated Feb. 18, 2010 in U.S. Appl. No. 11/078,072.
Office Action dated Dec. 29, 2009 in U.S. Appl. No. 11/077,739.
Office Action dated Mar. 1, 2010 in U.S. Appl. No. 11/077,739.
Office Action dated Feb. 3, 2010 in U.S. Appl. No. 11/077,765.
Office Action dated Aug. 21, 2009 in U.S. Appl. No. 11/360,299.
Office Action dated Sep. 2, 2009 in U.S. Appl. No. 11/439,630.
Office Action dated Jan. 22, 2010 in U.S. Appl. No. 11/439,630.
Office Action dated Jan. 21, 2010 in U.S. Appl. No. 11/157,365.
Office Action dated Aug. 25, 2009 in U.S. Appl. No. 11/334,876.
Office Action dated Oct. 29, 2009 in U.S. Appl. No. 11/360,819.
Office Action dated Feb. 23, 2010 in U.S. Appl. No. 12/113,508.
Office Action dated Nov. 20, 2009 in U.S. Appl. No. 11/360,250.
Office Action dated Mar. 5, 2010 in U.S. Appl. No. 11/360,250.
Office Action dated Nov. 30, 2009 in U.S. Appl. No. 11/691,432.
Office Action dated Feb. 18, 2010 in U.S. Appl. No. 11/691,432.
Office Action dated Nov. 12, 2009 in U.S. Appl. No. 11/691,424.
Office Action dated Dec. 8, 2009 in U.S. Appl. No. 11/691,424.

* cited by examiner

TRANSCUTANEOUS MEDICAL DEVICE WITH VARIABLE STIFFNESS

RELATED APPLICATION

This application claims the benefit of U.S. Provisional Application No. 60/587,800 filed Jul. 13, 2004; which is incorporated by reference herein in its entirety, and which is hereby made a part of this specification.

FIELD OF THE INVENTION

The present invention relates generally to systems and methods for use with partially implantable medical devices. More particularly, the present invention relates to systems and methods for use with transcutaneous analyte sensors.

BACKGROUND OF THE INVENTION

Transcutaneous medical devices are useful in medicine for providing the enhanced functionality of a wholly implantable medical device while avoiding many of the complications associated with a wholly implantable device. For example, transcutaneous analyte sensors are generally minimally invasive compared to wholly implantable sensor, and are capable of measuring an analyte concentration for a short period of time (e.g., three days) with similar accuracy as in a wholly implantable sensor.

SUMMARY OF THE INVENTION

In a first aspect, a transcutaneous analyte sensor is provided, the sensor comprising an elongated flexible portion, wherein the elongated flexible portion has a variable stiffness along at least a portion of its length.

In an embodiment of the first aspect, the sensor comprises at least one wire in a helical configuration, and wherein the variable stiffness is provided by a variable pitch of the helical configuration.

In an embodiment of the first aspect, the sensor comprises at least one wire in a helical configuration, and wherein the variable stiffness is provided by a variable cross-section of the wire.

In an embodiment of the first aspect, the sensor comprises at least one wire, and wherein the variable stiffness is provided by a variable hardness of the wire.

In an embodiment of the first aspect, the variable stiffness of the elongated flexible portion is produced by subjecting the wire to an annealing process.

In an embodiment of the first aspect, the sensor comprises at least one wire, the wire having a variable diameter.

In an embodiment of the first aspect, a distal portion of the sensor is more flexible than a proximal portion of the sensor.

In an embodiment of the first aspect, an intermediate portion of the sensor is more flexible than at least one of a distal portion of the sensor and a proximal portion of the sensor.

In an embodiment of the first aspect, a distal tip of the sensor is stiffer than at least one of an intermediate portion of the sensor and a proximal portion of the sensor.

In a second aspect, a transcutaneous analyte sensor is provided, the sensor comprising a distal portion, an intermediate portion, and a proximal portion, wherein the distal portion is adapted to be inserted through a skin of a host, wherein the proximal portion is adapted to remain substantially external to the host when the distal portion is inserted in the host, and wherein a stiffness of the sensor is variable along a length of the sensor.

In an embodiment of the second aspect, the proximal portion is stiffer than the distal portion.

In an embodiment of the second aspect, the sensor comprises at least one wire in a helical configuration, and wherein a difference in stiffness of the distal portion and the proximal portion is provided by varying a pitch of the helical configuration.

In an embodiment of the second aspect, the sensor comprises at least one wire in a helical configuration, and wherein a difference in flexibility of the distal portion and the proximal portion is provided by a varying a cross-section of the wire.

In an embodiment of the second aspect, the sensor comprises at least one wire, and wherein a difference in flexibility of the distal portion and the proximal portion is provided by a varying a hardness of the wire.

In an embodiment of the second aspect, a variation in stiffness of the elongated flexible portion is produced by subjecting the wire to an annealing process.

In an embodiment of the second aspect, the intermediate portion is more flexible than at least one of the distal portion and the proximal portion.

In an embodiment of the second aspect, the distal portion comprises a distal tip on an end of the sensor that is stiffer a substantial portion of the sensor.

In an embodiment of the second aspect, the intermediate portion is more flexible than at least one of the distal portion and the proximal portion.

In an embodiment of the second aspect, the distal portion comprises a distal tip on an end of the sensor that is stiffer a substantial portion of the sensor.

In a third aspect, a transcutaneous analyte sensor is provided, the sensor comprising an in vivo portion adapted for insertion into a host and an ex vivo portion adapted for operable connection to a device that remains external to the host, wherein the sensor is configured to absorb a relative movement between the ex vivo portion of the sensor and the in vivo portion of the sensor.

In an embodiment of the third aspect, the sensor is configured to absorb a relative movement by a flexibility of at least an intermediate portion located between the in vivo portion and the ex vivo portion.

In an embodiment of the third aspect, the device comprises a housing adapted for mounting on a skin of a host, wherein the housing comprises electrical contacts operably connected to the sensor.

In an embodiment of the third aspect, the ex vivo portion of the sensor is has a preselected stiffness to maintain a stable connection between the sensor and the electrical contacts.

In an embodiment of the third aspect, the in vivo portion of the sensor has a preselected flexibility to minimize mechanical stresses caused by motion of the host.

In an embodiment of the third aspect, a stiffness of the ex vivo portion of the sensor is greater than a stiffness of the in vivo portion of the sensor.

DETAILED DESCRIPTION OF THE PREFERRED EMBODIMENT

Figure 1A:
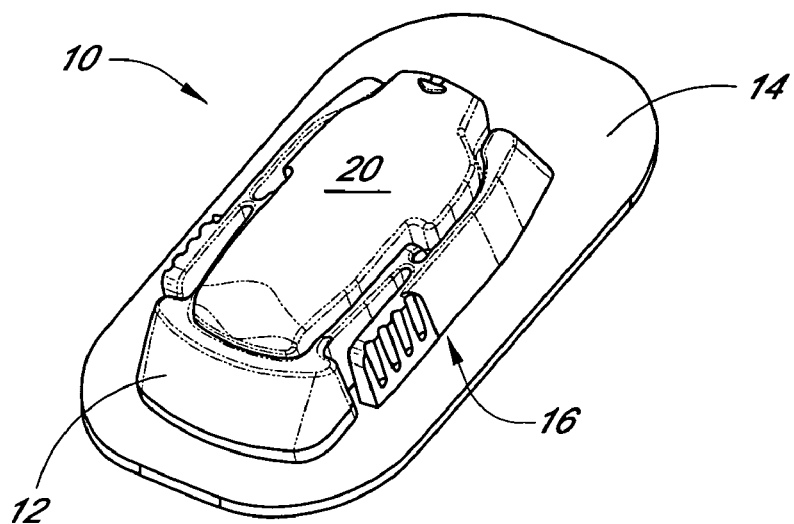
FIG. 1A is a perspective view of a transcutaneous sensor assembly.

The following description and examples illustrate some exemplary embodiments of the disclosed invention in detail. Those of skill in the art will recognize that there are numerous variations and modifications of this invention that are encompassed by its scope. Accordingly, the description of a certain exemplary embodiment should not be deemed to limit the scope of the present invention.

DEFINITIONS

In order to facilitate an understanding of the preferred embodiments, a number of terms are defined below.

The term "analyte" as used herein is a broad term and is used in its ordinary sense, including, without limitation, to refer to a substance or chemical constituent in a biological fluid (for example, blood, interstitial fluid, cerebral spinal fluid, lymph fluid or urine) that can be analyzed. Analytes can include naturally occurring substances, artificial substances, metabolites, and/or reaction products. In some embodiments, the analyte for measurement by the sensing regions, devices, and methods is glucose. However, other analytes are contemplated as well, including but not limited to acarboxyprothrombin; acylcarnitine; adenine phosphoribosyl transferase; adenosine deaminase; albumin; alpha-fetoprotein; amino acid profiles (arginine (Krebs cycle), histidine/urocanic acid, homocysteine, phenylalanine/tyrosine, tryptophan); andrenostenedione; antipyrine; arabinitol enantiomers; arginase; benzoylecgonine (cocaine); biotinidase; biopterin; c-reactive protein; carnitine; carnosinase; CD4; ceruloplasmin; chenodeoxycholic acid; chloroquine; cholesterol; cholinesterase; conjugated 1-βhydroxy-cholic acid; cortisol; creatine kinase; creatine kinase MM isoenzyme; cyclosporin A; d-penicillamine; de-ethylchloroquine; dehydroepiandrosterone sulfate; DNA (acetylator polymorphism, alcohol dehydrogenase, alpha 1-antitrypsin, cystic fibrosis, Duchenne/Becker muscular dystrophy, glucose-6-phosphate dehydrogenase, hemoglobin A, hemoglobin S, hemoglobin C, hemoglobin D, hemoglobin E, hemoglobin F, D-Punjab, beta-thalassemia, hepatitis B virus, HCMV, HIV-1, HTLV-1, Leber hereditary optic neuropathy, MCAD, RNA, PKU, *Plasmodium vivax*, sexual differentiation, 21-deoxycortisol); desbutylhalofantrine; dihydropteridine reductase; diptheria/tetanus antitoxin; erythrocyte arginase; erythrocyte protoporphyrin; esterase D; fatty acids/acylglycines; free β-human chorionic gonadotropin; free erythrocyte porphyrin; free thyroxine (FT4); free tri-iodothyronine (FT3); fumarylacetoacetase; galactose/gal-1-phosphate; galactose-1-phosphate uridyltransferase; gentamicin; glucose-6-phosphate dehydrogenase; glutathione; glutathione perioxidase; glycocholic acid; glycosylated hemoglobin; halofantrine; hemoglobin variants; hexosaminidase A; human erythrocyte carbonic anhydrase I; 17-alpha-hydroxyprogesterone; hypoxanthine phosphoribosyl transferase; immunoreactive trypsin; lactate; lead; lipoproteins ((a), B/A-1, β); lysozyme; mefloquine; netilmicin; phenobarbitone; phenytoin; phytanic/pristanic acid; progesterone; prolactin; prolidase; purine nucleoside phosphorylase; quinine; reverse tri-iodothyronine (rT3); selenium; serum pancreatic lipase; sissomicin; somatomedin C; specific antibodies (adenovirus, anti-nuclear antibody, anti-zeta antibody, arbovirus, Aujeszky's disease virus, dengue virus, *Dracunculus medinensis*, *Echinococcus granulosus*, *Entamoeba histolytica*, enterovirus, *Giardia duodenalisa*, *Helicobacter pylori*, hepatitis B virus, herpes virus, HIV-1, IgE (atopic disease), influenza virus, *Leishmania donovani*, leptospira, measles/mumps/rubella, *Mycobacterium leprae*, *Mycoplasma pneumoniae*, *Myoglobin*, *Onchocerca volvulus*, parainfluenza virus, *Plasmodium falciparum*, poliovirus, *Pseudomonas aeruginosa*, respiratory syncytial virus, rickettsia (scrub typhus), *Schistosoma mansoni*, *Toxoplasma gondii*, *Trepenoma pallidium*, *Trypanosoma cruzi/rangeli*, vesicular stomatis virus, *Wuchereria bancrofti*, yellow fever virus); specific antigens (hepatitis B virus, HIV-1); succinylacetone; sulfadoxine; theophylline; thyrotropin (TSH); thyroxine (T4); thyroxine-binding globulin; trace elements; transferrin; UDP-galactose-4-epimerase; urea; uroporphyrinogen I synthase; vitamin A; white blood cells; and zinc protoporphyrin. Salts, sugar, protein, fat, vitamins and hormones naturally occurring in blood or interstitial fluids can also constitute analytes in certain embodiments. The analyte can be naturally present in the biological fluid, for example, a metabolic product, a hormone, an antigen, an antibody, and the like. Alternatively, the analyte can be introduced into the body, for example, a contrast agent for imaging, a radioisotope, a chemical agent, a fluorocarbon-based synthetic blood, or a drug or pharmaceutical composition, including but not limited to insulin; ethanol; cannabis (marijuana, tetrahydrocannabinol, hashish); inhalants (nitrous oxide, amyl nitrite, butyl nitrite, chlorohydrocarbons, hydrocarbons); cocaine (crack cocaine); stimulants (amphetamines, methamphetamines, Ritalin, Cylert, Preludin, Didrex, PreState, Voranil, Sandrex, Plegine); depressants (barbituates, methaqualone, tranquilizers such as Valium, Librium, Miltown, Serax, Equanil, Tranxene); hallucinogens (phencyclidine, lysergic acid, mescaline, peyote, psilocybin); narcotics (heroin, codeine, morphine, opium, meperidine, Percocet, Percodan, Tussionex, Fentanyl, Darvon, Talwin, Lomotil); designer drugs (analogs of fentanyl, meperidine, amphetamines, methamphetamines, and phencyclidine, for example, Ecstasy); anabolic steroids; and nicotine. The metabolic products of drugs and pharmaceutical compositions are also contemplated analytes. Analytes such as neurochemicals and other chemicals generated within the body can also be analyzed, such as, for example, ascorbic acid, uric acid, dopamine, noradrenaline, 3-methoxytyramine (3MT), 3,4-dihydroxyphenylacetic acid (DOPAC), homovanillic acid (HVA), 5-hydroxytryptamine (5HT), and 5-hydroxyindoleacetic acid (FHIAA).

The terms "operably connected" and "operably linked" as used herein are broad terms and are used in their ordinary sense, including, without limitation, to refer to one or more components linked to one or more other components. The terms can refer to a mechanical connection, an electrical connection, or a connection that allows transmission of signals between the components. For example, one or more electrodes can be used to detect the amount of analyte in a sample and to convert that information into a signal; the signal can then be transmitted to a circuit. In such an example, the electrode is "operably linked" to the electronic circuitry.

The term "host" as used herein is a broad term and is used in its ordinary sense, including, without limitation, to refer to mammals, particularly humans.

The term "exit-site" as used herein is a broad term and is used in its ordinary sense, including, without limitation, to refer to the area where a medical device (for example, a sensor arid/or needle) exits from the host's body.

The phrase "continuous (or continual) analyte sensing" as used herein is a broad term and is used in its ordinary sense, including, without limitation, to refer to the period in which monitoring of analyte concentration is continuously, continually, and or intermittently (regularly or irregularly) performed, for example, about every 5 to 10 minutes.

The term "electrochemically reactive surface" as used herein is a broad term and is used in its ordinary sense, including, without limitation, to refer to the surface of an electrode where an electrochemical reaction takes place. For example, a working electrode measures hydrogen peroxide produced by the enzyme-catalyzed reaction of the analyte detected, which reacts to create an electric current. Glucose analyte can be detected utilizing glucose oxidase, which produces $H_2O_2$ as a byproduct. $H_2O_2$ reacts with the surface of the working electrode, producing two protons ($2H^+$), two electrons ($2e^-$) and one molecule of oxygen ($O_2$), which produces the electronic current being detected. In the case of the counter electrode, a reducible species, for example, $O_2$ is reduced at the electrode surface in order to balance the current being generated by the working electrode.

The term "sensing region" as used herein is a broad term and is used in its ordinary sense, including, without limitation, to refer to the region of a monitoring device responsible for the detection of a particular analyte. The sensing region generally comprises a non-conductive body, a working electrode (anode), a reference electrode (optional), and/or a counter electrode (cathode) passing through and secured within the body forming electrochemically reactive surfaces on the body and an electronic connective means at another location on the body, and a multi-domain membrane affixed to the body and covering the electrochemically reactive surface.

The terms "electronic connection" and "electrical connection" as used herein is a broad term and is used in its ordinary sense, including, without limitation, to refer to any electronic connection known to those in the art that can be utilized to interface the sensing region electrodes with the electronic circuitry of a device, such as mechanical (for example, pin and socket) or soldered electronic connections.

The term "domain" as used herein is a broad term and is used in its ordinary sense, including, without limitation, to refer to a region of the membrane system that can be a layer, a uniform or non-uniform gradient (for example, an anisotropic region of a membrane), or a portion of a membrane.

The term "distal to" as used herein is a broad term and is used in its ordinary sense, including, without limitation, the spatial relationship between various elements in comparison to a particular point of reference.

The term "proximal to" as used herein is a broad term and is used in its ordinary sense, including, without limitation, the spatial relationship between various elements in comparison to a particular point of reference.

The terms "in vivo portion" and "distal portion" as used herein are broad terms and are used in their ordinary sense, including, without limitation, to refer to the portion of the device (for example, a sensor) adapted for insertion into and/or existence within a living body of a host.

The terms "ex vivo portion" and "proximal portion" as used herein are broad terms and are used in their ordinary sense, including, without limitation, to refer to the portion of the device (for example, a sensor) adapted to remain and/or exist outside of a living body of a host.

The term "intermediate portion" as used herein is a broad term and is used in its ordinary sense, including, without limitation, to refer to a portion of the device between a distal portion and a proximal portion.

The terms "transdermal" and "transcutaneous" as used herein are broad terms and is used in their ordinary sense, including, without limitation, to refer to extending through the skin of a host. For example, a transdermal analyte sensor is one that extends through the skin of a host.

The term "hardening" as used herein is a broad term and is used in its ordinary sense, including, without limitation, to refer to an increase in hardness of a metal induced by a process such as hammering, rolling, drawing, or the like.

The term "softening" as used herein is a broad term and is used in its ordinary sense, including, without limitation, to refer to an increase in softness of a metal induced by processes such as annealing, tempering, or the like.

The term "tempering" as used herein is a broad term and is used in its ordinary sense, including, without limitation, to refer to the heat-treating of metal alloys, particularly steel, to reduce brittleness and restore ductility.

The term "annealing" as used herein is a broad term and is used in its ordinary sense, including, without limitation, to refer to the treatment of a metal or alloy by heating to a predetermined temperature, holding for a certain time, and then cooling to room temperature to improve ductility and reduce brittleness.

The term "stiff" as used herein is a broad term and is used in its ordinary sense, including, without limitation, to refer to a material not easily bent, lacking in suppleness or responsiveness. In the preferred embodiments, the degree of stiffness can be relative to other portions of the device.

The term "flexible" as used herein is a broad term and is used in its ordinary sense, including, without limitation, to refer to a material that is bendable, pliable, or yielding to influence. In the preferred embodiments, the degree of flexibility can be relative to other portions of the device.

The devices of the preferred embodiments include transdermal medical devices, such as transcutaneous sensor assemblies, with variable stiffness configured along at least a portion of the device. In one aspect of the preferred embodiments, a transcutaneous sensor assembly is provided, including a sensor for sensing an analyte linked to a housing for mounting on the skin of the host. The housing houses an electronics unit associated with the sensor and is adapted for secure adhesion to the host's skin.

Transcutaneous Sensors

Figure 1B:
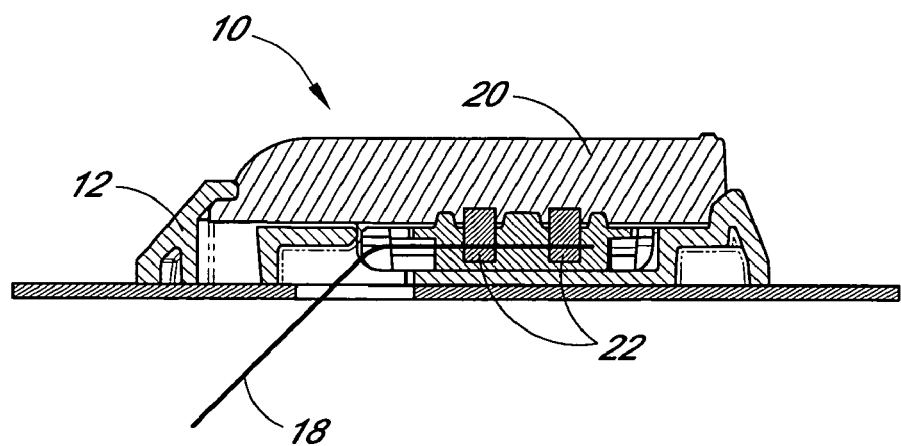
FIG. 1B is a side cross-sectional view of the transcutaneous sensor assembly of FIG. 1A.

FIGS. 1A and 1B are perspective and side cross-sectional views of a transcutaneous sensor assembly 10 of a preferred embodiment. The sensor system includes a housing 12 and preferably includes an adhesive material 14 on its backside 16 for adhesion to a host's skin. A sensor 18 extends from the housing and is adapted for transdermal insertion through the skin of the host. The sensor portion can be configured for insertion into a variety of in vivo locations, including subcutaneous, venous, or arterial locations, for example. One or more contacts 22 are configured to provide secure electrical contact between sensor 18 and an electronics unit 20. The housing 12 is designed to maintain the integrity of the sensor in the host so as to reduce or eliminate translation of motion between the housing 12, the host, and/or the sensor 18.

In general, the sensor includes at least one electrode configured for measuring an analyte. In one embodiment, the sensor 18 includes at least two electrodes: a working electrode and at least one additional electrode, which can function as a counter and/or reference electrode. Preferably, the working electrode comprises a wire formed from a conductive material, such as platinum, palladium, graphite, gold, carbon, conductive polymer, or the like. In some embodiments, the wire is formed from a bulk material, or alternatively, a composite of two or more metals and/or insulators (e.g., platinum plated steel). The working electrode is configured to measure the concentration of an analyte. The reference electrode, which can function as a reference electrode alone, or as a dual reference and counter electrode, is preferably formed from silver, silver/silver chloride, or the like. In preferred embodiments, the reference electrode is twisted with or around the working electrode; however other configurations for the working electrode and the reference electrode are also possible, for example juxtapositioned, adjacent, coaxial, concentric, interdigitated, spiral-wound, or the like.

In some alternative embodiments, additional electrodes can be included within the assembly. For example, a three-electrode system (working, reference, and counter electrodes) and/or a system including an additional working electrode (which can be used to generate oxygen or can be configured as a baseline subtracting electrode, for example) can be employed. Other sensor/wire/electrode configurations (for example one, two, three, four, or more wires and/or electrode configurations) are also within the scope of the preferred embodiments. For example, U.S. Pat. No. 6,613,379 to Ward et al. describes a bundle of wires around which a counter electrode is deposed and configured for measuring an analyte, and U.S. Pat. No. 6,329,161 to Heller et al. describes a single wire electrode configured for measuring an analyte. Any such configuration adapted for transcutaneous analyte measurement can be configured with a variable stiffness in accordance with the preferred embodiments.

In some embodiments (for example, enzymatic-based sensors), a membrane system is disposed over some or all of the electroactive surfaces of the sensor 18 (working and/or reference electrodes) and provides one or more of the following functions: 1) protection of the exposed electrode surface from the biological environment; 2) diffusion resistance (limitation) of the analyte; 3) a catalyst for enabling an enzymatic reaction; 4) hindering or blocking passage of interfering species; and 5) hydrophilicity at the electrochemically reactive surfaces of the sensor interface, such as is described in co-pending U.S. patent application Ser. No.11/077,715, filed on even date herewith and entitled "TRANSCUTANEOUS ANALYTE SENSOR".

The electronics unit 20 can be integral with or removably attached to the housing 12, and includes hardware, firmware and/or software that enable measurement of levels of the analyte via the sensor 18. For example, the electronics unit 20 comprises a potentiostat, a power source for providing power to the sensor, other components useful for signal processing, and preferably an RF module for transmitting data from the electronics unit 20 to a receiver. Electronics can be affixed to a printed circuit board (PCB), or the like, and can take a variety of forms. For example, the electronics can take the form of an integrated circuit (IC), such as an application-specific integrated circuit (ASIC), a microcontroller, or a processor. Preferably, the electronics unit 20 houses the sensor electronics, which comprise systems and methods for processing sensor analyte data. Examples of systems and methods for processing sensor analyte data are described in more detail below and in co-pending U.S. application Ser. No. 10/633,367 filed Aug. 1, 2003 entitled, "SYSTEM AND METHODS FOR PROCESSING ANALYTE SENSOR DATA."

Co-pending U.S. patent application Ser. No. 11/077,715, filed on even date herewith, and entitled, "TRANSCUTANEOUS ANALYTE SENSOR," describes an embodiment of a transcutaneous analyte sensor that benefits from variable stiffness. Variable stiffness configurations along at least a portion of the device can be employed with devices such as are described in U.S. Pat. No. 6,613,379 to Ward et al., U.S. Pat. No. 6,122,536 to Sun et al., U.S. Pat. No. 6,329,161 to Heller et al., U.S. Pat. No. 6,477,395 to Schulman, and U.S. Pat. No. 4,671,288 to Gough.

Variable Stiffness

Conventional transcutaneous devices can be subject to motion artifact associated with host movement when the host is using the device. For example, in the example of a transcutaneous analyte sensor such as described above, various movements on the sensor (for example, relative movement within and between the subcutaneous space, dermis, skin, and external portions of the sensor) create stresses on the device, which are known to produce artifacts on the sensor signal.

Accordingly, the design considerations (for example, stress considerations) vary for different sections of a transcutaneous medical device. For example, certain portions of the device can benefit in general from greater flexibility as the portion of the device encounters greater mechanical stresses caused by movement of the tissue within the patient and relative movement between the in vivo and ex vivo portions of the sensor. Additionally or alternatively, certain portions of the device can benefit in general from a stiffer, more robust design to ensure structural integrity and/or reliable electrical connections. Additionally, in some embodiments wherein an insertion device (for example, needle that aids in insertion) is retracted over the device, a stiffer design can enable minimized crimping and/or easy retraction. Thus, by designing greater flexibility into the some portions of the device, the flexibility can compensate for movement and noise associated therewith; and by designing greater stiffness into other portions, column strength (for retraction of the needle over the sensor), electrical connections, and structural integrity can be enhanced.

Figure 2:
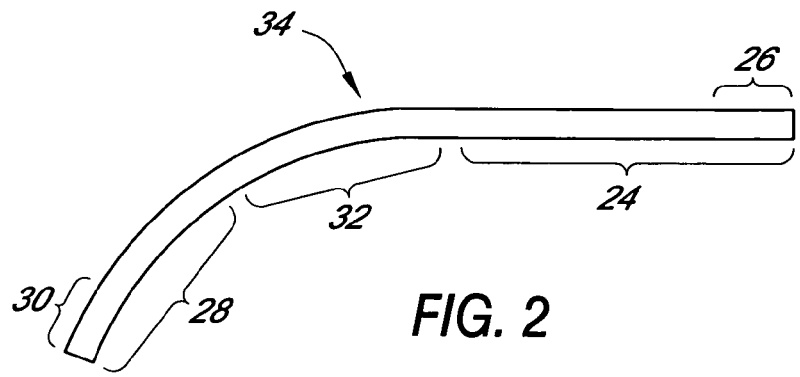
FIG. 2 is a schematic side view of a transcutaneous medical device.

FIG. 2 is a side schematic view of a transcutaneous medical device 34, such as illustrated as the transcutaneous analyte sensor 18 of FIG. 1. In general, a transcutaneous medical device 34, can be divided into three zones, a proximal portion 24 with a proximal tip 26, a distal portion 28 with a distal tip 30, and an intermediate portion 32. The preferred embodiments can employ a variety of configurations that provide variable stiffness along at least a portion of the device in order to overcome disadvantages of conventional transcutaneous devices. Although the following description is focused on an embodiment of a transcutaneous analyte sensor, one skilled in the art can appreciate that the variable stiffness of the preferred embodiments can be implemented with a variety of transcutaneous medical devices.

Generally, the proximal portion 24 is adapted to remain above the host's skin after device insertion and operably connects to a housing ex vivo, for example. The proximal portion 24 typically provides the mechanical and/or electrical connections of the device to housings, electronics, or the like. The proximal portion includes a proximal tip 26 on an end thereof. It is noted that the terms "proximal portion," "ex vivo portion," and "proximal tip" do not necessarily imply an exact length or section, rather is generally a section that is more proximal than distal relative to the housing. In some embodiments, the proximal portion (or proximal tip) is stiffer than at least one of the intermediate and distal portions.

Generally, the distal portion 28 of the sensor is adapted for insertion under the host's skin, and is also referred to as the in vivo portion. The distal portion 28 typically provides the device function in vivo, and therefore encounters stresses caused by insertion of the device into the host's tissue and subsequent movement of the tissue of the patient. The distal portion includes a distal tip 30 on an end thereof. It is noted that the terms "distal portion," "in vivo portion," and "distal tip" do not necessarily imply an exact length or section, rather is generally a section that is more distal than proximal relative to the housing. In some embodiments, the distal portion is more flexible than at least one of the intermediate and proximal portions. In some embodiments, the distal tip is less flexible than at least one of the remaining (non-tip) distal portion, the intermediate portion, and the proximal portion.

Generally, the intermediate portion 32 is located between the proximal portion 24 and the distal portion and may include portions adapted for insertion or adapted to remain above the skin. The intermediate portion 32 typically provides a transition between the in vivo and ex vivo portions, and can incur stresses caused by relative movement between the in vivo and ex vivo portions of the sensor, for example. It is noted that the term "intermediate portion" does not necessarily imply an exact length or section, rather is generally a section that in-between the proximal and distal portions. In some embodiments, the intermediate portion is more flexible than one or both of the distal and proximal portions.

Figure 3A:
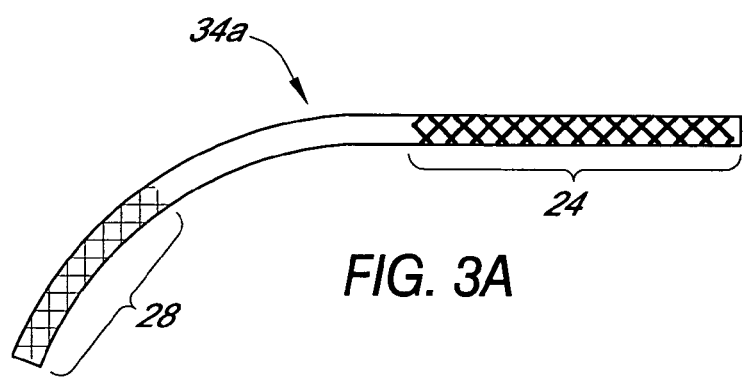
FIG. 3A is a schematic side view of a first transcutaneous medical device having a variable stiffness.

FIG. 3A is a side schematic view of a transcutaneous medical device 34a in one embodiment adapted for insertion through the skin of a host. In this embodiment, the device 34a is designed with greater flexibility generally in a distal portion 28 (relative to intermediate and/or proximal portions), which is illustrated by light cross-hatching in the distal portion of the device. Stated in another way, the device is designed with a greater stiffness generally in the proximal portion 24 than the intermediate and/or the distal portions, which is illustrated by heavy cross-hatching in the proximal portion 24 of the device. In some embodiments, the intermediate portion includes a flexibility substantially similar to that of the distal portion; in other embodiments, the intermediate portion gradually transitions between the flexibility of the distal portion and the stiffness of the proximal portion. For example, in situations wherein movement of the tissue within the patient and relative movement between the in vivo and ex vivo portions of the device create stresses on the device, greater flexibility in a distal portion (relative to intermediate and/or proximal portions) can provide relief from these mechanical stresses, protecting both the integrity of the sensor and the host tissue. Additionally or alternatively, in situations wherein mechanical and/or electrical connections are required for accurate device function, greater stiffness in the proximal portion 24 (and/or the proximal tip) of the device can increase the stability and reliability of these connections. Thus, the ex-vivo or proximal portion 24 of the sensor is configured for stable connection to the electronics and can additionally be configured to receive an insertion device (such as a needle that aids in sensor insertion) upon retraction from the skin of the host (see co-pending U.S. patent application Ser. No. 11/077,715, filed on even date herewith and entitled "TRANSCUTANEOUS ANALYTE SENSOR").

Figure 3B:
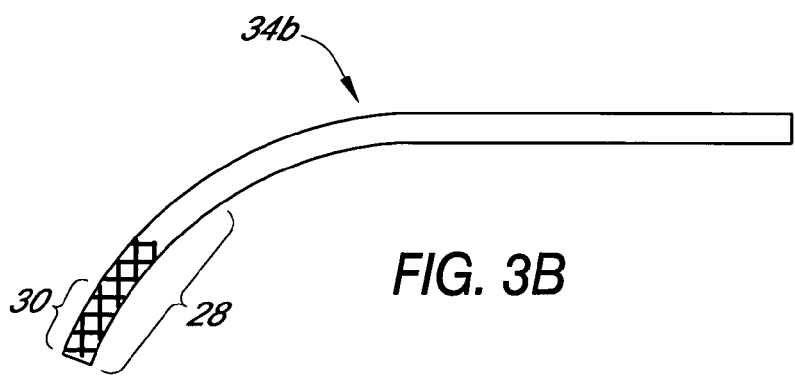
FIG. 3B is a schematic side view of a second transcutaneous medical device having a variable stiffness.

FIG. 3B is a side schematic view of a transcutaneous medical device 34b of a preferred embodiment adapted to be inserted through the skin of a host. In this embodiment, the device is designed with an increased stiffness at a distal tip 30 (or a distal portion 28) of the device (relative to intermediate and/or proximal portions) in order to provide increased strength and/or structural integrity to the tip, which is illustrated by heavy cross-hatching. In some situations, the device is inserted into the host such that a tunnel is formed therein. When the device abuts the tunnel end, increased stress to the distal tip can occur. This increased stress can cause the device to bend, resulting in malfunctioning of the device.

In some embodiments, this increased stiffness is designed into the device by creating a greater hardness of the distal tip of the device, for example, by annealing or coating the device. In one embodiment of a transcutaneous analyte sensor as described above with reference to FIG. 1, a higher pitch of the helically wound reference electrode for at least a few windings at a distal end of the reference electrode creates a relative stiffness of the distal portion or tip of the device. It is believed that a stiffer distal portion or tip advantageously provides increased stability, column strength, and proper placement of the device in the host.

Figure 3C:
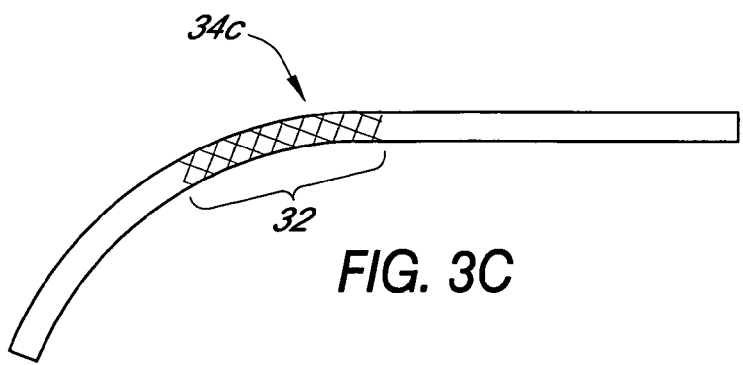
FIG. 3C is a schematic side view of a third transcutaneous medical device having a variable stiffness.

FIG. 3C is a side schematic view of a transcutaneous medical device 34c in yet another embodiment adapted to be inserted through the skin of a host. In this embodiment, the device 34c is designed with an increased flexibility at an intermediate portion 32 thereof. Namely, the intermediate portion of the device is designed to absorb shock between the proximal and distal portions, for example, such that movement of the ex vivo portion of the device does not substantially translate to the in vivo portion of the device (and vice versa). In some aspects of this embodiment, the distal portion is designed with a flexibility similar to that of the intermediate portion. In some aspects of this embodiment, the flexibility gradually changes from the distal portion to the proximal portion, including a relatively flexible intermediate portion 32.

In some embodiments, any combination of the above described relatively stiff or flexible portions can be designed into a transcutaneous medical device. In fact, a variety of additional stiff and/or flexible portions can be incorporated into the distal and/or proximal portions of the device without departing from the scope of the preferred embodiments. The flexibility and/or stiffness can be stepped, gradual, or any combination thereof.

The variable stiffness (flexibility) of the preferred embodiments can be provided by a variable pitch of any one or more wires of the device, a variable cross-section of any one or more wires of the device, and/or a variable hardening and/or softening of any one or more wires of the device, for example, as is described in more detail below.

Figure 4A:
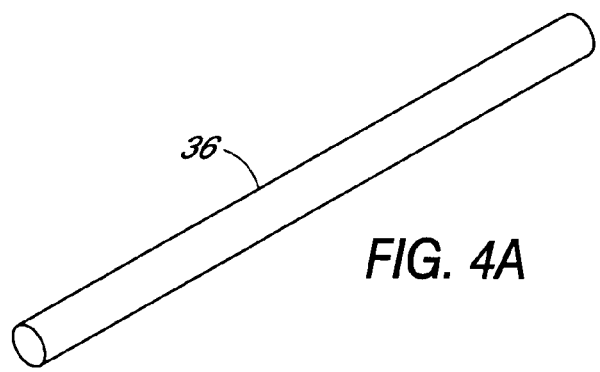
FIGS. 4A to 4D are perspective and side views of a first variable stiffness wire for use with a transcutaneous analyte sensor.

FIGS. 4A to 4D are perspective and side views of a variable stiffness wire used in a transcutaneous medical device, such as an analyte sensor. In FIG. 4A, a wire 36 is shown, which can represent the working electrode or reference electrode of the embodiment described with reference to FIG. 1, for example. Alternatively, the wire 36 can represent one or more wires of a multiple wire sensor (examples of each are described above). The variable stiffness wire described herein can be employed in a transcutaneous medical device to provide variable stiffness along a portion of the length of the device, such as in an analyte sensor.

Figure 4B:
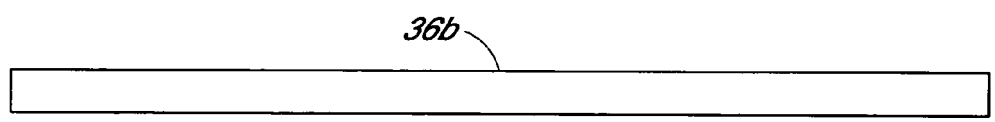

FIG. 4B is a side view of a variable stiffness wire 36b wherein physical processing of the distal, intermediate, and/or proximal portions of the wire provide for variability of the stiffness of the wire. In some embodiments, some portion (for example, the distal portion) of the wire is softened using a process such as annealing or tempering. In some embodiments, some portion (for example, the proximal portion) of the wire is hardened using a process such as drawing or rolling. In some embodiments, some combination of softening and hardening as described herein are employed to provide variable stiffness of the wire. In the embodiment described with reference to FIG. 1, including a working electrode and a reference electrode, the working electrode can be hardened and/or softened to provide for the variable stiffness of one or more portions of the device, such as is described in more detail elsewhere herein. Another alternative embodiment provides a varying modulus of elasticity of the material to provide the variable stiffness of the preferred embodiments.

Figure 4C:

FIG. 4C is a side view of an alternative variable stiffness wire 36c, wherein the wire has a gradually increasing or decreasing diameter along its length. The variability in diameter can be produced by physical or chemical processes, for example, by grinding, machining, rolling, pulling, etching, drawing, swaging, or the like. In this way, a transcutaneous analyte sensor, or other transcutaneous medical device, can be produced having a variable stiffness. In the embodiment described with reference to FIG. 1, for example, including a working electrode and a reference electrode, the working electrode can be formed with a variable diameter to provide for the variable stiffness of one or more portions of the device, such as described in more detail elsewhere herein.

Figure 4D:
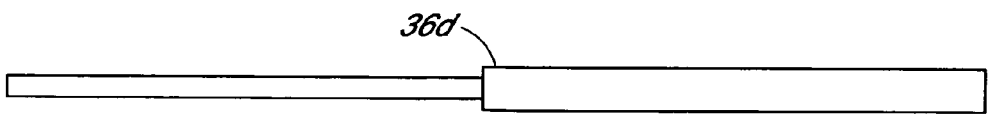

FIG. 4D is a side view of another alternative variable stiffness wire 36d, wherein the wire is step increased or decreased to provide two (or more) different flexibilities of the wire. The wire can be stepped by physical or chemical processes known in the art, such as described with reference to FIG. 4C. In this way, a transcutaneous analyte sensor, or other transcutaneous medical device, can be produced with a variable stiffness. A noted advantage of the smaller diameter configurations of FIGS. 4C and 4D include reduced sizing of the in vivo portion of the device, which is believed to be more comfortable for the patient and to induce less invasive trauma around the device, thereby providing an optimized device design.

Figure 5A:
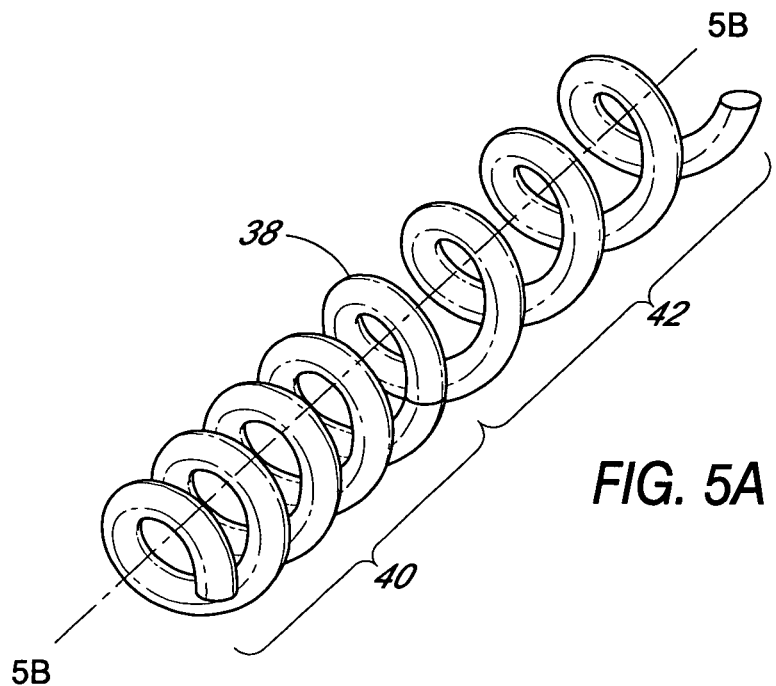
FIGS. 5A and 5B are perspective and cross-sectional views of a second variable stiffness wire for use with a transcutaneous analyte sensor.
Figure 5B:
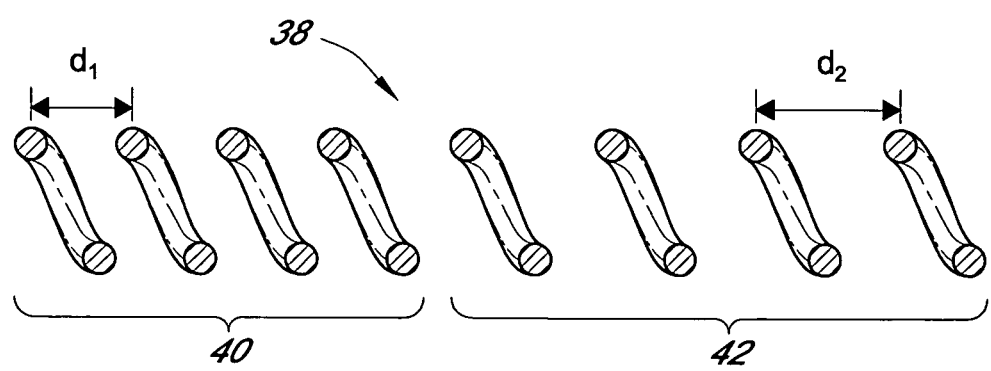

FIGS. 5A and 5B are perspective and cross-sectional views of a variable stiffness wire 38 in an alternative embodiment representing any one or more wires associated with a transcutaneous medical device, such as an analyte sensor. For example, the wire 38 can represent the reference electrode of the embodiment described with reference to FIG. 1. Alternatively, the wire 38 can represent the wire of a single or multiple wire sensor (examples of each are described above).

In this embodiment, two distinct portions 40, 42 are shown with first and second pitches; however, the illustration is not meant to be limiting and the variable pitch can include any number of gradual portions, stepped portions, or the like. Additionally, the variable pitch and/or helical configuration can be provided on only a portion of the wire or on the entire length of the wire, and can include any number of pitch changes. In this embodiment, a first portion 40 is wound to have relatively closely spaced coils, namely, a high helix pitch, whereas a second 42 portion is not subjected to high stress levels and can include coils wound with a lower helix pitch. The helix pitch is defined as the number of coils of the wire core per unit length of the device, or the distance between the coils.

FIG. 5B is a cross-sectional view along line B-B of the device of FIG. 5A, illustrating a first distance $d_1$ between the coils in the first portion 40 and a second distance $d_2$ between the coils in the second portion 42, wherein $d_2$ is greater than $d_1$. Thus, the wire has a variable stiffness attributable to the varying helix pitch over the length of the sensor. In this way, portions of a device having wire with a low helix pitch are designed with greater flexibility and are more able to handle the stresses associated with motion of the sensor while portions of the sensor having wire with a high helix pitch are designed with more stiffness and provide more stability for the sensor in the housing. Any portions (proximal, intermediate, and/or distal portions (or tips)) can be designed with a variable pitch to impart variable stiffness.

Figure 6A:
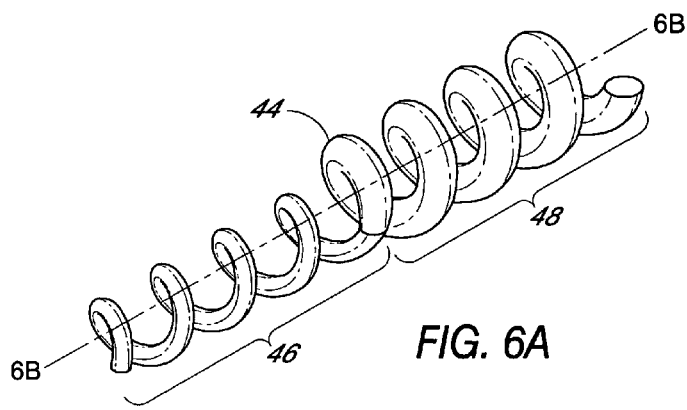
FIGS. 6A and 6B are perspective and cross-sectional views of a third variable stiffness wire suitable for use with a transcutaneous analyte sensor.
Figure 6B:
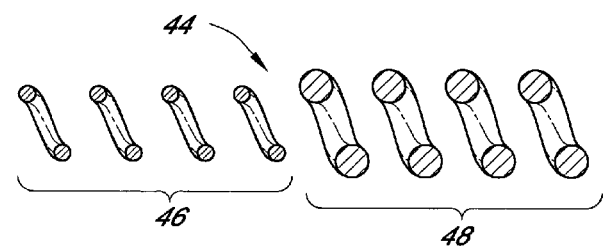

FIGS. 6A and 6B are perspective and longitudinal views of a variable stiffness wire 44 in yet another alternative embodiment representing any one or more wires associated with a transcutaneous medical device, such as an analyte sensor. For example, the wire 44 can be the reference electrode of the embodiment described with reference to FIG. 1. Alternatively, the wire 44 can be a working electrode, and/or one or more wires of a multiple wire sensor (examples of each are described above).

In this embodiment, two distinct portions 46, 48 are shown with first and second wire diameters that provide a variable cross-section; however, the illustration is not meant to be limiting and the variable cross-section can be gradual, stepped, or the like. Additionally, the variable cross-section and/or helical configuration can be provided on only a portion of the wire or on the entire length of the wire, and can include any number of cross-section changes. In this embodiment, the helically wound wire is designed with a variable cross-sectional area over the length of the sensor from a small cross-sectional area in the first portion 46 to a larger cross-sectional area in the second portion 48.

FIG. 6B is a cross-sectional view along line B-B of the device of FIG. 6A, revealing cross-sectional information about one or more wires that make up the coil, including a first cross-section $x_1$ of the wire in the first portion 20 and a second cross-section $x_2$ of the wire in the second portion 48, wherein $x_2$ is greater than $x_1$. Thus, the device of this embodiment has a variable stiffness attributable to the varying cross-section over the length of the sensor. In this way, first portion 46 has a smaller cross-sectional area and is therefore more flexible and capable of withstanding the stresses associated with patient movement, for example; while the second portion 48 has a larger cross-sectional area and is stiffer and provides more stability and column strength desirable for mechanical and electrical connections, for example.

The transcutaneous analyte sensor of FIG. 1 includes a helical configuration. The helical surface topography of the reference electrode surrounding the working electrode not only provides electrochemical functionality, but can also provide anchoring within the host tissue. The device preferably remains substantially stationary within the tissue of the host, such that migration or motion of the sensor with respect to the surrounding tissue is minimized. Migration or motion can cause inflammation at the sensor implant site due to irritation and can also cause noise on the sensor signal due to motion-related artifact, for example. Therefore, it can be advantageous to provide an anchoring mechanism that provides support for the sensor in vivo portion to avoid or minimize the above-mentioned problems. Combining advantageous sensor geometry with advantageous anchoring minimizes additional parts in the device, and allows for an optimally small or low profile design of the sensor. Additionally or alternatively, anchoring can be provided by prongs, spines, barbs, wings, hooks, rough surface topography, gradually changing diameter, or the like, which can be used alone or in combination with the helical surface topography to stabilize the sensor within the subcutaneous tissue.

EXAMPLE

Figure 7:
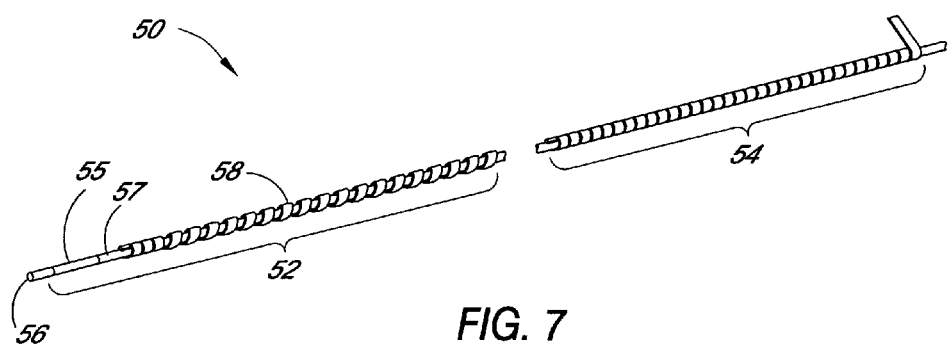
FIG. 7 is an expanded view of distal and proximal portions of a transcutaneous sensor in one example.

FIG. 7 is an expanded view of distal and proximal portions of a transcutaneous sensor 50 in one example. FIG. 7 illustrates a sensor 50 broken away between its distal portion 52 and proximal portion 54, representing any length or configuration there between. In the illustrated embodiment, the sensor 50 includes two electrodes: a working electrode 56 and one additional electrode, which can function as a counter and/or reference electrode, hereinafter referred to as the reference electrode 58. Each electrode is formed from a fine wire with a diameter of approximately 0.0045 inches.

The working electrode 56 comprises a platinum wire and is configured and arranged to measure the concentration of an analyte. In this example of an enzymatic electrochemical sensor, the working electrode measures the hydrogen peroxide produced by an enzyme catalyzed reaction of the analyte being detected and creates a measurable electronic current (for example, detection of glucose utilizing glucose oxidase produces $H_2O_2$ peroxide as a by product, $H_2O_2$ reacts with the surface of the working electrode producing two protons ($2H^+$), two electrons ($2e^-$) and one molecule of oxygen ($O_2$) which produces the electronic current being detected).

The working electrode 56 is covered with an insulator 57, e.g., Parylene, which is vapor-deposited on the working electrode. Parylene is an advantageous conformal coating because of its strength, lubricity, and electrical insulation properties; however, a variety of other insulating materials can also be used, for example, fluorinated polymers, polyethyleneterephthalate, polyurethane, polyimide, or the like. The reference electrode 58, which can function as a counter electrode alone, or as a dual reference and counter electrode, is preferably silver or a silver-containing material. In this example, the reference electrode 58 is helically twisted around the working electrode 56. A window 55 is formed on the insulating material to expose an electroactive surface of the working electrode 56. Other methods and configurations for exposing electroactive surfaces can also be employed.

In this example, the reference electrode 58 is wound with a variable pitch that creates a variable stiffness along the length of the sensor 50. Namely, the sensor 50 is designed with a greater stiffness generally in the proximal portion 54 than the intermediate and/or the distal portions 52. However, an increased stiffness of a section of the distal portion 52, shown adjacent to the window 55 wherein the reference electrode 58 includes a higher helix pitch for a few windings, provides increased strength in a high stress location, without inhibiting the overall flexibility of the distal portion 52. It is believed that in situations wherein movement of the tissue within the patient and relative movement between the in vivo and ex vivo portions of the device create stresses on the device, greater flexibility in a distal portion (and optionally in the intermediate portion relative to the proximal portion) can provide relief from these mechanical stresses, protecting both the integrity of the sensor and the host tissue. Additionally or alternatively, in situations wherein mechanical and/or electrical connections are employed for accurate function, greater stiffness in the proximal portion (and/or the proximal tip) of the device can increase the stability and reliability of these connections. Additionally, this exemplary configuration is advantageous for the reasons described above, and further provides an enhanced mechanical stability by the distribution of forces of the helical wire along the straight wire.

Methods and devices that are suitable for use in conjunction with aspects of the preferred embodiments are disclosed in U.S. Pat. No. 4,994,167 issued Feb. 19, 1991 and entitled "BIOLOGICAL FLUID MEASURING DEVICE"; U.S. Pat. No. 4,757,022 issued February Jul. 12, 1988 and entitled "BIOLOGICAL FLUID MEASURING DEVICE"; U.S. Pat. No. 6,001,067 issued February Dec. 14, 1999 and entitled "DEVICE AND METHOD FOR DETERMINING ANALYTE LEVELS"; U.S. Pat. No. 6,741,877 issued February May 25, 2004 and entitled "DEVICE AND METHOD FOR DETERMINING ANALYTE LEVELS"; U.S. Pat. No. 6,702,857 issued February Mar. 9, 2004 and entitled "MEMBRANE FOR USE WITH IMPLANTABLE DEVICES"; and U.S. Pat. No. 6,558,321 issued February May 6, 2003 and entitled "SYSTEMS AND METHODS FOR REMOTE MONITORING AND MODULATION OF MEDICAL DEVICES." Methods and devices that are suitable for use in conjunction with aspects of the preferred embodiments are disclosed in co-pending U.S. application Ser. No. 10/991,353 filed Nov. 16, 2004 and entitled "AFFINITY DOMAIN FOR ANALYTE SENSOR"; U.S. application Ser. No. 11/055,779 filed Feb. 9, 2005 and entitled "BIOINTERFACE WITH MACRO-AND-MICRO-ARCHITECTURE"; U.S. application Ser. No. 11/004,561 filed Dec. 3, 2004 and entitled "CALIBRATION TECHNIQUES FOR A CONTINUOUS ANALYTE SENSOR"; U.S. application Ser. No. 11/034,343 filed Jan. 11, 2005 and entitled "COMPOSITE MATERIAL FOR IMPLANTABLE DEVICE"; U.S. application Ser. No. 09/447,227 filed Nov. 22, 1999 and entitled "DEVICE AND METHOD FOR DETERMINING ANALYTE LEVELS"; U.S. application Ser. No. 11/021,046 filed Dec. 22, 2004 and entitled "DEVICE AND METHOD FOR DETERMINING ANALYTE LEVELS"; U.S. application Ser. No. 09/916,858 filed Jul. 27, 2001 and entitled "DEVICE AND METHOD FOR DETERMINING ANALYTE LEVELS"; U.S. application Ser. No. 11/039,269 filed Jan. 19, 2005 and entitled "DEVICE AND METHOD FOR DETERMINING ANALYTE LEVELS"; U.S. application Ser. No. 10/897,377 filed Jul. 21, 2004 and entitled "ELECTROCHEMICAL SENSORS INCLUDING ELECTRODE SYSTEMS WITH INCREASED OXYGEN GENERATION"; U.S. application Ser. No. 10/897,312 filed Jul. 21, 2004 and entitled "ELECTRODE SYSTEMS FOR ELECTROCHEMICAL SENSORS"; U.S. application Ser. No. 10/838,912 filed May 3, 2004 and entitled "IMPLANTABLE ANALYTE SENSOR"; U.S. application Ser. No. 10/838,909 filed May 3, 2004 and entitled "IMPLANTABLE ANALYTE SENSOR"; U.S. application Ser. No. 10/838,658 filed May 3, 2004 and entitled "IMPLANTABLE ANALYTE SENSOR"; U.S. application Ser. No. 11/034,344 filed Jan. 11, 2005 and entitled "IMPLANTABLE DEVICE WITH IMPROVED RADIO FREQUENCY CAPABILITIES"; U.S. application Ser. No. 10/896,772 filed Jul. 21, 2004 and entitled "INCREASING BIAS FOR OXYGEN PRODUCTION IN AN ELECTRODE SYSTEM"; U.S. application Ser. No. 10/789,359 filed Feb. 26, 2004 and entitled "INTEGRATED DELIVERY DEVICE FOR CONTINUOUS GLUCOSE SENSOR"; U.S. application Ser. No. 10/991,966 filed Nov. 17, 2004 and entitled "INTEGRATED RECEIVER FOR CONTINUOUS ANALYTE SENSOR"; U.S. application Ser. No. 10/646,333 filed Aug. 22, 2003 and entitled "OPTIMIZED SENSOR GEOMETRY FOR AN IMPLANTABLE GLUCOSE SENSOR"; U.S. application Ser. No. 10/896,639 filed Jul. 21, 2004 and entitled "OXYGEN ENHANCING MEMBRANE SYSTEMS FOR IMPLANTABLE DEVICES"; U.S. application Ser. No. 10/647,065 filed Aug. 22, 2003 and entitled "POROUS MEMBRANES FOR USE WITH IMPLANTABLE DEVICES"; U.S. application Ser. No. 10/896,637 filed Jul. 21, 2004 and entitled "ROLLED ELECTRODE ARRAY AND ITS METHOD FOR MANUFACTURE"; U.S. application Ser. No. 09/916,711 filed Jul. 27, 2001 and entitled "SENSOR HEAD FOR USE WITH IMPLANTABLE DEVICE"; U.S. application Ser. No. 11/021,162 filed Dec. 22, 2004 and entitled "SENSOR HEAD FOR USE WITH IMPLANTABLE DEVICES"; U.S. application Ser. No. 11/007,920 filed Dec. 8, 2004 and entitled "SIGNAL PROCESSING FOR CONTINUOUS ANALYTE SENSOR"; U.S. application Ser. No. 10/695,636 filed Oct. 28, 2003 and entitled "SILICONE COMPOSITION FOR BIOCOMPATIBLE MEMBRANE"; U.S. application Ser. No. 11/038,340 filed Jan. 18, 2005 and entitled "SYSTEM AND METHODS FOR PROCESSING ANALYTE SENSOR DATA"; U.S. application Ser. No. 11/007,635 filed Dec. 7, 2004 and entitled "SYSTEMS AND METHODS FOR IMPROVING ELECTROCHEMICAL ANALYTE SENSORS"; U.S. application Ser. No. 10/885,476 filed Jul. 6, 2004 and entitled "SYSTEMS AND METHODS FOR MANUFACTURE OF AN ANALYTE-MEASURING DEVICE INCLUDING A MEMBRANE SYSTEM"; U.S. application Ser. No. 10/648,849 filed Aug. 22, 2003 and entitled "SYSTEMS AND METHODS FOR REPLACING SIGNAL ARTIFACTS IN A GLUCOSE SENSOR DATA STREAM"; U.S. application Ser. No. 10/153,356 filed May 22, 2002 and entitled "TECHNIQUES TO IMPROVE POLYURETHANE MEMBRANES FOR IMPLANTABLE GLUCOSE SENSORS"; U.S. application Ser. No. 10/846,150 filed May 14, 2004 and entitled "ANALYTE MEASURING DEVICE"; U.S. application Ser. No. 10/842,716 filed May 10, 2004 and entitled "BIOINTERFACE MEMBRANES INCORPORATING BIOACTIVE AGENTS"; U.S. application Ser. No. 10/657,843 filed Sep. 9, 2003 and entitled "DEVICE AND METHOD FOR DETERMINING ANALYTE LEVELS"; U.S. application Ser. No. 10/768,889 filed Jan. 29, 2004 and entitled "MEMBRANE FOR USE WITH IMPLANTABLE DEVICES"; U.S. application Ser. No. 10/633,367 filed Aug. 1, 2003 and entitled "SYSTEM AND METHODS FOR PROCESSING ANALYTE SENSOR DATA"; U.S. application Ser. No. 10/632,537 filed Aug. 1, 2003 and entitled "SYSTEM AND METHODS FOR PROCESSING ANALYTE SENSOR DATA"; U.S. application Ser. No. 10/633,404 filed Aug. 1, 2003 and entitled "SYSTEM AND METHODS FOR PROCESSING ANALYTE SENSOR DATA"; U.S. application Ser. No. 10/633,329 filed Aug. 1, 2003 and entitled "SYSTEM AND METHODS FOR PROCESSING ANALYTE SENSOR DATA".

All references cited herein, including but not limited to published and unpublished applications, patents, and literature references, and also including but not limited to the references listed in the Appendix, are incorporated herein by reference in their entirety and are hereby made a part of this specification. To the extent publications and patents or patent applications incorporated by reference contradict the disclosure contained in the specification, the specification is intended to supersede and/or take precedence over any such contradictory material.

The term "comprising" as used herein is synonymous with "including," "containing," or "characterized by," and is inclusive or open-ended and does not exclude additional, unrecited elements or method steps.

All numbers expressing quantities of ingredients, reaction conditions, and so forth used in the specification are to be understood as being modified in all instances by the term "about." Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention.

What is claimed is:

1. An analyte sensor, the sensor comprising an elongated flexible portion, wherein the elongated flexible portion comprises a first electrode and a second electrode at least partially surrounding at least a portion of the first electrode, wherein the first and/or second electrode is configured to produce a signal indicative of an analyte concentration in a host, and wherein the second electrode provides a variable stiffness of the sensor by a variable stiffness of the material of the second electrode and/or by a variable pitch of a helical configuration of the second electrode along at least a portion of its length.

2. The sensor of claim 1, further comprising an insulator located between the first electrode and the second electrode.

3. The sensor of claim 1, wherein the variable stiffness of the second electrode is provided by a variable cross-section of the second electrode.

4. The sensor of claim 1, wherein the variable stiffness of the second electrode is provided by a variable hardness of the second electrode.

5. The sensor of claim 4, wherein the variable hardness is produced by subjecting the second electrode to an annealing process.

6. The sensor of claim 1, wherein the wherein the variable stiffness of the second electrode is provided by a variable diameter.

7. The sensor of claim 1, wherein a distal portion of the sensor is more flexible than a proximal portion of the sensor.

8. The sensor of claim 1, wherein an intermediate portion of the sensor is more flexible than at least one of a distal portion of the sensor and a proximal portion of the sensor.

9. The sensor of claim 1, wherein a distal portion of the sensor is stiffer than at least one of an intermediate portion of the sensor and a proximal portion of the sensor.

10. The sensor of claim 1, wherein the first electrode comprises a solid cross-section.

11. The sensor of claim 1, wherein the sensor is configured and arranged such that after the sensor is transcutaneously inserted, the entire portion of the sensor that is in vivo directly contacts tissue.

12. The sensor of claim 1, wherein the elongated flexible portion comprises a distal portion configured and arranged with a flexibility that minimizes mechanical stresses caused by motion of the host.

13. The sensor of claim 1, further comprising sensor electronics adapted for mounting on a skin of a host, wherein the sensor electronics comprise electrical contacts configured and arranged for releasable connection with electrical contacts associated with the first and second electrodes.

14. The sensor of claim 13, wherein the elongated flexible portion comprises a proximal portion is configured and arranged with a stiffness that maintains a stable connection between the electrical contacts associated with the first and second electrodes and the electrical contacts of the sensor electronics housing.

15. The sensor of claim 1, wherein the sensor is configured to absorb a relative movement between an in vivo portion and an ex vivo portion.

16. An analyte sensor, the sensor comprising an in vivo portion adapted for insertion into a host and an ex vivo portion adapted for operable connection to a device that remains external to the host, wherein the in vivo portion of the sensor comprises a first electrode twisted with or around a second electrode along a length of the sensor in such a way that a stiffness of the sensor gradually changes along a length of the sensor where the first electrode is located, and wherein the first and/or second electrode is configured to produce a signal indicative of an analyte concentration in a host.

17. The sensor of claim 16, wherein the ex vivo portion is stiffer than the in vivo portion.

18. The sensor of claim 16, wherein an intermediate portion is more flexible than at least one of the in vivo portion and the ex vivo portion.

19. The sensor of claim 18, wherein the in vivo portion comprises a tip on an end of the sensor that is stiffer than a substantial portion of the sensor.

20. The sensor of claim 16, wherein at least one electrode comprises a wire in a helical configuration, and wherein a change in stiffness is provided by a varying a cross-section of the wire.

21. The sensor of claim 16, wherein the sensor is configured to absorb a relative movement between the in vivo portion and the ex vivo portion.

22. The sensor of claim 16, wherein the device comprises a housing adapted for mounting on a skin of a host, wherein the housing comprises electrical contacts operably connected to the sensor.

23. The sensor of claim 22, wherein the ex vivo portion of the sensor has a preselected stiffness to maintain a stable connection between the sensor and the electrical contacts.

24. The sensor of claim 16, wherein the in vivo portion of the sensor has a preselected flexibility to minimize mechanical stresses caused by motion of the host.

25. The sensor of claim 16, wherein a stiffness of the ex vivo portion of the sensor is greater than a stiffness of the in vivo portion of the sensor.

26. The sensor of claim 16, wherein at least one electrode comprises a wire, and wherein a change in stiffness is provided by a varying a hardness of the wire.

27. The sensor of 26, wherein the change is produced by subjecting the wire to an annealing process.

28. The sensor of claim 16, wherein an intermediate portion of the sensor is more flexible than at least one of the in vivo portion and the ex vivo portion.

29. The sensor of claim 28, wherein the in vivo portion comprises a tip on an end of the sensor that is stiffer than a substantial portion of the sensor.

30. The sensor of claim 16, further comprising a membrane covering the first and second electrodes.

31. The sensor of claim 16, wherein the first electrode at least partially surrounds the second electrode.

32. The sensor of claim 16, further comprising an insulator located between the first electrode and the second electrode.

33. The sensor of claim 16, wherein the second electrode comprises a solid cross-section.

34. The sensor of claim 16, wherein one of the first and second electrodes comprises a first working electrode and the other of the first and second electrodes comprises a second working electrode.

35. The sensor of claim 16, wherein the second electrode comprises a working electrode and the first electrode comprises a reference electrode.

36. The sensor of claim 16, wherein the sensor is configured and arranged such that after the sensor is transcutaneously inserted, the entire portion of the sensor that is in vivo directly contacts tissue.

37. An analyte sensor configured to produce a signal indicative of an analyte concentration in a host, the sensor comprising an in vivo portion adapted for insertion into a host and an ex vivo portion adapted for operable connection to a device that remains external to the host, wherein the in vivo portion of the sensor comprises a first electrode twisted with or around a second electrode along a length of the sensor in such a way that that a stiffness of the sensor gradually changes along a length of the sensor where the first electrode is located, wherein the ex vivo portion is stiffer than the in vivo portion, wherein at least one electrode comprises a wire in a helical configuration, and wherein the difference in stiffness between the ex vivo portion and the in vivo portion is provided by a varying pitch of the helical configuration.

38. An analyte sensor, the sensor comprising an in vivo portion adapted for insertion into a host and an ex vivo portion adapted for operable connection to a device that remains external to the host, wherein the in vivo portion of the sensor comprises a first electrode twisted with or around a second electrode along a length of the sensor in such a way that a stiffness of the sensor gradually changes along a length of the sensor where the first electrode is located, wherein the first and/or second electrode is configured to produce a signal indicative of an analyte concentration in a host and wherein the first electrode provides the change in stiffness of the sensor.

39. An analyte sensor, the sensor comprising an elongated flexible portion, wherein the elongated flexible portion comprises a first electrode and a second electrode at least partially surrounding at least a portion of the first electrode, wherein the first and/or second electrode is configured to produce a signal indicative of an analyte concentration in a host, and wherein the second electrode provides a variable stiffness of the sensor by a variable stiffness of the material of the second electrode along at least a portion of its length.

* * * * *

UNITED STATES PATENT AND TRADEMARK OFFICE
CERTIFICATE OF CORRECTION

| | |
|---|---|
| PATENT NO. | : 7,783,333 B2 |
| APPLICATION NO. | : 11/077759 |
| DATED | : August 24, 2010 |
| INVENTOR(S) | : Brister, et al. |

It is certified that error appears in the above-identified patent and that said Letters Patent is hereby corrected as shown below:

| Issued Patent | | Description of Discrepancy |
|---|---|---|
| On the Title Pg | Line | |
| (Item 56) | 14 | Under Other Publications, change "continuos" to --continuous--. |
| (Item 56) Pg 10 | 18 | Under Other Publications, change "Biomateials" to --Biomaterials--. |
| (Item 56) Pg 10 | 23 | Under Other Publications, change "mediates" to --mediate--. |
| (Item 56) Pg 11 | 23 | Under Other Publications, change "Continous" to --Continuous--. |
| (Item 56) Pg 11 | 29 | Under Other Publications, change "Mearsurement" to --Measurement--. |
| (Item 56) Pg 11 | 39 | Under Other Publications, change "Elecron" to --Electron--. |
| (Item 56) Pg 11 | 44 | Under Other Publications, change "adn" to --and--. |
| (Item 56) Pg 11 | 34 | Under Other Publications, change "glucsoe" to --glucose--. |
| (Item 56) Pg 12 | 13 | Under Other Publications, change "Clincial" to --Clinical--. |
| (Item 56) Pg 12 | 14 | Under Other Publications, change "patents" to --patients--. |
| (Item 56) Page 12 | 47 | Under Other Publications, change "fo" to --of--. |
| (Item 56) Page 12 | 64 | Under Other Publications, change "Tranducers" to --Transducers--. |
| (Item 56) Page 12 | 63-64 | Under Other Publications, change "basedon on" to --based on--. |

Signed and Sealed this
Twenty-second Day of February, 2011

David J. Kappos
*Director of the United States Patent and Trademark Office*

CERTIFICATE OF CORRECTION (continued)

U.S. Pat. No. 7,783,333 B2

On the Title Pg

| | | |
|---|---|---|
| (Item 56) Page 12 | 67 | Under Other Publications, change "reliablity" to --reliability--. |
| (Item 56) Page 12 | 68 | Under Other Publications, change "Biollogy" to --Biology--. |
| (Item 56) Page 14 | 40 | Under Other Publications, change "artifical" to --artificial--. |
| (Item 56) Page 14 | 62 | Under Other Publications, change "dynamcs" to --dynamics--. |
| (Item 56) Page 14 | 13 | Under Other Publications, change "Diabetese" to --Diabetes--. |
| (Item 56) Page 14 | 31 | Under Other Publications, change "inactiviation" to --inactivation--. |
| (Item 56) Page 15 | 52 | Under Other Publications, change "activitiy," to --activity,--. |
| (Item 56) Page 15 | 69 | Under Other Publications, change "Beioelectronics," to --Bioelectronics,--. |
| (Item 56) Page 15 | 70 | Under Other Publications, change "glocuse" to --glucose--. |
| (Item 56) Page 15 | 10 | Under Other Publications, change "valication" to --validation--. |
| (Item 56) Page 15 | 11 | Under Other Publications, change "iunsulin interaaction in tyhpe" to --insulin interaction in type--. |
| (Item 56) Page 15 | 40 | Under Other Publications, change "artifical" to --artificial--. |
| (Item 56) Page 15 | 49 | Under Other Publications, change "amperometeric" to --amperometric--. |
| (Item 56) Page 16 | 13 | Under Other Publications, change "metobolites," to --metabolites,--. |
| (Item 56) Page 16 | 25 | Under Other Publications, change "assitance" to --assistance--. |
| (Item 56) Page 16 | 56 | Under Other Publications, change "pancrease" to --pancreas--. |
| (Item 56) Page 17 | 30 | Under Other Publications, change "Deabetes" to --Diabetes--. |

| Col. | Line | |
|---|---|---|
| 5 | 10 | change "arid/or" to --and/or--. |
| 9 | 35 | change "34ais" to --34a is--. |
| 12 | 35 (Approx.) | change "x," to --$x_1$--. |
| 16 | 42 | In Claim 6, after "wherein the" delete "wherein the". (Second Occurrence) |

CERTIFICATE OF CORRECTION (continued)
U.S. Pat. No. 7,783,333 B2

| Col. | Line | |
|---|---|---|
| 17 | 51 | In Claim 27, change "of 26," to --of claim 26,--. |
| 18 | 28 (Approx.) | In Claim 37, after "that" delete "that". (Second Occurrence) |